US007208656B2

(12) United States Patent
Isaac et al.

(10) Patent No.: US 7,208,656 B2
(45) Date of Patent: Apr. 24, 2007

(54) **NUCLEOTIDE SEQUENCES ENCODING ANTHONOMOUS TOXIC POLYPEPTIDES FROM *BACILLUS THURINGIENSIS***

(75) Inventors: Barbara Isaac, St. Charles, MO (US); Elysia K. Krieger, Kirkwood, MO (US); Anne-Marie Light Mettus, Feasterville, PA (US); Farhad Moshiri, Chesterfield, MO (US); Sakuntala Sivasupramanian, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/302,357

(22) Filed: Dec. 13, 2005

(65) Prior Publication Data

US 2006/0218666 A1    Sep. 28, 2006

Related U.S. Application Data

(62) Division of application No. 10/360,899, filed on Feb. 7, 2003, now abandoned, which is a division of application No. 09/853,533, filed on May 11, 2001, now Pat. No. 6,541,448.

(60) Provisional application No. 60/204,367, filed on May 15, 2000.

(51) Int. Cl.
    *A01H 5/00*      (2006.01)
    *C12P 21/06*    (2006.01)
    *C07H 17/00*   (2006.01)
    *C07K 14/00*   (2006.01)

(52) U.S. Cl. .............. 800/302; 800/260; 800/295; 435/69.1; 435/320.1; 435/252.3; 435/325; 536/32.1; 530/350

(58) Field of Classification Search .............. 536/23.1; 435/69.1, 320.1, 252.3, 325; 530/350; 800/260, 800/295, 302

See application file for complete search history.

(56) References Cited

U.S. PATENT DOCUMENTS

| 5,382,429 A | 1/1995 | Donovan et al. |
|---|---|---|
| 5,436,002 A | 7/1995 | Payne et al. |
| 5,500,365 A | 3/1996 | Fischhoff et al. |
| 5,596,071 A | 1/1997 | Payne et al. |

FOREIGN PATENT DOCUMENTS

WO      WO 00/26378     5/2000

OTHER PUBLICATIONS

Rukmini et al., *Bacillus thuringiensis* crystal d-endotoxin: Role of proteases in the conversion of protoxin to toxin, *Biochimie* 82:109-116 (2000).

*Primary Examiner*—Karen Cochrane Carlson
(74) *Attorney, Agent, or Firm*—Timothy K. Ball

(57) ABSTRACT

A novel gene encoding a Coleopteran inhibitory *Bacillus thuringiensis* insecticidal crystal protein is disclosed. The protein, tIC851, is insecticidally active and provides plant protection from at least cotton boll weevil, *Anthomomus grandis*, when applied to plants in an insecticidally effective composition.

18 Claims, 5 Drawing Sheets

```
aaatattttt aaagggggat acgtaat ttg aat tct aaa tct atc atc gaa aaa         54
                             Leu Asn Ser Lys Ser Ile Ile Glu Lys
                              1               5
ggg gta caa gag aat caa tat att gat att cgt aac ata tgt agc att          102
Gly Val Gln Glu Asn Gln Tyr Ile Asp Ile Arg Asn Ile Cys Ser Ile
10              15                  20                  25 aat ggt tct gct aaa ttt gat cct aat act aac att aca acc tta aca          150
Asn Gly Ser Ala Lys Phe Asp Pro Asn Thr Asn Ile Thr Thr Leu Thr
                30                  35                  40 gaa gct atc aat tct caa gca gga gcg att gct gga aaa act gcc cta          198
Glu Ala Ile Asn Ser Gln Ala Gly Ala Ile Ala Gly Lys Thr Ala Leu
            45                  50                  55 gat atg aga cgt gat ttt act ctc gta gca gat ata tac cta ggg tct          246
Asp Met Arg Arg Asp Phe Thr Leu Val Ala Asp Ile Tyr Leu Gly Ser
        60                  65                  70 aaa agt agt gga gct gat ggt att gct ata gcg ttt cat aga gga tca          294
Lys Ser Ser Gly Ala Asp Gly Ile Ala Ile Ala Phe His Arg Gly Ser
    75                  80                  85 att ggt ttt atc ggt acc atg ggt gga ggc tta ggg att cta gga gca          342
Ile Gly Phe Ile Gly Thr Met Gly Gly Gly Leu Gly Ile Leu Gly Ala
90                  95                  100                 105 cca aac ggg ata gga ttt gaa ata gat acg tat tgg aaa gca act tca          390
Pro Asn Gly Ile Gly Phe Glu Ile Asp Thr Tyr Trp Lys Ala Thr Ser
                110                 115                 120 gat gaa aca ggc gat tca ttt gga cat ggt caa atg aat gga gca cat          438
Asp Glu Thr Gly Asp Ser Phe Gly His Gly Gln Met Asn Gly Ala His
            125                 130                 135 gcg gga ttt gta agt aca aat cga aat gca agc tat tta aca gcc tta          486
Ala Gly Phe Val Ser Thr Asn Arg Asn Ala Ser Tyr Leu Thr Ala Leu
        140                 145                 150 gct cct atg caa aaa ata cct gca cct aat aat aaa tgg cgg gtt cta          534
Ala Pro Met Gln Lys Ile Pro Ala Pro Asn Asn Lys Trp Arg Val Leu
    155                 160                 165 act atc aat tgg gat gcg cgt aac aac aaa cta aca gca cgg ctt caa          582
Thr Ile Asn Trp Asp Ala Arg Asn Asn Lys Leu Thr Ala Arg Leu Gln
170                 175                 180                 185 gag aaa agt aat gat gct tct act agc act cct agt cca aga tat caa          630
Glu Lys Ser Asn Asp Ala Ser Thr Ser Thr Pro Ser Pro Arg Tyr Gln
                190                 195                 200
```

Figure 1a

| | | | | | | | | | | | | | | | | |
|---|---|---|---|---|---|---|---|---|---|---|---|---|---|---|---|---|
| aca | tgg | gaa | cta | tta | aat | cct | gcg | ttt | gat | tta | aat | cag | aaa | tat | act | 678 |
| Thr | Trp | Glu | Leu | Leu | Asn | Pro | Ala | Phe | Asp | Leu | Asn | Gln | Lys | Tyr | Thr | |
| | | 205 | | | | | 210 | | | | | 215 | | | | |
| ttt | att | atc | ggc | tca | gct | aca | ggg | gct | gct | aat | aac | aag | cat | cag | att | 726 |
| Phe | Ile | Ile | Gly | Ser | Ala | Thr | Gly | Ala | Ala | Asn | Asn | Lys | His | Gln | Ile | |
| | | 220 | | | | | 225 | | | | | 230 | | | | |
| gga | gtt | act | ttg | ttt | gaa | gca | tac | ttc | aca | aaa | cca | act | ata | gag | gca | 774 |
| Gly | Val | Thr | Leu | Phe | Glu | Ala | Tyr | Phe | Thr | Lys | Pro | Thr | Ile | Glu | Ala | |
| | 235 | | | | | 240 | | | | | 245 | | | | | |
| aat | cct | gtt | gat | att | gaa | cta | ggc | aca | gcg | ttt | gat | cca | tta | aac | cat | 822 |
| Asn | Pro | Val | Asp | Ile | Glu | Leu | Gly | Thr | Ala | Phe | Asp | Pro | Leu | Asn | His | |
| 250 | | | | | 255 | | | | | 260 | | | | | 265 | |
| gag | cca | att | gga | ctc | aaa | gca | aca | gat | gaa | gta | gat | gga | gat | ata | aca | 870 |
| Glu | Pro | Ile | Gly | Leu | Lys | Ala | Thr | Asp | Glu | Val | Asp | Gly | Asp | Ile | Thr | |
| | | | | 270 | | | | | 275 | | | | | 280 | | |
| aag | gac | att | acg | gta | gaa | ttt | aat | gac | ata | gat | acc | tcc | aaa | cca | ggt | 918 |
| Lys | Asp | Ile | Thr | Val | Glu | Phe | Asn | Asp | Ile | Asp | Thr | Ser | Lys | Pro | Gly | |
| | | | 285 | | | | | 290 | | | | | 295 | | | |
| gca | tac | cgt | gta | aca | tat | aaa | gta | gta | aat | agt | tat | gga | gaa | agt | gat | 966 |
| Ala | Tyr | Arg | Val | Thr | Tyr | Lys | Val | Val | Asn | Ser | Tyr | Gly | Glu | Ser | Asp | |
| | | 300 | | | | | 305 | | | | | 310 | | | | |
| gag | aaa | aca | ata | gaa | gtc | gta | gta | tac | acg | aaa | cca | act | ata | act | gca | 1014 |
| Glu | Lys | Thr | Ile | Glu | Val | Val | Val | Tyr | Thr | Lys | Pro | Thr | Ile | Thr | Ala | |
| | 315 | | | | | 320 | | | | | 325 | | | | | |
| cat | gat | att | acg | att | aag | aaa | gac | tta | gca | ttt | gat | cca | tta | aac | tat | 1062 |
| His | Asp | Ile | Thr | Ile | Lys | Lys | Asp | Leu | Ala | Phe | Asp | Pro | Leu | Asn | Tyr | |
| 330 | | | | | 335 | | | | | 340 | | | | | 345 | |
| gaa | cca | att | gga | ctc | aaa | gca | acc | gat | cca | att | gat | gga | gat | ata | aca | 1110 |
| Glu | Pro | Ile | Gly | Leu | Lys | Ala | Thr | Asp | Pro | Ile | Asp | Gly | Asp | Ile | Thr | |
| | | | | 350 | | | | | 355 | | | | | 360 | | |
| gat | aaa | atc | gct | gta | aaa | ttt | aat | aat | gtc | gat | acc | tct | aaa | ccg | ggt | 1158 |
| Asp | Lys | Ile | Ala | Val | Lys | Phe | Asn | Asn | Val | Asp | Thr | Ser | Lys | Pro | Gly | |
| | | | 365 | | | | | 370 | | | | | 375 | | | |
| aaa | tac | cat | gta | aca | tat | aaa | gtg | ata | aat | agt | tat | gaa | aaa | att | gat | 1206 |
| Lys | Tyr | His | Val | Thr | Tyr | Lys | Val | Ile | Asn | Ser | Tyr | Glu | Lys | Ile | Asp | |
| | | 380 | | | | | 385 | | | | | 390 | | | | |
| gaa | aaa | aca | ata | gag | gtc | aca | gta | tat | acg | aaa | cca | tct | ata | gtg | gca | 1254 |
| Glu | Lys | Thr | Ile | Glu | Val | Thr | Val | Tyr | Thr | Lys | Pro | Ser | Ile | Val | Ala | |
| | 395 | | | | | 400 | | | | | 405 | | | | | |
| cat | gat | gtt | gag | att | aaa | aaa | gat | acg | gca | ttt | gat | ccg | tta | aac | tat | 1302 |
| His | Asp | Val | Glu | Ile | Lys | Lys | Asp | Thr | Ala | Phe | Asp | Pro | Leu | Asn | Tyr | |
| 410 | | | | | 415 | | | | | 420 | | | | | 425 | |

Figure 1b

```
gaa cca att ggg ctc aaa gca acc gat cca att gat gga gat ata aca      1350
Glu Pro Ile Gly Leu Lys Ala Thr Asp Pro Ile Asp Gly Asp Ile Thr
            430                 435                 440 gat aaa att acg gta gaa tct aat gat gtt gat acc tct aaa cca ggt      1398
Asp Lys Ile Thr Val Glu Ser Asn Asp Val Asp Thr Ser Lys Pro Gly
            445                 450                 455 gca tat agt gtg aaa tat aaa gta gta aat aat tat gaa gaa agt gac      1446
Ala Tyr Ser Val Lys Tyr Lys Val Val Asn Asn Tyr Glu Glu Ser Asp
            460                 465                 470 gaa aaa aca att gcc gtt aca gta cct gtt ata gat gat ggg tgg gag      1494
Glu Lys Thr Ile Ala Val Thr Val Pro Val Ile Asp Asp Gly Trp Glu
    475                 480                 485 aat ggc gat ccg aca gga tgg aaa ttc ttc tct ggt gaa acc att act      1542
Asn Gly Asp Pro Thr Gly Trp Lys Phe Phe Ser Gly Glu Thr Ile Thr
490                 495                 500                 505 cta gaa gat gat gaa gag cat gct ctt aat ggt aaa tgg gta ttt tat      1590
Leu Glu Asp Asp Glu Glu His Ala Leu Asn Gly Lys Trp Val Phe Tyr
                510                 515                 520 gct gat aaa cat gta gca ata tac aaa caa gta gag ttg aag aat aat      1638
Ala Asp Lys His Val Ala Ile Tyr Lys Gln Val Glu Leu Lys Asn Asn
            525                 530                 535 atc cct tat caa att aca gta tat gtt aaa cca gaa gat gaa gga act      1686
Ile Pro Tyr Gln Ile Thr Val Tyr Val Lys Pro Glu Asp Glu Gly Thr
            540                 545                 550 gtg gca cac cat att gtt aaa gta tct ttc aaa tct gat tct gct ggt      1734
Val Ala His His Ile Val Lys Val Ser Phe Lys Ser Asp Ser Ala Gly
    555                 560                 565 cca gaa agt gaa gaa gtt ata aat gaa aga tta att gat gca gaa cag      1782
Pro Glu Ser Glu Glu Val Ile Asn Glu Arg Leu Ile Asp Ala Glu Gln
570                 575                 580                 585 ata caa aaa gga tac aga aag tta aca agt att cca ttt aca cca aca      1830
Ile Gln Lys Gly Tyr Arg Lys Leu Thr Ser Ile Pro Phe Thr Pro Thr
                590                 595                 600 acc att gtt ccc aac aaa aaa cca gtg ata att gtt gaa aac ttt tta      1878
Thr Ile Val Pro Asn Lys Lys Pro Val Ile Ile Val Glu Asn Phe Leu
            605                 610                 615 cca gga tgg ata ggt gga gtt aga ata att gta gag cct aca aag          1923
Pro Gly Trp Ile Gly Gly Val Arg Ile Ile Val Glu Pro Thr Lys
            620                 625                 630 taagaattat aaactagctt ttaataaata tatttaaaaa at                        1965
```

Figure 1c

```
Cry22Aa   MKEQNLNKYDEITVQAASDYIDIRPIFQTNGSATFNSNTNITTLTQAINS            50
ET70      MKDSISKGYDEITVQA-SDYIDIRSIFQTNGSATFNSTTNITTLTQATNS            49
tIC851    MN---SKSIIEKGVQE-NQYIDIRNICSINGSAKFDPNTNITTLTEAINS            46
          *.     .  * .**. ..*****  *  .****.*...*******.*.**

Cry22Aa   QAGAIAGKTALDMRHDFTFRADIFLGTKSNGADGIAIAFHRGSIGFVGTK            100
ET70      QAGAIAGKTALDMRHDFTFRADIFLGTKSNGADGIAIAFHRGSIGFVGEK            99
tIC851    QAGAIAGKTALDMRRDFTLVADIYLGSKSSGADGIAIAFHRGSIGFIGTM            96
          **************.***. ***.**.**.******************.*..

Cry22Aa   GGGLGILGAPKGIGFELDTYANAPEDEVGDSFGHGAMKGSFPSFPNGYPH            150
ET70      GGGLGILGALKGIGFELDTYANAPQDEQGDSFGHGAMRGLFPGFPNGYPH            149
tIC851    GGGLGILGAPNGIGFEIDTYWKATSDETGDSFGHGQMNG---------AH            137
          *********  .*****.*** .*  ** *******.*.*         .*

Cry22Aa   AGFVSTDKNSRWLSALAQMQRIAAPNGRWRRLEIRWDARNKELTANLQDL            200
ET70      AGFVSTDKNRGWLSALAQMQRIAAPNGRWRRLAIHWDARNKKLTANLEDL            199
tIC851    AGFVSTNRNASYLTALAPMQKIPAPNNKWRVLTINWDARNNKLTARLQE-            186
          ******..*   .*.***.**.*.***..**..  .****..***..**..

Cry22Aa   TFNDITVGEKPRTPRTATWRLVNPAFELDQKYTFVIGSATGASNNLHQIG            250
ET70      TFNDSTVLVKPRTPRYARWELSNPAFELDQKYTFVIGSATGASNNLHQIG            249
tIC851    --KSNDASTSTPSPRYQTWELLNPAFDLNQKYTFIIGSATGAANNKHQIG            234
          ..  ..   ....** . * * ****.*.*****.*******.** ****

Cry22Aa   IIEFDAYFTKPTIEANNVNVPVGATFNPKTYPGINLRATDEIDGDLTSKI            300
ET70      IIEFDAYFTKPTIEANNVSVPVGATFNPKTYPGINLRATDEIDGDLTSEI            299
tIC851    VTLFEAYFTKPTIEANPVDIELGTAFDPLNHEPIGLKATDEVDGDITKDI            284
          ..  *.**********  *.. .*..*  ..  *.*.****.***.*..*

Cry22Aa   IVKANNVNTSKTGVYYVTYYVENSYGESDEKTIEVTVFSNPTIIASDVEI            350
ET70      IVTDNNVNTSKSGVYNVTYYVKNSYGESDEKTIEVTVFSNPTIIASDVEI            349
tIC851    TVEFNDIDTSKPGAYRVTYKVVNSYGESDEKTIEVVVYTKPTITAHDITI            334
          .*. *...***.*.* ***.* ************* * *.***.*..*

Cry22Aa   EKGESFNPLTDSRVGLSAQDSLGNDITQNVKVKSSNVDTSKPGEYEVVFE            400
ET70      EKGESFNPLTDSRVRLSAQDSLGNDITSKVKVKSSNVDTSKPGEYDVVFE            399
tIC851    KKDLAFDPL---------------------------------NYE----            346
          .*.  .*.**                                 .*.

Cry22Aa   VTDSFGGKAEKDFKVTVLGQPSIEANNVELEIDDSLDPLTDAKVGLRAKD            450
ET70      VTDNFGGKAEKEIKVTVLGQPSIEANDVELEIGDLFNPLTDSQVGLRAKD            449
tIC851    ---------------------------------------PIGLKATD              354
                                                   .**.*.*

Cry22Aa   SLGNDITKDIKVKFNNVDTSNSGKYEVIFEVTDRFGKKAEKSIEVLVLGE            500
ET70      SLGKDITNDVKVKSSNVDTSKPGEYEVVFEVTDRFGKKAEKSIKVLVLGE            499
tIC851    PIDGDITDKIAVKFNNVDTSKPGKYHVTYKVINSYEKIDEKTIEVTVYTK            404
          ...  ***... **  *****.*. ** * .*   *  .  .  **.**. *..

Cry22Aa   PSIEANDVEVNKGETFEPLTDSRVGLRAKDSLGNDITKDVKIKSSNVDTS            550
ET70      PSIEANNVEIEKDERFDPLTDSRVGLRAKDSLGKDITNDVKVKSSNVDTS            549
tIC851    PSIVAHDVEIKKDTAFDPLNYEPIGLKATDPIDGDITDKITVESNDVDTS            454
          *** *..**..*..  *.**.   ..**. .*.   ***... *..*.****
```

Figure 2a

```
Cry22Aa    KPGEYEVVFEVTDRFGKYVEKTIGVIVPVIDDEWEDGNVNGWKFYAGQDI    600
ET70       KPGEYEVVFEVTDRFGKYVKKLIVVIVPVIDDEWEDGNVNGWKFYAGQDI    599
tIC851     KPGAYSVKYKVVNNYEESDEKTIAVTVPVIDDGWENGDPTGWKFFSGETI    504
           ***.*.*  ..*......   .* * *.******.**.*. .****..*..*

Cry22Aa    KLLKDPDKAYKGDYVFYDSRHVAISKTIPLTDLQINTNYEITVYAKAES-    649
ET70       TLLKDPEKAYKGEYVFYDSRHAAISKTIPVTDLQVGGNYEITVYVKAES-    648
tIC851     TLEDDEEHALNGKWVFYADKHVAIYKQV---ELKNNIPYQITVYVKPEDE    551
           .* .* ..* .*..***...*.** * .    .*. .  *.****.*.*.

Cry22Aa    ---GDHHLKVTYKKDPAGPEEPPVFNRLISTGTLVEKDYRELKGT-FRVT    695
ET70       ---GDHHLKVTYKKDPKGPEEPPVFNRLISTGKLVEKDYRELKGT-FRVT    694
tIC851     GTVAHHIVKVSFKSDSAGPESEEVINERLIDAEQIQKGYRKLTSIPFTPT    601
           ..*.**.*.*. ***.  *.*    ....*.**.*... * *

Cry22Aa    EL--NKAPLIIVENFGAGYIGGIRIV--KIS    722
ET70       EL--NQAPLIIVENFGAGYIGGIRIV--KIS    721
tIC851     TIVPNKKPVIIVENFLPGWIGGVRIIVEPTK    632
           ..  *. *.******.*.***.**.   ..
```

Figure 2b

NUCLEOTIDE SEQUENCES ENCODING ANTHONOMOUS TOXIC POLYPEPTIDES FROM *BACILLUS THURINGIENSIS*

CROSS REFERENCE TO RELATED APPLICATIONS

This application is a divisional of application Ser. No. 10/360,899 filed Feb. 7, 2003, now abandoned; which is a divisional of application Ser. No. 09/853,533 filed May 11, 2001, now U.S. Pat. No. 6,541,448; which claims the benefit of priority to U.S. Provisional Application Ser. No. 60/204,367 filed May 15, 2000.

BACKGROUND OF THE INVENTION

1.0 BACKGROUND OF THE INVENTION

1.1 Field of the Invention

The present invention relates generally to the fields of molecular biology. Methods and compositions comprising DNA sequences, and polypeptides derived from *Bacillus thuringiensis* for use in insecticidal formulations and the development of transgenic insect-resistant plants are provided. Novel nucleic acids obtained from *Bacillus thuringiensis* that encode coleopteran-toxic polypeptides are disclosed. Various methods for making and using these nucleic acids, synthetically modified DNA sequences encoding tIC851 polypeptides, and native and synthetic polypeptide compositions are also disclosed. The use of DNA sequences as diagnostic probes and templates for protein synthesis, and the use of polypeptides, fusion proteins, antibodies, and peptide fragments in various insecticidal, immunological, and diagnostic applications are also disclosed, as are methods of making and using nucleic acid sequences in the development of transgenic plant cells comprising the polynucleotides.

1.2 Description of the Related Art

Environmentally-sensitive methods for controlling or eradicating insect infestation are desirable in many instances, in particular when crops of commercial interest are at issue. The most widely used environmentally-sensitive insecticidal formulations developed in recent years have been composed of microbial pesticides derived from the bacterium *Bacillus thuringiensis*. *B. thuringiensis* is well known in the art, and is characterized morphologically as a Gram-positive bacterium that produces crystal proteins or inclusion bodies which are aggregations of proteins specifically toxic to certain orders and species of insects. Many different strains of *B. thuringiensis* have been shown to produce insecticidal crystal proteins. Compositions including *B. thuringiensis* strains which produce insecticidal proteins have been commercially-available and used as environmentally-acceptable insecticides because they are quite toxic to the specific target insect, but are harmless to plants and other non-targeted organisms.

There are several toxin categories established based on primary structure information and the degree of toxin similarities to another. Over the past decade research on the structure and function of *B. thuringiensis* toxins has covered all of the major toxin categories, and while these toxins differ in specific structure and function, general similarities in the structure and function are assumed. Based on the accumulated knowledge of *B. thuringiensis* toxins, a generalized mode of action for *B. thuringiensis* toxins has been created and includes: ingestion by the insect, solubilization in the insect midgut (a combination stomach and small intestine), resistance to digestive enzymes sometimes with partial digestion actually "activating" the toxin, binding to the midgut cells, formation of a pore in the insect cells and the disruption of cellular homeostasis (English and Slatin, 1992).

Many of the δ-endotoxins are related to various degrees by similarities in their amino acid sequences. Historically, the proteins and the genes which encode them were classified based largely upon their spectrum of insecticidal activity. The review by Schnepf et al. (Microbiol. Mol. Biol. Rev. (1998) 62:775–806) discusses the genes and proteins that were identified in *B. thuringiensis* prior to 1998, and sets forth the most recent nomenclature and classification scheme as applied to *B. thuringiensis* insecticidal genes and proteins. Using older nomenclature classification schemes, cry1 genes were deemed to encode lepidopteran-toxic Cry1 proteins, cry2 genes were deemed to encode Cry2 proteins toxic to both lepidopterans and dipterans, cry3 genes were deemed to encode coleopteran-toxic Cry3 proteins, and cry4 genes were deemed to encode dipteran-toxic Cry4 proteins. However, new nomenclature systematically classifies the Cry proteins based upon amino acid sequence homology rather than upon insect target specificities. The classification scheme for many known toxins, not including allelic variations in individual proteins, including dendograms and full *Bacillus thuringiensis* toxin lists is summarized and regularly updated at epunix.biols.susx.ac.uk/Home/Neil_Crickmore/Bt/index.html Most of the nearly 200 Bt crystal protein toxins presently known have some degree of lepidopteran activity associated with them. The large majority of *Bacillus thuringiensis* insecticidal proteins which have been identified do not have coleopteran controlling activity. Therefore, it is particularly important at least for commercial purposes to identify additional coleopteran specific insecticidal proteins.

Cry3 proteins generally display coleopteran activity, however, these generally have limited host range specificity and are not significantly toxic to target pests unless ingested in very high doses. The cloning and expression of the cry3Bb gene has been described (Donovan et al., 1992). This gene codes for a protein of 74 kDa with activity against Coleopteran insects, particularly the Colorado potato beetle (CPB) and the southern corn root worm (SCRW). Improved Cry3Bb proteins have been engineered which display increased toxicity at the same or lower doses than the wild type protein (U.S. Pat. No. 6,023,013; Feb. 8, 2000).

A *B. thuringiensis* strain, PS201T6, was reported to have activity against WCRW (*Diabrotica virgifera virgifera*) (U.S. Pat. No. 5,436,002). This strain also had activity against *Musca domestica*, *Aedes aegypti*, and *Liriomyza trifoli*. The vip1A gene, which produces a vegetative, soluble, insecticidal protein, has been cloned and sequenced (Intl. Pat. Appl. Pub. No. WO 96/10083, 1996). This gene produces a protein of approximately 80 kDa with activity against both WCRW and Northern Corn Root Worm (NCRW). Another toxin protein with activity against coleopteran insects, including WCRW, is Cry1Ia, an 81-kDa polypeptide, the gene encoding which has been cloned and sequenced (Intl. Pat. Appl. Pub. No. WO 90/13651, 1990).

2.0 SUMMARY OF THE INVENTION

The polypeptide of the present invention and the novel DNA sequences that encode the protein represent a new *B. thuringiensis* crystal protein and gene, and share only insubstantial sequence homology with any previously identified coleopteran inhibitory endotoxins described in the prior art.

Similarly, the *B. thuringiensis* strains of the present invention comprise novel gene sequences that express a polypeptide having insecticidal activity against coleopteran insects, the cotton boll weevil (*Anthonomus grandis* Boheman) in particular.

Disclosed and claimed herein is an isolated *Bacillus thuringiensis* δ-endotoxin polypeptide comprising SEQ ID NO:8. The inventors have identified an insecticidally-active polypeptide comprising the 632 amino acid long sequence of SEQ ID NO:8 which displays insecticidal activity against coleopteran insects. For example, the inventors have shown that a δ-endotoxin polypeptide comprising the sequence of SEQ ID NO:8 has insecticidal activity against boll weevil larvae (BWV), but not against western corn rootworm larvae.

The polypeptide of SEQ ID NO:8 is encoded by a nucleic acid segment comprising at least the open reading frame as shown in SEQ ID NO:7 from nucleotide position 28 through nucleotide position 1923. The invention also discloses compositions and insecticidal formulations that comprise such a polypeptide. Such composition may be a cell extract, cell suspension, cell homogenate, cell lysate, cell supernatant, cell filtrate, or cell pellet of a bacteria cell that comprises a polynucleotide that encodes such a polypeptide. Exemplary bacterial cells that produce such a polypeptide include *Bacillus thuringiensis* EG4135 and EG4268, deposited with NRRL respectively on Apr. 28, 2000. The composition as described in detail below may be formulated as a powder, dust, pellet, granule, spray, emulsion, colloid, solution, or such like, and may be preparable by such conventional means as desiccation, lyophilization, homogenization, extraction, filtration, centrifugation, sedimentation, or concentration of a culture of cells comprising the polypeptide. Preferably such compositions are obtainable from cultures of *Bacillus thuringiensis* EG4135 and EG4268 cells. In all such compositions that contain at least one such insecticidal polypeptide, the polypeptide may be present in a concentration of from about 0.001% to about 99% by weight.

An exemplary insecticidal polypeptide formulation may be prepared by a process comprising the steps of culturing *Bacillus thuringiensis* EG4135 and EG4268 cells under conditions effective to produce the insecticidal polypeptide; and obtaining the insecticidal polypeptide so produced.

For example, the invention discloses and claims a method of preparing a δ-endotoxin polypeptide having insecticidal activity against a coleopteran insect. The method generally involves isolating from a culture of *Bacillus thuringiensis* EG4135 and EG4268 cells that have been grown under appropriate conditions, the δ-endotoxin polypeptide produced by the cells. Such polypeptides may be isolated from the cell culture or supernatant or from spore suspensions derived from the cell culture and used in the native form, or may be otherwise purified or concentrated as appropriate for the particular application.

A method of controlling a coleopteran insect population is also provided by the invention. The method generally involves contacting the population with an insecticidally-effective amount of a polypeptide comprising the amino acid sequence of SEQ ID NO:8. Such methods may be used to kill or reduce the numbers of coleopteran insects in a given area, or may be prophylactically applied to an environmental area to prevent infestation by a susceptible insect. Preferably the insect ingests, or is contacted with, an insecticidally-effective amount of the polypeptide.

Additionally, the invention provides a purified antibody that specifically binds to the insecticidal polypeptide. Also provided are methods of preparing such an antibody, and methods for using the antibody to isolate, identify, characterize, and/or purify polypeptides to which such an antibody specifically binds. Immunological kits and immunodetection methods useful in the identification of such polypeptides and peptide fragments and/or epitopes thereof are provided in detail herein, and also represent important aspects of the present invention.

Such antibodies may be used to detect the presence of such polypeptides in a sample, or may be used as described hereinbelow in a variety of immunological methods. An exemplary method for detecting a δ-endotoxin polypeptide in a biological sample generally involves obtaining a biological sample suspected of containing a δ-endotoxin polypeptide; contacting the sample with an antibody that specifically binds to the polypeptide, under conditions effective to allow the formation of complexes; and detecting the complexes so formed.

For such methods, the invention also provides an immunodetection kit. Such a kit generally contains, in suitable container means, an antibody that binds to the δ-endotoxin polypeptide, and at least a first immunodetection reagent. Optionally, the kit may provide additional reagents or instructions for using the antibody in the detection of δ-endotoxin polypeptides in a sample.

Preparation of such antibodies may be achieved using the disclosed polypeptide as an antigen in an animal as described below. Antigenic epitopes, shorter peptides, peptide fusions, carrier-linked peptide fragments, and the like may also be generated from a whole or a portion of the polypeptide sequence disclosed in SEQ ID NO:8. Particularly preferred peptides are those that comprise at least 10 contiguous amino acids from the sequence disclosed in SEQ ID NO:8.

In another embodiment, the present invention also provides nucleic acid segments that comprise a selected nucleotide sequence region that comprises the polynucleotide sequence of SEQ ID NO:7. In preferred embodiments, this selected nucleotide sequence region comprises a gene that encodes a polypeptide comprising at least SEQ ID NO:8.

Another aspect of the invention relates to a biologically-pure culture of a wild-type *B. thuringiensis* bacterium selected from the strains EG4135 and EG4268, deposited on Apr. 28, 2000 with the Agricultural Research Culture Collection, Northern Regional Research Laboratory (NRRL), Peoria, Ill. Also deposited was strain sIC8501 which is an *E. coli* DH5α containing plasmid pIC17501 which contains at least the native *B. thuringiensis* strain EG4135 tIC851 coding sequence. These strains were deposited under the terms of the Budapest Treaty, and viability statements pursuant to International Receipt Form BP/4 were obtained. *B. thuringiensis* strains EG4135 and EG4268 are naturally-occurring strains that contain at least one sequence region encoding the 632 amino acid long polypeptide sequence in SEQ ID NO:8.

A further embodiment of the invention relates to a vector comprising a sequence region that encodes a polypeptide comprising the amino acid sequence of SEQ ID NO:8, a recombinant host cell transformed with such a recombinant vector, and biologically-pure cultures of recombinant bacteria transformed with a polynucleotide sequence that encodes the polypeptide disclosed in SEQ ID NO:8. Exemplary vectors, recombinant host cells, transgenic cell lines, and transgenic plants comprising at least a first sequence region that encodes a polypeptide comprising the sequence of SEQ ID NO:8 are described in detail herein.

The present invention also provides transformed host cells, embryonic plant tissue, plant calli, plantlets, and transgenic plants that comprise a selected sequence region that encodes the insecticidal polypeptide. Such cells are preferably prokaryotic or eukaryotic cells such as bacterial, fungal, or plant cells, with exemplary bacterial cells including *Bacillus thuringiensis, Bacillus subtilis, Bacillus megaterium, Bacillus cereus, Escherichia, Salmonella, Agrobacterium* or *Pseudomonas* cells.

The plants and plant host cells are preferably monocotyledonous or dicotyledonous plant cells such as corn, wheat, soybean, oat, cotton, rice, rye, sorghum, sugarcane, tomato, tobacco, kapok, flax, potato, barley, turf grass, pasture grass, berry, fruit, legume, vegetable, ornamental plant, shrub, cactus, succulent, and tree cell.

Transgenic plants of the present invention preferably have incorporated into their genome or transformed into their chloroplast or plastid genomes a selected polynucleotide (or "transgene"), that comprises at least a first sequence region that encodes the insecticidal polypeptide of SEQ ID NO:8. Transgenic plants are also meant to comprise progeny (descendant, offspring, etc.) of any generation of such a transgenic plant. A seed of any generation of all such transgenic insect-resistant plants wherein said seed comprises a DNA sequence encoding the polypeptide of the present invention is also an important aspect of the invention.

Insect resistant, crossed fertile transgenic plants comprising a transgene that encodes the polypeptide of SEQ ID NO:8 may be prepared by a method that generally involves obtaining a fertile transgenic plant that contains a chromosomally incorporated transgene encoding the insecticidal polypeptide of SEQ ID NO:8; operably linked to a promoter active in the plant; crossing the fertile transgenic plant with a second plant lacking the transgene to obtain a third plant comprising the transgene; and backcrossing the third plant to obtain a backcrossed fertile plant. In such cases, the transgene may be inherited through a male parent or through a female parent. The second plant may be an inbred, and the third plant may be a hybrid.

Likewise, an insect resistant hybrid, transgenic plant may be prepared by a method that generally involves crossing a first and a second inbred plant, wherein one or both of the first and second inbred plants comprises a chromosomally incorporated transgene that encodes the polypeptide of SEQ ID NO:8 operably linked to a plant expressible promoter that expresses the transgene. In illustrative embodiments, the first and second inbred plants may be monocot plants selected from the group consisting of: corn, wheat, rice, barley, oats, rye, sorghum, turfgrass and sugarcane.

In related embodiment, the invention also provides a method of preparing an insect resistant plant. The method generally involves contacting a recipient plant cell with a DNA composition comprising at least a first transgene that encodes the polypeptide of SEQ ID NO:8 under conditions permitting the uptake of the DNA composition; selecting a recipient cell comprising a chromosomally incorporated transgene that encodes the polypeptide; regenerating a plant from the selected cell; and identifying a fertile transgenic plant that has enhanced insect resistance relative to the corresponding non-transformed plant.

A method of producing transgenic seed generally involves obtaining a fertile transgenic plant comprising a chromosomally integrated transgene that encodes a polypeptide comprising the amino acid sequence of SEQ ID NO:8, operably linked to a promoter that expresses the transgene in a plant; and growing the plant under appropriate conditions to produce the transgenic seed.

A method of producing progeny of any generation of an insect resistance-enhanced fertile transgenic plant is also provided by the invention. The method generally involves collecting transgenic seed from a transgenic plant comprising a chromosomally integrated transgene that encodes the polypeptide of SEQ ID NO:8, operably linked to a promoter that expresses the transgene in the plant; planting the collected transgenic seed; and growing the progeny transgenic plants from the seed.

These methods for creating transgenic plants, progeny and seed may involve contacting the plant cell with the DNA composition using one of the processes well-known for plant cell transformation such as microprojectile bombardment, electroporation or *Agrobacterium*-mediated transformation.

An exemplary method disclosed herein provides for protecting a plant from cotton boll weevil infestation comprising providing to a boll weevil in its diet a plant transformed to express a protein toxic to said weevil wherein said protein is expressed in sufficient amounts to control boll weevil infestation and wherein said protein is selected from the group consisting of Cry22Aa, ET70, and tIC851. In a further embodiment of this method, a plant expressing two or more of these proteins for the purpose of reducing boll weevil infestation is contemplated, in particular for reducing the development of races of boll weevils resistant to any of these proteins.

These and other embodiments of the present invention will be apparent to those of skill in the art from the following examples and claims, having benefit of the teachings of the Specification herein.

2.1 tIC851 Polynucleotide Sequences

The present invention provides polynucleotide sequences that can be isolated from *Bacillus thuringiensis* strains, that are free from total genomic DNA, and that encode the novel insecticidal polypeptides and peptide fragments disclosed herein. The polynucleotides encoding these peptides and polypeptides may encode active insecticidal proteins, or peptide fragments, polypeptide subunits, functional domains, or the like of one or more tIC851 or tIC851-related crystal proteins, such as the polypeptide disclosed in SEQ ID NO:8. In addition the invention encompasses nucleic acid sequences which may be synthesized entirely in vitro using methods that are well-known to those of skill in the art which encode the novel tIC851 polypeptide, peptides, peptide fragments, subunits, or functional domains disclosed herein.

As used herein, the term "nucleic acid sequence" or "polynucleotide" refers to a nucleic acid molecule that has been isolated free of the total genomic DNA or otherwise of a particular species. Therefore, a nucleic acid sequence or polynucleotide encoding an endotoxin polypeptide refers to a nucleic acid molecule that comprises at least a first crystal protein-encoding sequence yet is isolated away from, or purified free from, total genomic DNA of the species from which the nucleic acid sequence is obtained, which in the instant case is the genome of the Gram-positive bacterial genus, *Bacillus*, and in particular, the species of *Bacillus* known as *B. thuringiensis*. Included within the term "nucleic acid sequence", are polynucleotide sequences and smaller fragments of such sequences, and also recombinant vectors, including, for example, plasmids, cosmids, phagemids, phage, virions, baculoviruses, artificial chromosomes, viruses, and the like. Accordingly, polynucleotide sequences that have between about 70% and about 80%, or more preferably between about 81% and about 90%, or even more preferably between about 91% and about 99% nucleic acid sequence identity or functional equivalence to the polynucleotide sequence of SEQ ID NO:7 will be sequences that are "essentially as set forth in SEQ ID NO:7." Highly preferred sequences are those which are preferably from about 91% to about 100% identical or functionally equivalent to the nucleotide sequence of SEQ ID NO:7. Other preferred sequences that encode tIC851- or tIC851-related sequences are those which are from about 81% to about 90% identical or functionally equivalent to the polynucleotide sequence set forth in SEQ ID NO:7. Likewise, sequences that are from about 71% to about 80% identical or functionally equivalent to the polynucleotide sequence set forth in SEQ ID NO:7 are also contemplated to be useful in the practice of the present invention.

Similarly, a polynucleotide comprising an isolated, purified, or selected gene or sequence region refers to a polynucleotide which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, or polypeptide-encoding unit. As will be understood by those in the art, this functional term includes both genomic sequences, operator sequences and smaller engineered gene segments that express, or may be adapted to express, proteins, polypeptides or peptides. In certain embodiments, a nucleic acid segment will comprise at least a first gene that encodes a polypeptide comprising the sequence of SEQ ID NO:8.

To permit expression of the gene, and translation of the mRNA into mature polypeptide, the nucleic acid sequence preferably also comprises at least a first promoter operably linked to the gene to express the insecticidal polypeptide in a host cell transformed with this nucleic acid sequence. The promoter may be an endogenous promoter, or alternatively, a heterologous promoter selected for its ability to promote expression of the gene in one or more particular cell types. For example, in the creation of transgenic plants and plant cells comprising a tIC851 gene, the heterologous promoter of choice is one that is plant-expressible, and in many instances, may preferably be a plant-expressible promoter that is tissue- or cell cycle-specific. The selection of plant-expressible promoters is well-known to those skilled in the art of plant transformation, and exemplary suitable promoters are described herein. In certain embodiments, the plant-expressible promoter may be selected from the group consisting of corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, Potato patatin, lectin, CaMV 35S, and the S-E9 small subunit RuBP carboxylase promoter.

"Isolated substantially away from other coding sequences" means that the gene of interest, in this case, a gene encoding a bacterial crystal protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

It will also be understood that this invention is not limited to the particular nucleic acid sequences which encode peptides of the present invention, or which encode the amino acid sequence of SEQ ID NO:8, including the DNA sequence which is particularly disclosed in SEQ ID NO:7.

Recombinant vectors and isolated DNA segments may therefore variously include the polypeptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA sequences of the present invention encompass biologically-functional, equivalent peptides. Such sequences may arise as a consequence of codon degeneracy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively). Recombinant vectors form further aspects of the present invention. Particularly useful vectors are contemplated to be those vectors in which the coding portion of the DNA sequence, whether encoding a full-length insecticidal protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein. In many cases, the promoter may be the native tIC851 promoter, or alternatively, a heterologous promoter, such as those of bacterial origin (including promoters from other crystal proteins), fungal origin, viral, phage or phagemid origin (including promoters such as CaMV35 and its derivatives, T3, T7, λ, and φ promoters and the like), or plant origin (including constitutive, inducible, and/or tissue-specific promoters and the like).

In other embodiments, it is contemplated that certain advantages will be gained by positioning the coding DNA sequence under the control of a recombinant, or heterologous, promoter. As used herein, a recombinant or heterologous promoter is intended to refer to a promoter that is not normally associated with a DNA sequence encoding a crystal protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA sequence, such as is advantageous in the large-scale production of recombinant proteins or peptides. Appropriate promoter systems contemplated for use in high-level expression include, but are not limited to, the *Pichia* expression vector system (Pharmacia LKB Biotechnology).

In yet another aspect, the present invention provides methods for producing a transgenic plant that expresses a selected nucleic acid sequence comprising a sequence region that encodes the novel endotoxin polypeptides of the present invention. The process of producing transgenic plants is well-known in the art. In general, the method comprises transforming a suitable plant host cell with a DNA sequence that contains a promoter operatively linked to a coding region that encodes one or more tIC851 polypeptides. Such a coding region is generally operatively linked to at least a first transcription-terminating region, whereby the promoter is capable of driving the transcription of the coding region in the cell, and hence providing the cell the ability to produce the polypeptide in vivo. Alternatively, in instances where it is desirable to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

Another aspect of the invention comprises transgenic plants which express a gene, gene sequence, or sequence region that encodes at least one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more transgenes, either native, synthetically modified, or mutated, that encodes an insecticidal polypeptide that is identical to, or highly homologous to the polypeptide disclosed in SEQ ID NO:8. In some instances, more than one transgene will be incorporated into the genome of the transformed host plant cell. Such is the case when more than one crystal protein-encoding DNA sequence is incorporated into the genome of such a plant. In certain situations, it may be desirable to have one, two, three, four, or even more *B. thuringiensis* crystal proteins (either native or recombinantly-engineered) incorporated and stably expressed in the transformed transgenic plant. Alternatively, a second transgene may be introduced into the plant cell to confer additional phenotypic traits to the plant. Such transgenes may confer resistance to one or more insects, bacteria, fungi, viruses, nematodes, or other pathogens.

A preferred gene which may be introduced includes, for example, a crystal protein-encoding DNA sequence from bacterial origin, and particularly one or more of those described herein which are obtained from *Bacillus* spp. Highly preferred nucleic acid sequences are those obtained from *B. thuringiensis*, or any of those sequences which have been genetically engineered to decrease or increase the insecticidal activity of the crystal protein in such a transformed host cell.

Means for transforming a plant cell and the preparation of plant cells, and regeneration of a transgenic cell line from a transformed cell, cell culture, embryo, or callus tissue are well-known in the art, and are discussed herein. Vectors, (including plasmids, cosmids, phage, phagemids, baculovirus, viruses, virions, BACs [bacterial artificial chromosomes], YACs [yeast artificial chromosomes]) comprising at least a first nucleic acid segment encoding an insecticidal polypeptide for use in transforming such cells will, of course, generally comprise either the operons, genes, or gene-derived sequences of the present invention, either native, or synthetically-derived, and particularly those encoding the disclosed crystal proteins. These nucleic acid constructs can further include structures such as promoters, enhancers, polylinkers, introns, terminators, or even gene sequences which have positively- or negatively-regulating activity upon the cloned δ-endotoxin gene as desired. The DNA sequence or gene may encode either a native or modified crystal protein, which will be expressed in the resultant recombinant cells, and/or which will confer to a transgenic plant comprising such a segment, an improved phenotype (in this case, increased resistance to insect attack, infestation, or colonization).

The preparation of a transgenic plant that comprises at least one polynucleotide sequence encoding a tIC851 or tIC851-derived polypeptide for the purpose of increasing or enhancing the resistance of such a plant to attack by a target insect represents an important aspect of the invention. In particular, the inventors describe herein the preparation of insect-resistant monocotyledonous or dicotyledonous plants, by incorporating into such a plant, a transgenic DNA sequence encoding at least one tIC851 polypeptide toxic to a coleopteran insect.

In a related aspect, the present invention also encompasses a seed produced by the transformed plant, a progeny from such seed, and a seed produced by the progeny of the original transgenic plant, produced in accordance with the above process. Such progeny and seeds will have a crystal protein-encoding transgene stably incorporated into their genome, and such progeny plants will inherit the traits afforded by the introduction of a stable transgene in Mendelian fashion. All such transgenic plants having incorporated into their genome transgenic DNA sequences encoding one or more tIC851 crystal proteins or polypeptides are aspects of this invention. As well-known to those of skill in the art, a progeny of a plant is understood to mean any offspring or any descendant from such a plant.

2.3 Definitions

The following words and phrases have the meanings set forth below.

A, an: In keeping with long-standing patent tradition, "a" or "an" used throughout this disclosure is intended to mean "one or more."

Comprising, comprises: In keeping with long-standing patent tradition, "comprising" and "comprises" used throughout this disclosure is intended to mean "including, but not limited to."

Expression: The combination of intracellular processes, including at least transcription and often the subsequent translation of mRNA of a coding DNA molecule such as a structural gene to produce a polypeptide.

Promoter: A recognition site on a DNA sequence or group of DNA sequences that provide an expression control element for a structural gene or sequence to be transcribed and to which an RNA-polymerase specifically binds and initiates RNA synthesis (transcription) of that gene or sequence to be transcribed.

Regeneration: The process of growing a plant from a plant cell (e.g., plant protoplast or explant).

Structural gene: A DNA sequence that encodes a messenger RNA which can be transcribed to produce a polypeptide.

Transformation: A process of introducing an exogenous DNA sequence (e.g., a vector, a recombinant DNA molecule) into a cell, protoplast, or organelle within a cell, in which that exogenous DNA is incorporated into DNA native to the cell, or is capable of autonomous replication within the cell.

Transformed cell: A cell whose genotype has been altered by the introduction of an exogenous DNA sequence into that cell.

Transgenic cell: Any cell derived from or regenerated from a transformed cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or a progeny of any generation of the plant that was derived from a transformed plant cell or protoplast, wherein the plant nucleic acids contains an exogenous selected nucleic acid sequence region not originally present in a native, non-transgenic plant of the same variety. The terms "transgenic plant" and "transformed plant" have sometimes been used in the art as synonymous terms to define a plant whose native DNA has been altered to contain a heterologous DNA molecule. However, it is thought more scientifically correct to refer to a regenerated plant or callus obtained from a transformed plant cell or protoplast cells as being a transgenic plant. Preferably, transgenic plants of the present invention include those plants that comprise at least a first selected polynucleotide that encodes an insecticidal polypeptide. This selected polynucleotide is preferably a δ-endotoxin coding region (or gene) operably linked to at least a first promoter that expresses the coding region to produce the insecticidal polypeptide in the transgenic plant. Preferably, the transgenic plants of the present invention that produce the encoded polypeptide demonstrate a phenotype of improved resistance to target insect pests. Such transgenic plants, their progeny, descendants, and seed from any such generation are preferably insect resistant plants.

Vector: A nucleic acid molecule capable of replication in a host cell and/or to which another nucleic acid sequence can be operably linked so as to bring about replication of the attached segment. Plasmids, phage, phagemids, and cosmids are all exemplary vectors. In many embodiments, vectors are used as a vehicle to introduce one or more selected polynucleotides into a host cell, thereby generating a "transformed" or "recombinant" host cell.

3.0 BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1 illustrates the nucleotide sequence and amino acid sequence translation of the tIC851 gene as derived from strains EG4135 and 4268.

FIG. 2 illustrates an amino acid sequence alignment of the related proteins CryET70 (SEQ ID NO: 2) and Cry22Aa (SEQ ID NO: 10), as well as the best fit alignment of tIC851 (SEQ ID NO: 8).

4.0 DESCRIPTION OF ILLUSTRATIVE EMBODIMENTS

4.1 Some Advantages of the Invention

The present invention provides a novel δ-endotoxin, designated tIC851, which is highly toxic to the cotton boll weevil, *Anthonomus grandis* Boheman. This protein has an amino acid sequence which is substantially unrelated to other δ-endotoxins that are toxic to coleopteran insects. The identification of Cry22Aa and CryET70 represented a new class of insecticidal crystal proteins. Unlike other WCRW toxic insecticidal crystal proteins from *B. thuringiensis*, CryET70 does not have significant toxicity to SCRW or CPB. The only known protein that is related to CryET70 is Cry22Aa, an insecticidal crystal protein that is reported to be toxic only to hymenopteran insects (GenBank Accession No. I34547). The inventors herein disclose a novel *Bacillus thuringiensis* δ-endotoxin displaying only insubstantial similarity to either CryET70 or to Cry22Aa, and displaying substantial differences in insecticidal spectrum and activity when compared to both of these proteins. The inventors also disclose that both CryET70 and Cry22Aa have significant toxicity to larvae of the cotton boll weevil.

4.2 Insect Pests

Almost all field crops, plants, and commercial farming areas are susceptible to attack by one or more insect pests. Particularly problematic coleopteran pests are identified in Table 1.

TABLE 1

TAXONOMY OF COLEOPTERAN PESTS IN THE SUBORDERS ARCHOSTEMATA AND POLYPHAGA

| Infraorder &/or Superfamily | Family | Subfamily | Tribe | Genus | Species |
|---|---|---|---|---|---|
| | Cupedidae (reticulated beetles) | | | *Priacma* | *P. serrata* |
| Bostrichiformia | Dermestidae (skin and larder beetles) | | | *Attagenus* | *A. pellio* |
| Chrysomeliformia | Cerambycidae (long-horned beetles) | | | *Agapanthia* | *Agapanthia* sp. |
| | | Lepturinae | | *Leptura* | *Leptura* sp. (flower long-horned beetle) |
| | | | | *Rhagium* | *Rhagium* sp. |
| | | | | *Megacyllene* | *M. robiniae* |
| | | Prioninae | | *Derobrachus* | *D. geminatus* |

TABLE 1-continued

TAXONOMY OF COLEOPTERAN PESTS IN THE SUBORDERS ARCHOSTEMATA AND POLYPHAGA

| | Family | Subfamily | Tribe | Genus | Species |
|---|---|---|---|---|---|
| Infraorder | Chrysomelidae (leaf beetles) | Chlamisinae | | Tetraopes | T. tetropthalmus |
| | | | | Exema | E. neglecta |
| | | Chrysomelinae | Chrysomelini | Chrysomela | C. tremula, Chrysomela sp. |
| | | | | Oreina | O. cacaliae |
| | | | Doryphorini | Chrysoline | Chrysolina sp. |
| | | | | Leptinotarsa | L. decemlineata (Colorado potato beetle) |
| | | | Gonioctenini | Gonioctena | G. fornicata, G. holdausi, G. intermedia, G. interposita, G. kamikawai, G. linnaeana, G. nigroplagiata, G. occidentalis, G. olivacea, G. pallida, G. quin-quepunctata, G. rubripennis, G. rufipes, G. tredecim-maculata, G. variabilis, G. viminalis |
| | | | Timarchini | Timarcha | Timarcha sp. |
| | | Criocerinae | | Oulema | Oulema sp. |
| | | Galerucinae | Galerucini | Monoxia | M. inornata, Monoxia sp. |
| | | | | Ophraella | O. arctica, O. artemisiae, O. bilineata, O. communa, O. conferta, O. cribrata, O. notata, O. notulata, O. nuda, O. pilosa, O. sexvittata, O. slobodkini |
| | | | Luperini | Cerotoma | C. trifurcata |
| | | | | Diabrotica | D. barberi (northern corn rootworm), D. undecimpunctata, (southern corn rootworm), D. virgifera (western corn rootworm) |
| | | unclassified Chrysomelidae | | Lachnaia | Lachnaia sp. |
| | | | | Epitrix | E. cucumeris (Harris) (potato flea beetle), E. fuscala (eggplant flea beetle) |
| | Curculionidae (weevils) | Curculioninae | | Anthonomus | A. grandis (boll weevil) |
| | | Entiminae | Naupactini | Aramigus | A. conirostris, A. globoculus, A. intermedius, A. planioculus, A. tesselatus |
| | | | | Otiorhynchus | Otiorhynchus sp. |
| | | | Phyllobiini | Diaprepes | D. abbreviata |
| | | | | Phyllobius | Phyllobius sp. |
| | | | | Galapaganus | G. galapagoensis |
| | | Hyperinae | | Hypera | H. brunneipennis (Egyptian alfalfa weevil), H. postica (alfalfa weevil), H. punctata (clover leaf weevil) |
| | | Molytinae | | Pissodes | P. affinis, P. nemorensis, P. schwarzi, P. strobi, P. terminalis |
| | | Rhynchophorinae | Sitophilini | Sitophilus | S. granarius (granary weevil), S. zeamais (maize weevil) |
| | Nemonychidae | | | Lebanorhinus | L. succinus |
| | Scolytidae | | | Ips | I. acuminatus, I. amitinus, I. cembrae, I. duplicatus, I. mannsfeldi, I. sexdentatus, I. typographus |
| | | | | Orthotomicus | O. erosus |
| | | | | Tomicus | T. minor |
| Cucujiformia | Coccinellidae (ladybird beetles) | | | Epilachna | E. borealis (squash ladybird beetle), E. varivstis (Mexican bean beetle) |
| | Cucujidae (flat bark beetles) | | | Cryptolestes | C. ferrugineus |
| | | | | Oryzaephilus (grain beetles) | O. surinamensis (saw-toothed grain beetle) |
| | Lagriidae (long-joined beetles) | | | Lagria | Lagria sp. |
| | Meloidae (blister beetles) | | | Epicauta | E. funebris |
| | | | | Meloe | M. proscarabaeus |
| | Rhipiphoridae | | | Rhipiphorus | R. fasciatus |
| | Tenebrionidae (darkling ground beetles) | | | Alphitobius | A. diaperinus (lesser mealworm) |
| | | | | Hegeter | H. amaroides, H. brevicollis, H. costipennis, H. fernandezi, H. glaber, H. gomerensis, H. gran-canariensis, H. impressus, H. intercedens, H. lateralis, |

TABLE 1-continued

TAXONOMY OF COLEOPTERAN PESTS IN THE SUBORDERS ARCHOSTEMATA AND POLYPHAGA

| Family | Subfamily | Tribe | Genus | Species |
|---|---|---|---|---|
| | | | | *H. plicifrons, H. politus, H. subrotundatus, H. tenui-punctatus, H. transversus, H. webbianus* |
| | | | Misolampus | *M. goudoti* |
| | | | Palorus | *P. ficicola, P. ratzeburgi* (small-eyed flour beetle), *P. subdepressus* (depressed flour beetle) |
| | | | Pimelia | *P. baetica, P. canariensis, P. criba, P. elevata, P. estevezi, P. fernan-dezlopezi, P. grandis, P. granulicollis, P. integra, P. interjecta, P. laevigata, P. lutaria, P. radula, P. sparsa, P. variolosa* |
| | | | Tenebrio | *T. molitor* (yellow mealworm), *T. obscurus* (dark mealworm) |
| | | | Tentyria | *T. schaumi* |
| | | | Tribolium | *T. brevicornis, T. castaneum* (red flour beetle), *T. confusum* (confused flour beetle), *T. freemani, T. madens* |
| | | | Zophobas | *Z. atratus* |
| | | | | *Z. rugipes* |
| Elateriformia - Superfamily Elateroidea | | | Octinodes | *Octinodes* sp. |
| | | | Pyrophorus | *P. plagio-phthalamus* |
| Scarabaeiformia | Lucanidae (Stag beetles) | | Dorcus | *D. parallelo-pipedus* |
| | | | Lucanus | *L. cervus* |
| | Scarabaeidae (lamellicorn beetles) | | Allomyrina | *A. dichotoma* |
| | | Cetoniinae (flower beetle) | Pachnoda | *P. marginata* |
| | | Dynastinae | Xyloryctes | *X. faunus* |
| | | Geotrupinae (earth-boring dung beetles) | Geotrupes | *G. stercorosus* |
| | | Melonlonthinae (chafers) | Costelytra | *C. zealandica* |
| | | | Holotrichia | *H. diomphalia* |
| | | | Melolontha | *M. melolontha* (cockchafer) |
| | | | Odontria | *O. striata* |
| | | | | *O. variegata* |
| | | | Prodontria | *P. bicolorata, P. capito, P. lewisi, P. tarsis, P. modesta, P. pinguis, P. praelatella, P. truncata, Prodontria* sp. |
| | | | Scythrodes | *S. squalidus* |
| | | Rutelinae (shining leaf chafers) | Popillia | *P. japonica* (Japanese beetle) |
| | | Scarabaeinae | Copris | *C. lunaris* (black dung beetle) |
| | | | Scarabaeus | *Scarabaeus* sp. (scarab) |
| Staphyliniformia | Hydrophilidae | | Cercyon | *Cercyon* sp. |
| | Silphidae | | Nicrophorus | *N. americanus, N. marginatus, N. orbicollis, N. tomentosus* |
| | Staphylinidae (rove beetles) | | Carpelimus | *Carpelimus* sp. |
| | | | Quedius | *Q. mesomelinus* |
| | | | Tachyporus | *Tachyporus* sp. |
| | | | Xantholinus | *Xantholinus* sp. |

4.3 Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected crystal protein-encoding gene sequence, e.g., a sequence such as that shown in SEQ ID NO:8 (tIC851), SEQ ID NO:10 (Cry22Aa), and SEQ ID NO:2 (CryET70). The ability of such DNAs and nucleic acid probes to specifically hybridize to a crystal protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a crystal protein gene from *B. thuringiensis* using thermal amplification technology. Sequences of related crystal protein genes from other species may also be amplified using such primers.

To provide certain of the advantages in accordance with the present invention, a preferred nucleic acid sequence employed for hybridization studies or assays includes sequences that are complementary to at least an about 23 to about 40 or so long nucleotide stretch of a crystal protein-encoding sequence, such as that shown in SEQ ID NO:7 (tIC851), SEQ ID NO:9 (cry22Aa), or SEQ ID NO:1 (cryET70). A size of at least about 14 or 15 or so nucleotides in length helps to ensure that the fragment will be of sufficient length to form a duplex molecule that is both stable and selective. Molecules having complementary sequences over stretches greater than about 23 or so bases in length are generally preferred, though, in order to increase stability and selectivity of the hybrid, and thereby improve the quality and degree of specific hybrid molecules obtained. One will generally prefer to design nucleic acid molecules having gene-complementary stretches of about 14 to about 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, specifically incorporated herein by reference, or by excising selected DNA fragments from recombinant plasmids containing appropriate inserts and suitable restriction sites.

4.4 Expression Vectors

The present invention contemplates a polynucleotide of the present invention comprised within one or more expression vectors. Thus, in one embodiment an expression vector comprises a nucleic acid segment containing a tIC851 gene operably linked to a promoter which expresses the gene. Additionally, the coding region may also be operably linked to a transcription-terminating region, whereby the promoter drives the transcription of the coding region, and the transcription-terminating region halts transcription at some point 3′ of the coding region.

As used herein, the term "operatively linked" means that a promoter is connected to an coding region in such a way that the transcription of that coding region is controlled and regulated by that promoter. Means for operatively linking a promoter to a coding region are well known in the art.

In a preferred embodiment, the recombinant expression of DNAs encoding the crystal proteins of the present invention is preferable in a *Bacillus* host cell. Preferred host cells include *B. thuringiensis*, *B. megaterium*, *B. subtilis*, and related bacilli, with *B. thuringiensis* host cells being highly preferred. Promoters that function in bacteria are well-known in the art. An exemplary and preferred promoter for the *Bacillus*-derived crystal proteins include any of the known crystal protein gene promoters, including the tIC851 gene promoter itself. Alternatively, mutagenized or recombinant promoters may be engineered by the hand of man and used to promote expression of the novel gene segments disclosed herein.

In an alternate embodiment, the recombinant expression of DNAs encoding the crystal proteins of the present invention is performed using a transformed Gram-negative bacterium such as an *E. coli* or *Pseudomonas* spp. host cell. Promoters which function in high-level expression of target polypeptides in *E. coli* and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Lel) that is only expressed during seed maturation and accounts for about 2 to about 5% of total seed mRNA. The lectin gene and seed storage protein specific promoter have been fully characterized and used to direct seed specific expression in transgenic tobacco plants (Vodkin et al., 1983; Lindstrom et al., 1990.)

An expression vector containing a coding region that encodes a polypeptide of interest is engineered to be under control of the lectin promoter and that vector is introduced into plants using, for example, a protoplast transformation method (Dhir et al., 1991a). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose, synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35S transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are specifically incorporated herein by reference in their entirety. Those vectors can be modified to include a coding sequence in accordance with the present invention.

A variety of methods have been developed to operatively insert a DNA sequence into a vector via complementary cohesive termini or blunt ends. For instance, complementary homopolymer tracts can be added to the DNA sequence to be inserted and to the vector DNA. The vector and DNA sequence are then joined by hydrogen bonding between the complementary homopolymeric tails to form recombinant DNA molecules.

A coding region that encodes a polypeptide having the ability to confer insecticidal activity to a cell is preferably a tIC851 B. thuringiensis crystal protein-encoding gene. In preferred embodiments, such a polypeptide has the amino acid residue sequence of SEQ ID NO:8, or a functional equivalent thereof. In accordance with such embodiments, a coding region comprising the DNA sequence of SEQ ID NO:7 is also preferred.

4.5 Characteristic of the tIC851 Polypeptide Isolated from EG4135

The present invention provides a novel polypeptide that defines a whole or a portion of a B. thuringiensis tIC851 crystal protein.

In a preferred embodiment, the invention discloses and claims an isolated and purified tIC851 protein. The tIC851 protein isolated from EG4135 comprises a 632 amino acid sequence, and has a calculated molecular mass of approximately 69,527 Da. tIC851 has a calculated isoelectric constant (pI) equal to 5.80. The amino acid composition of the tIC851 protein is given in Table 2.

TABLE 2

AMINO ACID COMPOSITION OF tIC851

| Amino Acid | # Residues | % Total | Amino Acid | # Residues | % Total |
|---|---|---|---|---|---|
| Ala | 45 | 7.1 | Leu | 29 | 4.6 |
| Arg | 13 | 2.1 | Lys | 51 | 8.1 |
| Asn | 40 | 6.3 | Met | 5 | 0.8 |

TABLE 2-continued

AMINO ACID COMPOSITION OF tIC851

| Amino Acid | # Residues | % Total | Amino Acid | # Residues | % Total |
|---|---|---|---|---|---|
| Asp | 49 | 7.8 | Phe | 22 | 3.5 |
| Cys | 1 | 0.2 | Pro | 34 | 5.4 |
| Gln | 13 | 2.1 | Ser | 34 | 5.4 |
| Glu | 41 | 6.5 | Thr | 57 | 9.0 |
| Gly | 47 | 7.4 | Tro | 8 | 1.3 |
| His | 12 | 1.9 | Tyr | 25 | 3.9 |
| Ile | 62 | 9.8 | Val | 44 | 6.9 |
| Acidic | (Asp + Glu) | | | 90 | 14 |
| Basic | (Arg + Lys) | | | 64 | 10 |
| Aromatic | (Phe + Trp + Tyr) | | | 55 | 9 |
| Hydrophobic | (Aromatic + Ile + Leu + Met + Val) | | | 195 | 31 |

4.6 Nomenclature of the Novel Proteins

The inventors have arbitrarily assigned the designation tIC851 to the novel protein of the invention. Likewise, the arbitrary designation of tIC851 has been assigned to the novel nucleic acid sequence which encodes this polypeptide. Formal assignment of gene and protein designations based on the revised nomenclature of crystal protein endotoxins will be assigned by a committee on the nomenclature of B. thuringiensis, formed to systematically classify B. thuringiensis crystal proteins. The inventors contemplate that the arbitrarily assigned designations of the present invention will be superseded by the official nomenclature assigned to these sequences, and that based on the lack of identity or substantial similarity to other known insecticidal protein isolated from Bacillus thuringiensis, the tIC851 protein will be alone in a separate category and class of proteins.

4.7 Transformed Host Cells and Transgenic Plants

Methods and compositions for transforming a bacterium, a yeast cell, a plant cell, or an entire plant with one or more expression vectors comprising a crystal protein-encoding gene sequence are further aspects of this disclosure. A transgenic bacterium, yeast cell, plant cell or plant derived from such a transformation process or the progeny and seeds from such a transgenic plant are also further embodiments of the invention.

Means for transforming bacteria and yeast cells are well known in the art. Typically, means of transformation are similar to those well known means used to transform other bacteria or yeast such as E. coli or Saccharomyces cerevisiae. Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain. Suitable methods for introducing transforming DNA into a cell consist of but are not limited to Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253) and the gene gun (Johnston and Tang, 1994; Fynan et al., 1993); (3) viral vectors (Clapp, 1993; Lu et al., 1993; Eglitis and Anderson, 1988; Eglitis et al., 1988); and (4) receptor-mediated mechanisms (Curiel et al., 1991; 1992; Wagner et al., 1992).

4.7.1 Microprojectile Bombardment

A particularly advantageous method for delivering transforming DNA sequences into plant cells is microprojectile bombardment. In this method, particles may be coated with nucleic acids and delivered into cells by a propelling force. Exemplary particles include those comprised of tungsten, gold, platinum, and the like.

4.7.2 *Agrobacterium*-Mediated Transfer

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

4.7.3 Gene Expression in Plants

To overcome limitations in foreign gene expression in plants, particular sequences and signals in RNAs that have the potential for having a specific effect on RNA stability have been identified. In certain embodiments of the invention, therefore, there is a desire to optimize expression of the disclosed nucleic acid segments in planta. One particular method of doing so, is by alteration of the bacterial gene to remove sequences or motifs which decrease expression in a transformed plant cell. The process of engineering a coding sequence for optimal expression in planta is often referred to as "plantizing" a DNA sequence.

Particularly problematic sequences are those which are A+T rich. Unfortunately, since *B. thuringiensis* has an A+T rich genome, native crystal protein gene sequences must often be modified for optimal expression in a plant. The sequence motif ATTTA (or AUUUA as it appears in RNA) has been implicated as a destabilizing sequence in mammalian cell mRNA (Shaw and Kamen, 1986). Many short lived mRNAs have A+T rich 3' untranslated regions, and these regions often have the ATTTA sequence, sometimes present in multiple copies or as multimers (e.g., ATTTATTTA . . . ). Shaw and Kamen showed that the transfer of the 3' end of an unstable mRNA to a stable RNA (globin or VA1) decreased the stable RNA's half life dramatically. They further showed that a pentamer of ATTTA had a profound destabilizing effect on a stable message, and that this signal could exert its effect whether it was located at the 3' end or within the coding sequence. However, the number of ATTTA sequences and/or the sequence context in which they occur also appear to be important in determining whether they function as destabilizing sequences Shaw and Kamen showed that a trimer of ATTTA had much less effect than a pentamer on mRNA stability and a dimer or a monomer had no effect on stability (Shaw and Kamen, 1987). Note that multimers of ATTTA such as a pentamer automatically create an A+T rich region. This was shown to be a cytoplasmic effect, not nuclear. In other unstable mRNAs, the ATTTA sequence may be present in only a single copy, but it is often contained in an A+T rich region. From the animal cell data collected to date, it appears that ATTTA at least in some contexts is important in stability, but it is not yet possible to predict which occurrences of ATTTA are destabilizing elements or whether any of these effects are likely to be seen in plants. Table 3 lists some of the more common AT rich sequences identified as problematic when present in a coding sequence for which high levels of expression are desired.

The addition of a polyadenylate string to the 3' end is common to most eukaryotic mRNAs, both plant and animal. The currently accepted view of polyA addition is that the nascent transcript extends beyond the mature 3' terminus. Contained within this transcript are signals for polyadenylation and proper 3' end formation. This processing at the 3' end involves cleavage of the mRNA and addition of polyA to the mature 3' end. By searching for consensus sequences near the polyA tract in both plant and animal mRNAs, it has been possible to identify consensus sequences that apparently are involved in polyA addition and 3' end cleavage. The same consensus sequences seem to be important to both of these processes. These signals are typically a variation on the sequence AATAAA. In animal cells, some variants of this sequence that are functional have been identified; in plant cells there seems to be an extended range of functional sequences (Wickens and Stephenson, 1984; Dean et al., 1986). Because all of these consensus sequences are variations on AATAAA, they all are A+T rich sequences.

TABLE 3

POLYADENYLATION SITES IN PLANT GENES

| | | |
|---|---|---|
| PA | AATAAA | Major consensus site |
| P1A | AATAAT | Major plant site |
| P2A | AACCAA | Minor plant site |

TABLE 3-continued

POLYADENYLATION SITES IN PLANT GENES

| P3A | ATATAA | " |
|---|---|---|
| P4A | AATCAA | " |
| P5A | ATACTA | " |
| P6A | ATAAAA | " |
| P7A | ATGAAA | " |
| P8A | AAGCAT | " |
| P9A | ATTAAT | " |
| P10A | ATACAT | " |
| P11A | AAAATA | " |
| P12A | ATTAAA | Minor animal site |
| P13A | AATTAA | " |
| P14A | AATACA | " |
| P15A | CATAAA | " |

The present invention provides a method for preparing synthetic plant genes which genes express their protein product at levels significantly higher than the wild-type genes which were commonly employed in plant transformation heretofore. In another aspect, the present invention also provides novel synthetic plant genes which encode non-plant proteins.

As described above, the expression of native *B. thuringiensis* genes in plants is often problematic. The nature of the coding sequences of *B. thuringiensis* genes distinguishes them from plant genes as well as many other heterologous genes expressed in plants. In particular, *B. thuringiensis* genes are very rich (~62%) in adenine (A) and thymine (T) while plant genes and most other bacterial genes which have been expressed in plants are on the order of 45–55% A+T.

Due to the degeneracy of the genetic code and the limited number of codon choices for any amino acid, most of the "excess" A+T of the structural coding sequences of some *Bacillus* species are found in the third position of the codons. That is, genes of some *Bacillus* species have A or T as the third nucleotide in many codons. Thus A+T content in part can determine codon usage bias. In addition, it is clear that genes evolve for maximum function in the organism in which they evolve. This means that particular nucleotide sequences found in a gene from one organism, where they may play no role except to code for a particular stretch of amino acids, have the potential to be recognized as gene control elements in another organism (such as transcriptional promoters or terminators, polyA addition sites, intron splice sites, or specific mRNA degradation signals). It is perhaps surprising that such misread signals are not a more common feature of heterologous gene expression, but this can be explained in part by the relatively homogeneous A+T content (~50%) of many organisms. This A+T content plus the nature of the genetic code put clear constraints on the likelihood of occurrence of any particular oligonucleotide sequence. Thus, a gene from *E. coli* with a 50% A+T content is much less likely to contain any particular A+T rich segment than a gene from *B. thuringiensis*.

Typically, to obtain high-level expression of the δ-endotoxin genes in plants, existing structural coding sequence ("structural gene") which codes for the δ-endotoxin are modified by removal of ATTTA sequences and putative polyadenylation signals by site directed mutagenesis of the DNA comprising the structural gene. It is most preferred that substantially all the polyadenylation signals and ATTTA sequences are removed although enhanced expression levels are observed with only partial removal of either of the above identified sequences. Alternately if a synthetic gene is prepared which codes for the expression of the subject protein, codons are selected to avoid the ATTTA sequence and putative polyadenylation signals. For purposes of the present invention putative polyadenylation signals include, but are not necessarily limited to, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA. In replacing the ATTTA sequences and polyadenylation signals, codons are preferably utilized which avoid the codons which are rarely found in plant genomes.

The selected DNA sequence is scanned to identify regions with greater than four consecutive adenine (A) or thymine (T) nucleotides. The A+T regions are scanned for potential plant polyadenylation signals. Although the absence of five or more consecutive A or T nucleotides eliminates most plant polyadenylation signals, if there are more than one of the minor polyadenylation signals identified within ten nucleotides of each other, then the nucleotide sequence of this region is preferably altered to remove these signals while maintaining the original encoded amino acid sequence.

The second step is to consider the about 15 to about 30 or so nucleotide residues surrounding the A+T rich region identified in step one. If the A+T content of the surrounding region is less than 80%, the region should be examined for polyadenylation signals. Alteration of the region based on polyadenylation signals is dependent upon (1) the number of polyadenylation signals present and (2) presence of a major plant polyadenylation signal.

The extended region is examined for the presence of plant polyadenylation signals. The polyadenylation signals are removed by site-directed mutagenesis of the DNA sequence. The extended region is also examined for multiple copies of the ATTTA sequence which are also removed by mutagenesis.

It is also preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

4.7.4 Synthetic Oligonucleotides for Mutagenesis

When oligonucleotides are used in the mutagenesis, it is desirable to maintain the proper amino acid sequence and reading frame, without introducing common restriction sites such as BglII, HindIII, SacI, KpnI, EcoRI, NcoI, PstI and SalI into the modified gene. These restriction sites are found in poly-linker insertion sites of many cloning vectors. Of course, the introduction of new polyadenylation signals, ATTTA sequences or consecutive stretches of more than five A+T or G+C, should also be avoided. The preferred size for the oligonucleotides is about 40 to about 50 bases, but fragments ranging from about 18 to about 100 bases have been utilized. In most cases, a minimum of about 5 to about 8 base pairs of homology to the template DNA on both ends of the synthesized fragment are maintained to insure proper hybridization of the primer to the template. The oligonucleotides should avoid sequences longer than five base pairs A+T or G+C. Codons used in the replacement of wild-type codons should preferably avoid the TA or CG doublet wherever possible. Codons are selected from a plant preferred codon table (such as Table 4 below) so as to avoid codons which are rarely found in plant genomes, and efforts should be made to select codons to preferably adjust the G+C content to about 50%.

TABLE 4

PREFERRED CODON USAGE IN PLANTS

| Amino Acid | Codon | Percent Usage in Plants |
|---|---|---|
| ARG | CGA | 7 |
|  | CGC | 11 |
|  | CGG | 5 |
|  | CGU | 25 |
|  | AGA | 29 |
|  | AGG | 23 |
| LEU | CUA | 8 |
|  | CUC | 20 |
|  | CUG | 10 |
|  | CUU | 28 |
|  | UUA | 5 |
|  | UUG | 30 |
| SER | UCA | 14 |
|  | UCC | 26 |
|  | UCG | 3 |
|  | UCU | 21 |
|  | AGC | 21 |
|  | AGU | 15 |
| THR | ACA | 21 |
|  | ACC | 41 |
|  | ACG | 7 |
|  | ACU | 31 |
| PRO | CCA | 45 |
|  | CCC | 19 |
|  | CCG | 9 |
|  | CCU | 26 |
| ALA | GCA | 23 |
|  | GCC | 32 |
|  | GCG | 3 |
|  | GCU | 41 |
| GLY | GGA | 32 |
|  | GGC | 20 |
|  | GGG | 11 |
|  | GGU | 37 |
| ILE | AUA | 12 |
|  | AUC | 45 |
|  | AUU | 43 |
| VAL | GUA | 9 |
|  | GUC | 20 |
|  | GUG | 28 |
|  | GUU | 43 |
| LYS | AAA | 36 |
|  | AAG | 64 |
| ASN | AAC | 72 |
|  | AAU | 28 |

TABLE 4-continued

PREFERRED CODON USAGE IN PLANTS

| Amino Acid | Codon | Percent Usage in Plants |
|---|---|---|
| GLN | CAA | 64 |
|  | CAG | 36 |
| HIS | CAC | 65 |
|  | CAU | 35 |
| GLU | GAA | 48 |
|  | GAG | 52 |
| ASP | GAC | 48 |
|  | GAU | 52 |
| TYR | UAC | 68 |
|  | UAU | 32 |
| CYS | UGC | 78 |
|  | UGU | 22 |
| PHE | UUC | 56 |
|  | UUU | 44 |
| MET | AUG | 100 |
| TRP | UGG | 100 |

Regions with many consecutive A+T bases or G+C bases are predicted to have a higher likelihood to form hairpin structures due to self-complementarity. Disruption of these regions by the insertion of heterogeneous base pairs is preferred and should reduce the likelihood of the formation of self-complementary secondary structures such as hairpins which are known in some organisms to inhibit transcription (transcriptional terminators) and translation (attenuators).

Alternatively, a completely synthetic gene for a given amino acid sequence can be prepared, with regions of five or more consecutive A+T or G+C nucleotides being avoided. Codons are selected avoiding the TA and CG doublets in codons whenever possible. Codon usage can be normalized against a plant preferred codon usage table (such as Table 4) and the G+C content preferably adjusted to about 50%. The resulting sequence should be examined to ensure that there are minimal putative plant polyadenylation signals and ATTTA sequences. Restriction sites found in commonly used cloning vectors are also preferably avoided. However, placement of several unique restriction sites throughout the gene is useful for analysis of gene expression or construction of gene variants.

4.8 Methods for Producing Insect-Resistant Transgenic Plants

By transforming a suitable host cell, such as a plant cell, with a recombinant tIC851 gene sequence, the expression of the encoded crystal protein (i.e. a bacterial crystal protein or polypeptide having insecticidal activity against Coleopterans) can result in the formation of insect-resistant plants.

A transgenic plant of this invention thus has an increased amount of a coding region (e.g., a gene) that encodes a polypeptide in accordance with SEQ ID NO:8. A preferred transgenic plant is an independent segregant and can transmit that gene and its activity to its progeny. A more preferred transgenic plant is homozygous for that gene, and transmits that gene to all of its offspring upon sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against coleopteran insects, preferably in the field, under a range of environmental conditions.

Transgenic plants comprising one or more transgenes that encode a polypeptide in accordance with SEQ ID NO:8 will preferably exhibit a phenotype of improved or enhanced insect resistance to the target coleopteran insects as described herein. These plants will preferably provide transgenic seeds, which will be used to create lineages of transgenic plants (i.e. progeny or advanced generations of the original transgenic plant) that may be used to produce seed, or used as animal or human foodstuffs, or to produce fibers, oil, fruit, grains, or other commercially-important plant products or plant-derived components. In such instances, the progeny and seed obtained from any generation of the transformed plants will contain the selected and stably integrated transgene that encodes the δ-endotoxin of the present invention. The transgenic plants of the present invention may be crossed to produce hybrid or inbred lines with one or more plants that have desirable properties. In certain circumstances, it may also be desirable to create transgenic plants, seed, and progeny that contain one or more additional transgenes incorporated into their genome in addition to the transgene encoding the polypeptide of the invention. For example, the transgenic plants may contain a second gene encoding the same, or a different insect-resistance polypeptide, or alternatively, the plants may comprise one or more additional transgenes such as those conferring herbicide resistance, fungal resistance, bacterial resistance, stress, salt, or drought tolerance, improved stalk or root lodging, increased starch, grain, oil, carbohydrate, amino acid, protein production, and the like.

4.9 Isolating Homologous Gene and Gene Fragments

The genes and Sendotoxins according to the subject invention include not only the full length sequences disclosed herein but also fragments of these sequences, or fusion proteins, which retain the characteristic insecticidal activity of the sequences specifically exemplified herein.

It should be apparent to a person skill in this art that insecticidal δ-endotoxins can be identified and obtained through several means. The specific genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. Also, genes which code for active fragments may be obtained using a variety of other restriction enzymes. Proteases may be used to directly obtain active fragments of these δ-endotoxins.

Equivalent δ-endotoxins and/or genes encoding these equivalent δ-endotoxins can also be isolated from *Bacillus* strains and/or DNA libraries using the teachings provided herein. For example, antibodies to the Sendotoxins disclosed and claimed herein can be used to identify and isolate other δ-endotoxins from a mixture of proteins. Specifically, antibodies may be raised to the portions of the δ-endotoxins which are most constant and most distinct from other *B. thuringiensis* δ-endotoxins. These antibodies can then be used to specifically identify equivalent δ-endotoxins with the characteristic insecticidal activity by immunoprecipitation, enzyme linked immunoassay (ELISA), or Western blotting.

A further method for identifying the δ-endotoxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying formicidal δ-endotoxin genes of the subject invention.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the *B. thuringiensis* δ-endotoxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein which do not alter the protein secondary structure, or if the structure is altered, the biological activity is substantially retained. Further, the invention also includes mutants of organisms hosting all or part of a δ-endotoxin encoding a gene of the invention. Such mutants can be made by techniques well known to persons skilled in the art. For example, UV irradiation can be used to prepare mutants of host organisms. Likewise, such mutants may include asporogenous host cells which also can be prepared by procedures well known in the art.

4.10 Recombinant Host Cells

The nucleotide sequences of the subject invention may be introduced into a wide variety of microbial and eukaryotic hosts. As hosts for recombinant expression of tIC851 polypeptides, of particular interest will be the prokaryotes and the lower eukaryotes, such as fungi. Illustrative prokaryotes, both Gram-negative and Gram-positive, include Enterobacteriaceae, such as *Escherichia, Erwinia, Shigella, Salmonella,* and *Proteus*; Bacillaceae; Rhizobiceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae, Actinomycetales, and Nitrobacteraceae. Among eukaryotes are fungi, such as

*Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Characteristics of particular interest in selecting a host cell for purposes of production include ease of introducing the genetic constructs of the present invention into the host cell, availability of expression systems, efficiency of expression, stability of the gene of interest in the host, and the presence of auxiliary genetic capabilities.

A large number of microorganisms known to inhabit the phylloplane (the surface of the plant leaves) and/or the rhizosphere (the soil surrounding plant roots) of a wide variety of important crops may also be desirable host cells for manipulation, propagation, storage, delivery and/or mutagenesis of the disclosed genetic constructs. These microorganisms include bacteria, algae, and fungi. Of particular interest are microorganisms, such as bacteria, e.g., genera *Bacillus* (including the species and subspecies *B. thuringiensis kurstaki* HD-1, *B. thuringiensis kurstaki* HD-73, *B. thuringiensis sotto, B. thuringiensis berliner, B. thuringiensis thuringiensis, B. thuringiensis tolworthi, B. thuringiensis dendrolimus, B. thuringiensis alesti, B. thuringiensis galleriae, B. thuringiensis aizawai, B. thuringiensis subtoxicus, B. thuringiensis entomocidus, B. thuringiensis tenebrionis* and *B. thuringiensis* san diego); *Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodobacter sphaeroides, Xanthomonas campestris, Rhizobium melioti, Alcaligenes eutrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*.

Characteristics of particular interest in selecting a host cell for purposes of production include ease of introducing a selected genetic construct into the host, availability of expression systems, efficiency of expression, stability of the polynucleotide in the host, and the presence of auxiliary genetic capabilities. Other considerations include ease of formulation and handling, economics, storage stability, and the like.

4.11 Polynucleotide Sequences

DNA compositions encoding the insecticidally-active polypeptides of the present invention are particularly preferred for delivery to recipient plant cells, and ultimately in the production of insect-resistant transgenic plants. For example, DNA segments in the form of vectors and plasmids, or linear DNA fragments, in some instances containing only the DNA element to be expressed in the plant cell, and the like, may be employed.

4.12 Methods for Preparing Mutagenized Polynucleotide Sequences

In certain circumstances, it may be desirable to modify or alter one or more nucleotides in one or more of the polynucleotide sequences disclosed herein for the purpose of altering or changing the insecticidal activity or insecticidal specificity of the encoded polypeptide. In general, the means and methods for mutagenizing a DNA sequences are well-known to those of skill in the art. Modifications to such sequences may be made by random, or site-specific mutagenesis procedures. The polynucleotides may be modified by the addition, deletion, or substitution of one or more nucleotides from the sequence encoding the insecticidally-active polypeptide.

Mutagenesis may be performed in accordance with any of the techniques known in the art such as and not limited to synthesizing an oligonucleotide having one or more mutations within the sequence of a particular region. In particular, site-specific mutagenesis is a technique useful in the preparation of mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

The preparation of sequence variants of the selected δ-endotoxin-encoding DNA segments using site-directed mutagenesis is provided as a means of producing potentially useful species and is not meant to be limiting as there are other ways in which sequence variants of DNA sequences may be obtained. For example, recombinant vectors encoding the desired sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224.

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159. Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

4.13 Post-Transcriptional Events Affecting Expression of Transgenes in Plants

In many instances, the level of transcription of a particular transgene in a given host cell is not always indicative of the amount of protein being produced in the transformed host cell. This is often due to post-transcriptional processes, such as splicing, polyadenylation, appropriate translation initiation, and RNA stability, that affect the ability of a transcript to produce protein. Such factors may also affect the stability and amount of mRNA produced from the given transgene. As such, it is often desirable to alter the post-translational events through particular molecular biology techniques. The inventors contemplate that in certain instances it may be desirable to alter the transcription and/or expression of the polypeptide-encoding nucleic acid constructs of the present invention to increase, decrease, or otherwise regulate or control these constructs in particular host cells and/or transgenic plants.

4.13.1 Efficient Initiation of Protein Translation

The 5'-untranslated leader (5'-UTL) sequence of eukaryotic mRNA plays a major role in translational efficiency. Many early chimeric transgenes using a viral promoter used an arbitrary length of viral sequence after the transcription initiation site and fused this to the AUG of the coding region. More recently studies have shown that the 5'-UTL sequence and the sequences directly surrounding the AUG can have a large effect in translational efficiency in host cells and particularly certain plant species and that this effect can be different depending on the particular cells or tissues in which the message is expressed.

In most eukaryotic mRNAs, the point of translational initiation occurs at the AUG codon closest to the 5' cap of the transcript. Comparison of plant mRNA sequences and site directed mutagenesis experiments have demonstrated the existence of a consensus sequence surrounding the initiation codon in plants, 5'-UAAACA<u>AUG</u>GCU-3' (SEQ ID NO:4) (Joshi, 1987; Lutcke et al., 1987). However, consensus sequences will be apparent amongst individual plant species. For example, a compilation of sequences surrounding the initiation codon from 85 maize genes yields a consensus of 5'-(C/G)<u>AUG</u>GCG-3' (Luehrsen et al., 1994). In tobacco protoplasts, transgenes encoding β-glucuronidase (GUS) and bacterial chitinase showed a 4-fold and an 8-fold increase in expression, respectively, when the native sequences of these genes were changed to encode 5'-ACC <u>AUG</u>G-3' (Gallie et al., 1987b; Jones et al., 1988). Interestingly, B. thuringiensis has chosen to utilize an alternative initiation codon for the native gene encoding tIC851. The inventors find, as described below, that this codon, although not generally known to encode for other than leucine, is believed to code for methionine in the first position of the tIC851 polypeptide toxin as judged by N-terminal amino acid sequence analysis of the purified toxin. Therefore, for efficiency inplanta, it is intended that the more frequently utilized ATG initiation codon will be used instead.

When producing chimeric transgenes (i.e. transgenes comprising DNA segments from different sources operably linked together), often the 5'-UTL of plant viruses are used. The alfalfa mosaic virus (AMV) coat protein and brome mosaic virus (BMV) coat protein 5-UTLs have been shown to enhance mRNA translation 8-fold in electroporated tobacco protoplasts (Gallie et al., 1987a; 1987b). A 67-nucleotide derivative (Ω) of the 5'-UTL of tobacco mosaic virus RNA (TMV) fused to the chloramphenicol acetyltransferase (CAT) gene and GUS gene has been shown to enhance translation of reporter genes in vitro (Gallie et al., 1987a; 1987b; Sleat et al., 1987; Sleat et al., 1988). Electroporation of tobacco mesophyllprotoplasts with transcripts containing the TMV leader fused to reporter genes CAT, GUS, and LUC produced a 33-, 21-, and 36-fold level of enhancement, respectively (Gallie et al., 1987a; 1987b; Gallie et al., 1991). Also in tobacco, an 83-nt 5'-UTL of potato virus X RNA was shown to enhance expression of the neomycin phosphotransferese II (NptII) 4-fold (Poogin and Skryabin, 1992).

The effect of a 5'-UTL may be different depending on the plant, particularly between dicots and monocots. The TMV 5'-UTL has been shown to be more effective in tobacco protoplasts (Gallie et al., 1989) than in maize protoplasts (Gallie and Young, 1994). Also, the 5'-UTLs from TMV-Ω (Gallie et al., 1988), AMV-coat (Gehrke et al., 1983; Jobling and Gehrke, 1987), TMV-coat (Goelet et al., 1982), and BMV-coat (French et al., 1986) worked poorly in maize and inhibited expression of a luciferase gene in maize relative to its native leader (Koziel et al., 1996). However, the 5'-UTLs from the cauliflower mosaic virus (CaMV) 35S transcript and the maize genes glutelin (Boronat et al., 1986), PEP-carboxylase (Hudspeth and Grula, 1989) and ribulose biphosphate carboxylase showed a considerable increase in expression of the luciferase gene in maize relative to its native leader (Koziel et al., 1996).

These 5'-UTLs had different effects in tobacco. In contrast to maize, the TMV Ω 5'-UTL and the AMV coat protein 5'-UTL enhanced expression in tobacco, whereas the glutelin, maize PEP-carboxylase and maize ribulose-1,5-bisphosphate carboxylase 5'-UTLs did not show enhancement relative to the native luciferase 5'-UTL (Koziel et al., 1996). Only the CaMV 35S 5'-UTL enhanced luciferase expression in both maize and tobacco (Koziel et al., 1996). Furthermore, the TMV and BMV coat protein 5'-UTLs were inhibitory in both maize and tobacco protoplasts (Koziel et al., 1996).

4.13.2 Use of Introns to Increase Expression

Including one or more introns in the transcribed portion of a gene has been found to increase heterologous gene expression in a variety of plant systems (Callis et al., 1987; Maas et al., 1991; Mascerenhas et al., 1990; McElroy et al., 1990; Vasil et al., 1989), although not all introns produce a stimulatory effect and the degree of stimulation varies. The enhancing effect of introns appears to be more apparent in monocots than in dicots. Tanaka et al., (1990) has shown that use of the catalase intron 1 isolated from castor beans increases gene expression in rice. Likewise, the first intron of the alcohol dehydrogenase 1 (Adh1) has been shown to increase expression of a genomic clone of Adhl comprising the endogenous promoter in transformed maize cells (Callis et al., 1987; Dennis et al., 1984). Other introns that are also able to increase expression of transgenes which contain them include the introns 2 and 6 of Adh1 (Luehrsen and Walbot, 1991), the catalase intron (Tanaka et al., 1990), intron 1 of the maize bronze 1 gene (Callis et al., 1987), the maize sucrose synthase intron 1 (Vasil et al., 1989), intron 3 of the rice actin gene (Luehrsen and Walbot, 1991), rice actin intron 1 (McElroy et al., 1990), and the maize ubiquitin exon 1 (Christensen et al., 1992).

Generally, to achieve optimal expression, the selected intron(s) should be present in the 5' transcriptional unit in the correct orientation with respect to the splice junction sequences (Callis et al., 1987; Maas et al., 1991; Mascerenhas et al., 1990; Oard et al., 1989; Tanaka et al., 1990; Vasil et al., 1989). Intron 9 of AdhI has been shown to increase expression of a heterologous gene when placed 3' (or downstream of) the gene of interest (Callis et al., 1987).

4.13.3 Use of Synthetic Genes to Increase Expression of Heterologous Genes in Plants When introducing a prokaryotic gene into a eukaryotic host, or when expressing a eukaryotic gene in a non-native host, the sequence of the gene must often be altered or modified to allow efficient translation of the transcript(s) derived form the gene. Significant experience in using synthetic genes to increase expression of a desired protein has been achieved in the expression of *Bacillus thuringiensis* in plants. Native *B. thuringiensis* genes are often expressed only at low levels in dicots and sometimes not at all in many species of monocots (Koziel et al., 1996). Codon usage in the native genes is considerably different from that found in typical plant genes, which have a higher G+C content. Strategies to increase expression of these genes in plants generally alter the overall G+C content of the genes. For example, synthetic *B. thuringiensis* crystal-protein encoding genes have resulted in significant improvements in expression of these endotoxins in various crops including cotton (Perlak et al., 1990; Wilson et al., 1992), tomato (Perlak et al., 1991), potato (Perlak et al., 1993), rice (Cheng et al., 1998), and maize (Koziel et al., 1993).

In a similar fashion the inventors contemplate that the genetic constructs of the present invention, because they contain one or more genes of bacterial origin, may in certain circumstances be altered to increase the expression of these prokaryotic-derived genes in particular eukaryotic host cells and/or transgenic plants which comprise such constructs. Using molecular biology techniques which are well-known to those of skill in the art, one may alter the coding or non coding sequences of the particular tIC8.51-encoding gene sequences to optimize or facilitate its expression in transformed plant cells at levels suitable for preventing or reducing insect infestation or attack in such transgenic plants.

4.13.4 Use of Promoters in Expression Vectors

The expression of a gene which exists in double-stranded DNA form involves transcription of messenger RNA (mRNA) from the coding strand of the DNA by an RNA polymerase enzyme, and the subsequent processing of the mRNA primary transcript inside the nucleus. Transcription of DNA into mRNA is regulated by a region of DNA referred to as the "promoter". The promoter region contains a sequence of bases that signals RNA polymerase to associate with the DNA and to initiate the transcription of mRNA using one of the DNA strands as a template to make a corresponding strand of RNA. The particular promoter selected should be capable of causing sufficient expression of the coding sequence to result in the production of an effective insecticidal amount of the *B. thuringiensis* protein.

A promoter is selected for its ability to direct the transformed plant cell's or transgenic plant's transcriptional activity to the coding region, to ensure sufficient expression of the enzyme coding sequence to result in the production of insecticidal amounts of the *B. thuringiensis* protein. Structural genes can be driven by a variety of promoters in plant tissues. Promoters can be near-constitutive (i.e. they drive transcription of the transgene in all tissue), such as the CaMV35S promoter, or tissue-specific or developmentally specific promoters affecting dicots or monocots. Where the promoter is a near-constitutive promoter such as CaMV35S or FMV35S, increases in polypeptide expression are found in a variety of transformed plant tissues and most plant organs (e.g., callus, leaf, seed and root). Enhanced or duplicate versions of the CaMV35S and FMV35S promoters are particularly useful in the practice of this invention (Kay et al., 1987; Rogers, U.S. Pat. No. 5,378,619).

Those skilled in the art will recognize that there are a number of promoters which are active in plant cells, and have been described in the literature. Such promoters may be obtained from plants or plant viruses and include, but are not limited to, the nopaline synthase (NOS) and octopine synthase (OCS) promoters (which are carried on tumor-inducing plasmids of *A. tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), the rice Act1 promoter and the Figwort Mosaic Virus (FMV) 35S promoter. All of these promoters have been used to create various types of DNA constructs which have been expressed in plants (see e.g., McElroy et al., 1990, U.S. Pat. No. 5,463,175).

In addition, it may also be preferred to bring about expression of the *B. thuringiensis* δ-endotoxin in specific tissues of the plant by using plant integrating vectors containing a tissue-specific promoter. Specific target tissues may include the leaf, stem, root, tuber, seed, fruit, etc., and the promoter chosen should have the desired tissue and developmental specificity. Therefore, promoter function should be optimized by selecting a promoter with the desired tissue expression capabilities and approximate promoter strength and selecting a transformant which produces the desired insecticidal activity in the target tissues. This selection approach from the pool of transformants is routinely employed in expression of heterologous structural genes in plants since there is variation between transformants containing the same heterologous gene due to the site of gene insertion within the plant genome (commonly referred to as "position effect"). In addition to promoters which are known to cause transcription (constitutive or tissue-specific) of DNA in plant cells, other promoters may be identified for use in the current invention by screening a plant cDNA library for genes which are selectively or preferably expressed in the target tissues and then determine the promoter regions.

An exemplary tissue-specific promoter is the lectin promoter, which is specific for seed tissue. The lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990). An expression vector containing a coding region that encodes a polypeptide of interest can be engineered to be under control of the lectin promoter and that vector may be introduced into plants using, for example, a protoplast transformation method (Dhir et al., 1991). The expression of the polypeptide would then be directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Other exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (McBride and Summerfelt, 1989), Ti plasmid nopaline synthase (Langridge et al., 1989), petunia chalcone isomerase (Van Tunen et al., 1988), bean glycine rich protein 1 (Keller et al., 1989), CaMV 35S transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al. (1987). Chloroplast or plastid specific promoters are known in the art (Daniell et al., U.S. Pat. No. 5,693,507; herein incorporated by reference), for example promoters obtainable from chloroplast genes, such as the psbA gene from spinach or pea, the rbcL and atpB promoter region from maize, and rRNA promoters. Any chloroplast or plastid operable promoter is within the scope of the present invention.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The present invention is not limited to constructs wherein the non-translated region is derived from the 5' non-translated sequence that accompanies the promoter sequence. As shown below, a plant gene leader sequence which is useful in the present invention is the petunia heat shock protein 70 (hsp70) leader (Winter et al., 1988).

An exemplary embodiment of the invention involves the plastid targeting or plastid localization of the B. thuringiensis amino acid sequence. Plastid targeting sequences have been isolated from numerous nuclear encoded plant genes and have been shown to direct importation of cytoplasmically synthesized proteins into plastids (reviewed in Keegstra and Olsen, 1989). A variety of plastid targeting sequences, well known in the art, including but not limited to ADPGPP, EPSP synthase, or ssRUBISCO, may be utilized in practicing this invention. In alternative embodiments preferred, plastidic targeting sequences (peptide and nucleic acid) for monocotyledonous crops may consist of a genomic coding fragment containing an intron sequence as well as a duplicated proteolytic cleavage site in the encoded plastidic targeting sequences.

Tables 5–7 list promoters which are illustrative of those known in the art, but which are not meant to be limiting.

TABLE 5

PLANT PROMOTERS

| Promoter | Reference |
|---|---|
| Viral | |
| Figwort Mosaic Virus (FMV) | U.S. Pat. No. 5,378,619 |
| Cauliflower Mosaic Virus (CaMV) | U.S. Pat. No. 5,530,196 |
| | U.S. Pat. No. 5,097,025 |
| | U.S. Pat. No. 5,110,732 |
| Plant | |
| Elongation Factor | U.S. Pat. No. 5,177,011 |
| Tomato Polygalacturonase | U.S. Pat. No. 5,442,052 |
| Arabidopsis Histone H4 | U.S. Pat. No. 5,491,288 |
| Phaseolin | U.S. Pat. No. 5,504,200 |
| Group 2 | U.S. Pat. No. 5,608,144 |
| Ubiquitin | U.S. Pat. No. 5,614,399 |
| P119 | U.S. Pat. No. 5,633,440 |
| α-amylase | U.S. Pat. No. 5,712,112 |
| Viral enhancer/Plant promoter | |
| CaMV 35Senhancer/mannopine synthase promoter | U.S. Pat. No. 5,106,739 |

TABLE 6

TISSUE SPECIFIC PLANT PROMOTERS

| Tissue Specific Promoter | Tissue(s) | Reference |
|---|---|---|
| Blec | epidermis | U.S. Pat. No. 5,646,333 |
| malate synthase | seeds; seedlings | U.S. Pat. No. 5,689,040 |

TABLE 6-continued

TISSUE SPECIFIC PLANT PROMOTERS

| Tissue Specific Promoter | Tissue(s) | Reference |
|---|---|---|
| isocitrate lyase | seeds; seedlings | U.S. Pat. No. 5,689,040 |
| patatin | tuber | U.S. Pat. No. 5,436,393 |
| ZRP2 | root | U.S. Pat. No. 5,633,363 |
| ZRP2(2.0) | root | U.S. Pat. No. 5,633,363 |
| ZRP2(1.0) | root | U.S. Pat. No. 5,633,363 |
| RB7 | root | U.S. Pat. No. 5,459,252 |
| | root | U.S. Pat. No. 5,401,836 |
| | fruit | U.S. Pat. No. 4,943,674 |
| | meristem | U.S. Pat. No. 5,589,583 |
| | guard cell | U.S. Pat. No. 5,538,879 |
| | stamen | U.S. Pat. No. 5,589,610 |
| SodA1 | pollen; middle layer; stomium of anthers | Van Camp et al., 1996 |
| SodA2 | vasular bundles; stomata; axillary buds; pericycle; stomium; pollen | Van Camp et al., 1996 |
| CHS15 | flowers; root tips | Faktor et al., 1996 |
| Psam-1 | phloem tissue; cortex; root tips | Vander et al., 1996 |
| ACT11 | elongating tissues and organs; pollen; ovules | Huang et al., 1997 |
| zmGBS | pollen; endosperm | Russell and Fromm, 1997 |
| zmZ27 | endosperm | Russell and Fromm, 1997 |
| osAGP | endosperm | Russell and Fromm, 1997 |
| osGT1 | endosperm | Russell and Fromm, 1997 |
| RolC | phloem tissue; bundle sheath; vascular parenchyma | Graham et al., 1997 |
| Sh | phloem tissue | Graham et al., 1997 |
| CMd | endosperm | Grosset et al., 1997 |
| Bnm1 | pollen | Treacy et al., 1997 |
| rice tungro bacilliform virus | phloem | Yin et al., 1997a; 1997b |
| S2-RNase | pollen | Ficker et al., 1998 |
| LeB4 | seeds | Baumlein et al., 1991 |
| gf-2.8 | seeds; seedlings | Berna and Bernier, 1997 |

The ability to express genes in a tissue specific manner in plants has led to the production of male and female sterile plants. Generally, the production of male sterile plants involves the use of anther-specific promoters operably linked to heterologous genes that disrupt pollen formation (U.S. Pat. Nos. 5,689,051; 5,689,049; 5,659,124). U.S. Pat. No. 5,633,441 discloses a method of producing plants with female genetic sterility. The method comprises the use of style-cell, stigma-cell, or style- and stigma-cell specific promoters that express polypeptides that, when produced in the cells of the plant, kills or significantly disturbs the metabolism, functioning or development of the cells.

TABLE 7

INDUCIBLE PLANT PROMOTERS

| Promoter | Reference |
|---|---|
| heat shock promoter | U.S. Pat. No. 5,447,858 |
| Em | U.S. Pat. No. 5,139,954 |
| Adh1 | Kyozoka et al., 1991 |
| HMG2 | U.S. Pat. No. 5,689,056 |
| cinnamyl alcohol dehydrogenase | U.S. Pat. No. 5,633,439 |
| asparagine synthase | U.S. Pat. No. 5,595,896 |
| GST-II-27 | U.S. Pat. No. 5,589,614 |

4.13.5 Chloroplast Sequestering and Targeting

Another approach for increasing expression of A+T rich genes in plants has been demonstrated in tobacco chloroplast transformation. High levels of expression of an unmodified *Bacillus thuringiensis* crystal protein-encoding genes in tobacco has been reported by McBride et al., (1995).

Additionally, methods of targeting proteins to the chloroplast have been developed. This technique, utilizing the pea chloroplast transit peptide, has been used to target the enzymes of the polyhydroxybutyrate synthesis pathway to the chloroplast (Nawrath et al., 1994). Also, this technique negated the necessity of modification of the coding region other than to add an appropriate targeting sequence.

U.S. Pat. No. 5,576,198 discloses compositions and methods useful for genetic engineering of plant cells to provide a method of controlling the timing or tissue pattern of expression of foreign DNA sequences inserted into the plant plastid genome. Constructs include those for nuclear transformation which provide for expression of a viral single subunit RNA polymerase in plant tissues, and targeting of the expressed polymerase protein into plant cell plastids. Also included are plastid expression constructs comprising a viral gene promoter region which is specific to the RNA polymerase expressed from the nuclear expression constructs described above and a heterologous gene of interest to be expressed in the transformed plastid cells.

4.13.6 Effects of 3' Regions on Transgene Expression

The 3'-end regions of transgenes have been found to have a large effect on transgene expression in plants (Ingelbrecht et al., 1989). In this study, different 3' ends were operably linked to the neomycin phosphotransferase II (NptII) reporter gene and expressed in transgenic tobacco. The different 3' ends used were obtained from the octopine synthase gene, the 2S seed protein from *Arabidopsis*, the small subunit of rbcS from *Arabidopsis*, extension form carrot, and chalcone synthase from *Antirrhinum*. In stable tobacco transformants, there was about a 60-fold difference between the best-expressing construct (small subunit rbcS 3' end) and the lowest expressing construct (shalcone synthase 3' end).

4.14 Antibody Compositions and Methods of Making

In particular embodiments, the inventors contemplate the use of antibodies, either monoclonal or polyclonal which bind to one or more of the polypeptides disclosed herein. Means for preparing and characterizing antibodies are well known in the art (See, e.g., Harlow and Lane, 1988). The methods for generating monoclonal antibodies (mAbs) generally begin along the same lines as those for preparing polyclonal antibodies. mAbs may be readily prepared through use of well-known techniques, such as those exemplified in U.S. Pat. No. 4,196,265. Antibody use is well known in the art and can be used for purification, immunoprecipitation, ELISA and western blot for resolving the presence of molecules having identifiable epitopes. Those skilled in the art would not encounter undue experimentation in using antibodies and such methods to idolate, identify, and characterize genes and proteins expressed from such genes as contemplated herein. Immuno-based detection methods for use in conjunction with Western blotting include enzymatically-, radiolabel-, or fluorescently-tagged secondary antibodies against the toxin moiety are considered to be of particular use in this regard.

4.15 Biological Functional Equivalents

Modification and changes may be made in the structure of the peptides of the present invention and DNA sequences which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated crystal proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 8.

TABLE 8

| Amino Acids | Codon Abbreviations[1] | | Codons |
|---|---|---|---|
| Alanine | Ala | A | GCA GCC GCG GCU |
| Arginine | Arg | R | AGA AGG CGA CGC CGG CGU |
| Asparagine | Asn | N | AAC AAU |
| Aspartic acid | Asp | D | GAC GAU |
| Cysteine | Cys | C | UGC UGU |
| Glutamic acid | Glu | E | GAA GAG |
| Glutamine | Gln | Q | CAA CAG |
| Glycine | Gly | G | GGA GGC GGG GGU |
| Histidine | His | H | CAC CAU |
| Isoleucine | Ile | I | AUA AUC AUU |
| Leucine | Leu | L | UUA UUG CUA CUC CUG CUU |
| Lysine | Lys | K | AAA AAG |
| Methionine | Met | M | AUG UUG* |
| Phenylalanine | Phe | F | UUC UUU |
| Proline | Pro | P | CCA CCC CCG CCU |
| Serine | Ser | S | AGC AGU UCA UCC UCG UCU |
| Threonine | Thr | T | ACA ACC ACG ACU |
| Tryptophan | Trp | W | UGG |
| Tyrosine | Tyr | Y | UAC UAU |
| Valine | Val | V | GUA GUC GUG GUU |

*the codon UUG is also utilized as an initiation codon as a part of the tJC851 coding sequence
[1]three letter code and corresponding single letter code abbreviations For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

*Bacillus Thuringiensis* Strains with Sequences Related to CryET70

We previously identified a *B. thuringiensis* strain expressing a protein which we designated CryET70. The CryET70 protein had effective coleopteran specific bioactivity when provided in bioassay feeding studies to western corn rootworm larvae, but not against southern corn rootworm larvae. We were interested in identifying additional *B. thuringiensis* strains which contained DNA encoding CryET70 and closely related genes. Colony blot hybridization experiments were completed as indicated below, using a probe prepared from cryET70 DNA. Wild-type *B. thuringiensis* strains were patched onto LB plates and incubated at 30° C. for four hours. A Nytran® Maximum-Strength Plus (Schleicher and Schuell, Keene, NH) circular (82 mm) membrane filter was then placed on the plates and the plates and filters were incubated at 25° C. overnight. The filters, which contained an exact replica of the patches, were then placed on fresh LB plates, and the filters and the original plates were incubated at 30° C. for 4 hr to allow for growth of the colonies. To release the DNA from the *B. thuringiensis* cells onto the nitrocellulose filter, the filters were placed, colony-side up, on Whatman 3 MM Chromatography paper (Whatman International LTD., Maidstone, England) soaked with 0.5 N NaOH, 1.5 M NaCl for 15 min. The filters were then neutralized by placing the filters, colony-side up, on Whatman paper soaked with 1 M $NH_4$-acetate, 0.02 M NaOH for 10 min. The filters were then rinsed in 3×SSC, 0.1% SDS, air dried, and baked for one hr at 80° C. in a vacuum oven to prepare them for hybridization.

Oligonucleotide Primers were Designed Based on the CryET70 Sequence (SEQ ID NO:1):

```
AM34: 5'-GACATGATTTTACTTTTAGAGC-3'   (SEQ ID NO:3)

AM43: 5'-CATCACTTTCCCCATAGC-3'       (SEQ ID NO:4)
```

A PCR™ with primers AM 34 and AM 43 was used to amplify a cryET70 fragment from pEG1648 DNA. This PCR™ product was labeled with [$\alpha^{-32}$P]dATP using the Prime-a-Gene® kit (Promega Corporation, Madison, Wis.) to generate a cryET70-specific probe. Hybridizations were performed overnight with the hybridization temperature at 63° C. Filters were washed in 1×SSC, 0.1% SDS at 63° C. Hybridizing colonies were detected by autoradiography using Kodak X-OMAT AR X-ray film. The results indicated that several *B. thuringiensis* strains in our collection contained DNA sequences which hybridized to cryET70 sequences under specified conditions. The strains identified by colony blot hybridization are listed in Table 9.

5.2 Example 2

Production of Antibody to CryET70

CryET70 specific polyclonal antibody was prepared so that proteins containing CryET70-related epitopes could be identified using immunological methods. Recombinant *B. thuringiensis* strain EG11839 containing plasmid pEG1648 expressing CryET70 was grown in C2 medium for four days at 25° C. The resulting spores and crystals were washed in 2.5× volume $H_2O$ and resuspended at 1/20 the original volume in 0.005% Triton X-100®. The spore-crystal suspension was then loaded on a sucrose step gradient consisting of 79%, 72% and 55% sucrose. The gradient was spun overnight in a Beckman SW28 at 18,000 RPM. CryET70 crystals banded between the 79% and the 72% sucrose layers. CryET70 crystals were washed several times in $H_2O$ and resuspended in 0.005% Triton X-100®. The purified crystals were then solubilized in 50 mM sodium carbonate (pH 10), 5 mM DTT, and any contaminating vegetative cells or spores were removed by centrifugation. The supernatant was neutralized with boric acid to pH8.4, and the solubilized crystals were sent to Rockland Laboratories (Gilbertsville, Pa.) for antibody production in rabbits according to standard procedures. The rabbits received two intradermal injections on days zero and seven with 50% CryET70 protein in sterile phosphate buffered saline, 50% complete Freund's adjuvant. Two additional boosts were given subcutaneously on days 14 and 28 before a test bleed on day 38. Two hundred fifty μg of CryET70 were used per rabbit for the initial injection, and 125 μg of CryET70 were used per rabbit for the subsequent boosts. On day 56 the rabbits were boosted again, as before, prior to a production bleed on day 71. The final boost was with 160 μg CryET70 on day 80, followed by a termination bleed on day 90.

5.3 Example 3

Southern and Western Blot Analyses

Strains identified in Example 1 as containing sequences related to cryET70 were examined further by Southern and Western blot analyses.

Total DNA was prepared from the strains by the following procedure. Vegetative cells were resuspended in a lysis buffer containing 50 mM glucose, 25 mM Tris-HCl (pH8.0), 10 mM EDTA, and 4 mg/ml lysozyme. The suspension was incubated at 37° C. for one hr. Following incubation, SDS was added to 1%. The suspension was then extracted with an equal volume of phenol:chloroform:isoamyl alcohol (50:48:2). DNA was precipitated from the aqueous phase by the addition of one-tenth volume 3 M sodium acetate, and two volumes of 100% ethanol. The precipitated DNA was collected with a glass rod, washed with 70% ethanol, and resuspended in $dH_2O$.

Total DNA was digested with EcoRI and separated on a 0.8% agarose gel in TAE buffer (40 mM Tris-acetate, 2 mM $Na_2EDTA$, pH 8). The DNA was blotted onto an Immobilon-NC nitrocellulose filter (Millipore Corp., Bedford, Mass.) according to the method of Southern (1975). DNA was fixed to the filter by baking at 80° C. in a vacuum oven.

The blot was then hybridized with the cryET70 probe described in Example 1. The filters were exposed to the labeled probe diluted in 3×SSC, 0.1% SDS, 10× Denhardt's reagent (0.2% bovine serum albumin (BSA), 0.2% polyvinylpyrrolidone, 0.2% Ficoll®), 0.2 mg/ml heparin and incubated overnight at 60° C. Following the incubation, the filters were washed in three changes of 3×SSC, 0.1% SDS at 60° C. The filters were blotted dry and exposed to Kodak X-OMAT AR X-ray film (Eastman Kodak Company, Rochester, N.Y.) overnight at −70° C. with an intensifying screen (Fisher Biotech, Pittsburgh, Pa.). Strains containing hybridizing DNA fragments are listed in Table 9.

For the Western blot analysis, *B. thuringiensis* strains were grown in C2 medium (Donovan et al., 1988) at 25° C. for four days until sporulation and cell lysis had occurred. The resulting spores and crystals were harvested by centrifugation, washed in approximately 2.5 times the original volume with $H_2O$, and resuspended in 0.005% Triton X-100® at one-tenth the original volume. Proteins from 10-fold concentrated cultures of the strains were run on a 10% SDS-polyacrylamide gel (Owl Separation Systems, Woburn, Mass.). Twenty μl of culture was added to 10 μl of 3× Laemmli buffer and heated at 100° C. for five minutes. Fifteen μl were loaded per lane. Following electrophoresis, the gel was blotted to nitrocellulose following standard Western blotting procedures (Towbin et al., 1979). The filter was blocked with TBSN (10 mM Tris, pH 7.8, 0.9% NaCl, 0.1% globulin-free BSA, 0.03% $NaN_3$)+2% BSA. The filter was then washed with TBSN twice and then incubated with anti-CryET70 rabbit antiserum diluted 1/1,000 in TBSN. The filter was then washed in TBSN and incubated with alkaline phosphatase conjugated sheep anti-rabbit IgG (1/1,000 dilution in TBSN). After washing in TBSN, proteins antigenically related to CryET70 were detected with ImmunoPure® NBT/BCIP Substrate Kit (Pierce, Rockford, Ill.). *B. thuringiensis* strains producing proteins antigenically related to CryET70 as judged by Western blot analysis are indicated in Table 9.

5.4 Example 4

Bioassay Evaluation of *B. Thuringiensis* Strains

Insect bioassays were used to characterize *B. thuringiensis* strains having activity directed against western corn rootworm larvae. *B. thuringiensis* strains were grown in C2 medium (Donovan et al., 1988) at 25° C. for four days at which time sporulation and lysis had occurred. The resulting spores and crystals were harvested by centrifugation, washed in approximately 2.5 times the original volume with water, and resuspended in 0.005% Triton X-100® at one-tenth the original culture volume. The spore-crystal suspensions were used directly in bioassay.

Insecticidal activity against WCRW larvae was determined via a surface contamination assay on an artificial diet (20 g agar, 50 g wheat germ, 39 g sucrose, 32 g casein, 14 g fiber, 9 g Wesson salts mix, 1 g methyl paraben, 0.5 g sorbic acid, 0.06 g cholesterol, 9 g Vaderzant's vitamin mix, 0.5 ml linseed oil, 2.5 ml phosphoric/propionic acid per liter) in a plastic feeding cup (175 $mm^2$ surface). All bioassays were performed using 128-well trays containing approximately 1 ml of diet per well with perforated mylar sheet covers (C-D International Inc., Pitman, N.J.). Thirty-two larvae (one per well) were tested per bioassay screen at 50 μl of a spore-crystal suspension per well of diet. The results of the bioassay screen are shown in Table 9.

TABLE 9

SUMMARY OF SOUTHERN, WESTERN, AND BIOASSAY ANALYSES

| Strains | Southern blot | Western blot | % Control WCRW |
|---|---|---|---|
| EG2929 | + | + | 26 |
| EG3218 | +/− | − | 30 |
| EG3221 | +/− | − | 63 |
| EG3303 | +/− | − | 15 |
| EG3304 | +/− | | 0 |
| EG3707 | + | − | 45 |
| EG3803 | | − | 0 |
| EG3953 | + | | 100 |
| EG3966 | + | − | 7 |
| EG4113 | − | − | 40 |
| EG4135 | + | + | 45 |
| EG4150 | − | − | 64 |
| EG4268 | − | + | 46 |
| EG4375 | | − | 100 |
| EG4447 | +/− | | 0 |
| EG4448 | + | − | 100 |
| EG4503 | +/− | − | 56 |
| EG4541 | +/− | − | 72 |
| EG4580 | + | + | 33 |
| EG4640 | − | − | 95 |
| EG4737 | − | − | 72 |
| EG4741 | + | − | 73 |
| EG5233 | − | − | 52 |
| EG5366 | + | − | 69 |
| EG5370 | − | − | 16 |
| EG5422 | | − | 8 |

5.5 Example 5

Analysis of Wild-Type *B. Thuringiensis* Strains

The CryET70 peptide sequence has previously been shown to share significant amino acid sequence identity with Cry22Aa. Based on the known nucleotide and amino acid sequences of CryET70 and Cry22Aa, thermal amplification primers were designed for sequences similar or identical to those of the CryET70 and Cry22Aa coding sequences.

TABLE 10

Thermal Amplification Oligonucleotide Sequence Alignment in cry22Aa and cryET70

| | | Corresponding Position of Oligo in: | |
|---|---|---|---|
| Oligo[a] | Sequence (5'-3') & Corresponding SEQ ID NO | cry2Aa (SEQ ID NO:9) | cryET70 (SEQ ID NO:1) |
| 2270-1 | GCATTTCATAGAGGATCAAT SEQ. ID NO:5 | 262–281 | 350–369 |

TABLE 10-continued Thermal Amplification Oligonucleotide Sequence Alignment in cry22Aa and cryET70

| Oligo[a] | Sequence (5'-3') & Corresponding SEQ ID NO | Corresponding Position of Oligo in: | |
|---|---|---|---|
| | | cry2Aa (SEQ ID NO:9) | cryET70 (SEQ ID NO:1) |
| 2270-2 | ATTGATCCTCTATGAAATGC SEQ ID NO:11 | 281–262 | 369–350 |
| 2270-3 | GTTTCCCAAATGGATATCC SEQ ID NO:12 | 428–446 | 516–534 |
| 2270-4 | GGATATCCATTTGGGAAAC SEQ ID NO:13 | 446–428 | 534–516 |
| 2270-5 | ATCTAATAACCTACATCAGA SEQ ID NO:14 | 726–745 | 814–833 |
| 2270-6 | TCTGATGTAGGTTATTAGAT SEQ ID NO:15 | 745–726 | 833–814 |
| 2270-7 | TATGGGGAAAGTGATGAAAA SEQ ID NO:16 | 973–992 | 1061–1080 |
| 2270-8 | TTTTCATCACTTTCCCCATA SEQ ID NO:6 | 992–973 | 1080–1061 |
| 2270-9 | ATGTTGAATTAGAAATAG SEQ ID NO:17 | 1280–1297 | 1368–1385 |
| 2270-10 | CTATTTCTAATTCAACAT SEQ ID NO:18 | 1297–1280 | 1385–1358 |
| 2270-11 | AAGTCCTTGTTCTAGGAGAA SEQ ID NO:19 | 1481–1500 | 1569–1588 |
| 2270-12 | TTCTCCTAGAACAAGGACTT SEQ ID NO:20 | 1500–1481 | 1588–1569 |
| 2270-13 | TATGTATTCTATGATTCTAG SEQ ID NO:21 | 1840–1859 | 1928–1947 |
| 2270-14 | CTAGAATCATAGAATACATA SEQ ID NO:22 | 1859–1840 | 1947–1928 |

[a]: odd numbered oligonucleotides represent sequences identical to the indicated position for each gene (SEQ ID NO), and even numbered oligonucleotides represent sequences complementary to the indicated position for each gene (SEQ ID NO).

Even numbered oligonucleotides were paired with odd numbered oligonucleotides in various combinations in thermal amplification reactions in order to confirm the expected size of fragments from amplification of sequences from both cryET70 and cry22Aa. DNA obtained from strains EG4135 and EG4268 was also used in separate thermal reactions with all primer pairs. While all pairs produced amplification fragments from both cryET70 and cry22Aa, the only oligonucleotide primer pair which produced a product from DNA of strains EG4135 and EG4268 was the 2270-1 and 2270-8 primer pair (SEQ ID NO:5 & SEQ ID NO:6 respectively).

Amplification reactions were performed using 'TaqBeads' (Pharmacia Biotech), a Stratagene Robocycler™, and the following cycling regimen: 94 C for 30 seconds, 45 C for 45 seconds, and 72 C for 1 minute for 30 cycles. Thermocycling was preceded by a 5 minute incubation at 94 C, followed by a 5 minute incubation at 72 C. The amplification products produced from strains EG4135 and EG4268 were cloned as blunt-end fragments into the SmaI site of pBluescript KSII(+) and sequenced. The sequences of the DNA inserts indicated the presence of an open reading frame (ORF) which displayed approximately 65% sequence identity to the corresponding region from either CryET70 or Cry22Aa.

5.6 Example 6

Sequence Analysis of the Full-Length Gene

Genomic DNA libraries from strains EG4135 and EG4268 were constructed in the Lambda Zap® II vector (Stratagene; La Jolla, Calif.) and used to isolate recombinant clones containing the entire ORF identified in Example 5. The ORF encodes a protein of 632 amino acids, designated tIC851. The nucleotide sequence encompassing the tIC851 gene (SEQ ID NO:7) is shown below:

```
AAATATTTTT AAAGGGGGAT ACGTAATTTG AATTCTAAAT CTATCATCGA AAAAGGGGTA    60

CAAGAGAATC AATATATTGA TATTCGTAAC ATATGTAGCA TTAATGGTTC TGCTAAATTT   120

GATCCTAATA CTAACATTAC AACCTTAACA GAAGCTATCA ATTCTCAAGC AGGAGCGATT   180

GCTGGAAAAA CTGCCCTAGA TATGAGACGT GATTTTACTC TCGTAGCAGA TATATACCTA   240

GGGTCTAAAA GTAGTGGAGC TGATGGTATT GCTATAGCGT TTCATAGAGG ATCAATTGGT   300

TTTATCGGTA CCATGGGTGG AGGCTTAGGG ATTCTAGGAG CACCAAACGG GATAGGATTT   360

GAAATAGATA CGTATTGGAA AGCAACTTCA GATGAAACAG GCGATTCATT TGGACATGGT   420

CAAATGAATG GAGCACATGC GGGATTTGTA AGTACAAATC GAAATGCAAG CTATTTAACA   480

GCCTTAGCTC CTATGCAAAA AATACCTGCA CCTAATAATA AATGGCGGGT TCTAACTATC   540

AATTGGGATG CGCGTAACAA CAAACTAACA GCACGGCTTC AAGAGAAAAG TAATGATGCT   600

TCTACTAGCA CTCCTAGTCC AAGATATCAA ACATGGGAAC TATTAAATCC TGCGTTTGAT   660

TTAAATCAGA AATATACTTT TATTATCGGC TCAGCTACAG GGGCTGCTAA TAACAAGCAT   720

CAGATTGGAG TTACTTTGTT TGAAGCATAC TTTACAAAAC CAACTATAGA GGCAAATCCT   780

GTTGATATTG AACTAGGCAC AGCGTTTGAT CCATTAAACC ATGAGCCAAT GGACTCAAA    840

GCAACAGATG AAGTAGATGG AGATATAACA AAGGACATTA CGGTAGAATT TAATGACATA   900

GATACCTCCA AACCAGGTGC ATACCGTGTA ACATATAAAG TAGTAAATAG TTATGGAGAA   960

AGTGATGAGA AAACAATAGA AGTCGTAGTA TACACGAAAC CAACTATAAC TGCACATGAT  1020

ATTACGATTA AGAAAGACTT AGCATTTGAT CCATTAAACT ATGAACCAAT GGACTCAAA   1080

GCAACCGATC CAATTGATGG AGATATAACA GATAAAATCG CTGTAAAATT TAATAATGTC  1140

GATACCTCTA AACCGGGTAA ATACCATGTA ACATATAAAG TGATAAATAG TTATGAAAAA  1200

ATTGATGAAA AAACAATAGA GGTCACAGTA TATACGAAAC CATCTATAGT GGCACATGAT  1260

GTTGAGATTA AAAAGATAC GGCATTTGAT CCGTTAAACT ATGAACCAAT TGGGCTCAAA   1320

GCAACCGATC CAATTGATGG AGATATAACA GATAAAATTA CGGTAGAATC TAATGATGTT  1380

GATACCTCTA AACCAGGTGC ATATAGTGTG AAATATAAAG TAGTAAATAA TTATGAAGAA  1440

AGTGACGAAA AAACAATTGC CGTTACAGTA CCTGTTATAG ATGATGGGTG GGAGAATGGC  1500

GATCCGACAG GATGGAAATT CTTCTCTGGT GAAACCATTA CTCTAGAAGA TGATGAAGAG  1560

CATGCTCTTA ATGGTAAATG GGTATTTTAT GCTGATAAAC ATGTAGCAAT ATACAAACAA  1620

GTAGAGTTGA AGAATAATAT CCCTTATCAA ATTACAGTAT ATGTTAAACC AGAAGATGAA  1680

GGAACTGTGG CACACCATAT TGTTAAAGTA TCTTTCAAAT CTGATTCTGC TGGTCCAGAA  1740

AGTGAAGAAG TTATAAATGA AAGATTAATT GATGCAGAAC AGATACAAAA AGGATACAGA  1800

AAGTTAACAA GTATTCCATT TACACCAACA ACCATTGTTC CCAACAAAAA ACCAGTGATA  1860

ATTGTTGAAA ACTTTTTACC AGGATGGATA GGTGGAGTTA GAATAATTGT AGAGCCTACA  1920

AAGTAAGAAT TATAAACTAG CTTTTAATAA ATATATTTAA AAAAT               1965
```

The tIC851 ORF initiation codon is TTG beginning at nucleotide 28 of the sequence shown above. The deduced amino acid sequence (SEQ ID NO. 8) of the tIC851 protein is shown below, as translated from the ORF described above:

```
MNSKSIIEKG VQENQYIDIR NICSINGSAK FDPNTNITTL TEAINSQAGA IAGKTALDMR    60

RDFTLVADIY LGSKSSGADG IAIAFHRGSI GFIGTMGGGL GILGAPNGIG FEIDTYWKAT  120
```

-continued

```
SDETGDSFGH GQMNGAHAGF VSTNRNASYL TALAPMQKIP APNNKWRVLT INWDARNNKL   180

TARLQEKSND ASTSTPSPRY QTWELLNPAF DLNQKYTFII GSATGAANNK HQIGVTLFEA   240

YFTKPTIEAN PVDIELGTAF DPLNHEPIGL KATDEVDGDI TKDITVEFND IDTSKPGAYR   300

VTYKVVNSYG ESDEKTIEVV VYTKPTITAH DITIKKDLAF DPLNYEPIGL KATDPIDGDI   360

TDKIAVKFNN VDTSKPGKYH VTYKVINSYE KIDEKTIEVT VYTKPSIVAH DVEIKKDTAF   420

DPLNYEPIGL KATDPIDGDI TDKITVESND VDTSKPGAYS VKYKVVNNYE ESDEKTIAVT   480

VPVIDDGWEN GDPTGWKPFS GETITLEDDE EHALNGKWVF YADKHVAIYK QVELKNNIPY   540

QITVYVKPED EGTVAHHIVK VSFKSDSAGP ESEEVINERL IDAEQIQKGY RKLTSIPFTP   600

TTIVPNKKPV IIVENFLPGW IGGVRIIVEP TK                                 632
```

The predicted molecular weight for this protein is 69,398 Daltons.

The amino acid sequences of tIC851 (SEQ ID NO: 8), CryET70 O (SEQ ID NO: 2), and Cry22Aa (SEQ ID NO: 10) were aligned as shown below using the CLUSTAL alignment program (PC/GENE®). The tIC851 protein shares approximately 56% amino acid sequence identity with CryET70 and approximately 57% amino acid sequence identity with Cry22Aa. According to current *Bacillus thuringiensis* crystal protein nomenclature rules, the tIC851 protein should be assigned to a new secondary class of Cry proteins.

For the three way alignment, the K-tuple value was set at 1, the gap penalty value was set at 5, the window size was set at 10, the filtering level was set at 2.5, the open gap cost was set at 10, and the unit gap cost was set at 10. An "*" indicates that a position in the alignment is perfectly conserved, and a '.' indicates that a position is well conserved.

```
Cry22Aa  MKEQNLNKYDEITVQAASDYIDIRPIFQTNGSATFNSNTNITTLTQAINS   50
ET70     MKDSISKGYDEITVQA-SDYIDIRSIFQTNGSATFNSTTNITTLTQATNS   49
tIC851   MN---SKSIIEKGVQE-NQYIDIRNICSINGSAKFDPNTNITTLTEAINS   46
         *.    .   * .**. ..***** *  .****.*...*******.*.**
Cry22Aa  QAGAIAGKTALDMRHDFTFRADIFLGTKSNGADGIAIAFHRGSIGFVGTK  100
ET70     QAGAIAGKTALDMRHDFTFRADIFLGTKSNGADGIAIAFHRGSIGFVGEK   99
tIC851   QAGAIAGKTALDMRRDFTLVADIYLGSKSSGADGIAIAFHRGSIGFIGTM   96
         **************.***. ***.**.**.****************.*..
Cry22Aa  GGGLGILGAPKGIGFELDTYANAPEDEVGDSFGHGAMKGSFPSFPNGYPH  150
ET70     GGGLGILGALKGIGFELDTYANAPQDEQGDSFGHGAMRGLFPGFPNGYPH  149
tIC851   GGGLGILGAPNGIGFEIDTYWKATSDETGDSFGHGQMNG---------AH  137
         ********* .*****.*** .*. ** *******.*.*         .*
Cry22Aa  AGFVSTDKNSRWLSALAQMQRIAAPNGRWRRLEIRWDARNKELTANLQDL  200
ET70     AGFVSTDKNRGWLSALAQMQRIAAPNGRWRRLAIHWDARNKKLTANLEDL  199
tIC851   AGFVSTNRNASYLTALAPMQKIPAPNNKWRVLTINWDARNNKLTARLQE-  186
         ******..*  .*.***.**.*.***..** *.*.*****..***.*..
Cry22Aa  TFNDITVGEKPRTPRTATWRLVNPAFELDQKYTFVIGSATGASNNLHQIG  250
ET70     TFNDSTVLVKPRTPRYARWELSNPAFELDQKYTFVIGSATGASNNLHQIG  249
tIC851   --KSNDASTSTPSPRYQTWELLNPAFDLNQKYTFIIGSATGAANNKHQIG  234
           .. ..  ....** . * * ****.*.*****.*******.** ****
Cry22Aa  IIEFDAYFTKPTIEANNVNVPVGATFNPKTYPGINLRATDEIDGDLTSKI  300
ET70     IIEFDAYFTKPTIEANNVSVPVGATFNPKTYPGINLRATDEIDGDLTSEI  299
tIC851   VTLFEAYFTKPTIEANPVDIELGTAFDPLNHEPIGLKATDEVDGDITKDI  284
         .. *.*********** *.. .*..*.* ..  *.*.****.***.*..*
Cry22Aa  IVKANNVNTSKTGVYYVTYYVENSYGESDEKTIEVTVFSNPTIIASDVEI  350
ET70     IVTDNNVNTSKSGVYNVTYYVKNSYGESDEKTIEVTVFSNPTIIASDVEI  349
tIC851   TVEFNDIDTSKPGAYRVTYKVVNSYGESDEKTIEVVVYTKPTITAHDITI  334
         .*. *...***.*.* *** * *************.*...***.* *..*
Cry22Aa  EKGESFNPLTDSRVGLSAQDSLGNDITQNVKVKSSNVDTSKPGEYEVVFE  400
ET70     EKGESFNPLTDSRVRLSAQDSLGNDITSKVKVKSSNVDTSKPGEYDVVFE  399
tIC851   KKDLAFDPL----------------------------------NYE----  346
         .*. .* **                                  .*.
Cry22Aa  VTDSFGGKAEKDFKVTVLGQPSIEANNVELEIDDSLDPLTDAKVGLRAKD  450
ET70     VTDNFGGKAEKEIKVTVLGQPSIEANDVELEIGDLFNPLTDSQVGLRAKD  449
tIC851   ------------------------------------------PIGLKATD  354
                                                  .**.*.*
Cry22Aa  SLGNDITKDIKVKFNNVDTSNSGKYEVIFEVTDRFGKKAEKSIEVLVLGE  500
ET70     SLGKDITNDVKVKSSNVDTSKPGEYEVVFEVTDRFGKKAEKSIKVLVLGE  499
tIC851   PIDGDITDKIAVKFNNVDTSKPGKYHVTYKVINSYEKIDEKTIEVTVYTK  404
         ... ***... ** .*****..*.*.*...*.....* .**.*.* * ..
Cry22Aa  PSIEANDVEVNKGETFEPLTDSRVGLRAKDSLGNDITKDVKIKSSNVDTS  550
ET70     PSIEANNVEIEKDERFDPLTDSRVGLRAKDSLGKDITNDVKVKSSNVDTS  549
tIC851   PSIVAHDVEIKKDTAFDPLNYEPIGLKATDPIDGDITDKITVESNDVDTS  454
         *** *..**..*.. *.**. ...**.*.*... ***......*..****
Cry22Aa  KPGEYEVVFEVTDRFGKYVEKTIGVIVPVIDDEWEDGNVNGWKFYAGQDI  600
```

```
                                    -continued
ET70      KPGEYEVVFEVTDRFGKYVKKLIVVIVPVIDDEWEDGNVNGWKFYAGQDI    599
tIC851    KPGAYSVKYKVVNNYEESDEKTIAVTVPVIDDGWENGDPTGWKFFSGETI    504
          ***.*.*  ..*......  .* * *.******.**.*. .****..*..*
Cry22Aa   KLLKDPDKAYKGDYVFYDSRHVAISKTIPLTDLQINTNYEITVYAKAES-    649
ET70      TLLKDPEKAYKGEYVFYDSRHAAISKTIPVTDLQVGGNYEITVYVKAES-    648
tIC851    TLEDDEEHALNGKWVFYADKHVAIYKQV---ELKNNIPYQITVYVKPEDE    551
          .*  .*  ..*  .*..***...*.**  * .   .*. .  *.****.*.*.
Cry22Aa   ---GDHHLKVTYKKDPAGPEEPPVFNRLISTGTLVEKDYRELKGT-FRVT    695
ET70      ---GDHHLKVTYKKDPKGPEEPPVFNRLISTGKLVEKDYRELKGT-FRVT    694
tIC851    GTVAHHIVKVSFKSDSAGPESEEVINERLIDAEQIQKGYRKLTSIPFTPT    601
            ..*  .**..*.*. ***.   *.*   .  ...  ...*.**.*.... *   *
Cry22Aa   EL--NKAPLIIVENFGAGYIGGIRIV--KIS                       722
ET70      EL--NQAPLIIVENFGAGYIGGIRIV--KIS                       721
tIC851    TIVPNKKPVIIVENFLPGWIGGVRIIVEPTK                       632
          ..  *. *.******  .*.***.**.    ..
```

5.7 Example 7

Expression of the tIC851 Protein in *B. Thuringiensis* and Bioassay Evaluation

The coding region for tIC851 was cloned into the *B. thuringiensis* shuttle vector pEG597 (Baum et al., 1990) together with about 0.6 kb of flanking native DNA both up and down stream of the ORF, giving rise to the recombinant plasmids pIC17501 and pIC17502. These plasmids contain a gene which confers chloramphenicol resistance on a *B. thuringiensis* host cell. Plasmid pMON56207, containing the cryET70 coding sequence, confers erythromycin resistance to a *B. thuringiensis* host. These plasmids were introduced into the Cry- *B. thuringiensis* strain EG10650 by electroporation. Recombinants harboring the correct plasmids were selected for growth on starch agar medium supplemented with the appropriate antibiotic.

Recombinants were grown in C2 medium for 72–96 hours, at which time the cultures were sporulated and the cells lysed. Plasmids pIC17501 and pIC17502, differing only with respect to the orientation of the tIC851 gene insert, directed the production of a protein with an apparent molecular mass of approximately 75 kDa, as judged by SDS polyacrylamide gel electrophoresis. EG10650 recombinants harboring the cloning vector pEG597 did not produce a crystal protein. Plasmid pMON56207 directed the production of CryET70, with an apparent molecular mass of approximately 80 kDa.

tIC851 was tested against boll weevil larvae and western corn rootworm (WCRW) larvae in an insect feeding bioassay and shown not to have activity against WCRW, but surprisingly good activity against boll weevil. Based on the similarity of tIC851 to CryET70 and Cry22Aa, these two proteins were also tested against boll weevil. A dose-response study on the susceptibility of the boll weevil to these *B. thuringiensis* toxins was performed by diet incorporation (Stone et al. 1991). A series of 3 to 8 concentrations prepared by serial dilution was used in each instance. First instar larvae were manually infested onto the diet. Mortality and weight measurements were recorded 10 days after infestation. Larvae that were dead or were still at the neonate stage were considered dead in tabulating larval responses to the individual proteins. Concentration-mortality regressions were estimated assuming the probit model (SAS software 1995). Weight records were used to calculate effective concentrations using the non-linear regression model (SAS 1995).

Surprisingly, Cry22Aa was also found to have significant toxicity to boll weevil larvae comparable to that of CryET70, as indicated in Table 11. This is the first report that Cry22Aa and CryET70 have activity against this target insect pest.

TABLE 11

| | Cotton boll weevil Bioassay | |
|---|---|---|
| Protein | LC$_{50}$ (μg/well) | EC$_{50}$ (μg/well) |
| CryET70 | 3.12 (1.95–5.00) | 1.92 ± 0.37 |
| Cry22Aa | 0.72 (0.022–1.70) | 0.36 ± 0.18 |

The toxin encoded by the tIC851 gene has interesting similarities as well as differences when compared with the toxins encoded by the CryET70 and Cry22Aa genes. Both CryET70 and Cry22Aa have within their primary sequence four repeating regions of approximately 80 amino acids each, aligned in a head-to-tail fashion. The sequence of tIC851 shows that the tIC851 protein has only three of the four 'repeat domains' found in CryET70 and Cry22Aa. This accounts for most of the approximately 90 amino acids by which the tIC851 coding sequence is shorter than that of either CryET70 or Cry22Aa. Despite this difference in structure, tIC851 has significant activity on boll weevil larvae. The novel modular structure of these three Bt toxins should be of value in semi-rational engineering of variants, which could have increased potency or spectrum of activity.

5.8 Example 8

Transgenic Plants Expressing tIC851

One or more transgenes, each containing a structural coding sequence of the present invention can be inserted into the genome of a plant by any suitable method such as those detailed herein. Suitable plant transformation vectors include those derived from a Ti plasmid of *Agrobacterium tumefaciens*, as well as those disclosed, e.g., by Herrera-Estrella (1983), Bevan (1983), Klee (1985) and Eur. Pat. Appl. Publ. No. EPO120516. In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen (Fromm et al., 1986; Armstrong et al., 1990; Fromm et al., 1990). For efficient expression of the polynucleotides disclosed herein in transgenic plants, the selected sequence region encoding the insecticidal polypeptide must have a suitable sequence composition (Diehn et al., 1996).

Expression of the tIC851 protein from within a plant expression vector is then confirmed in plant protoplasts by electroporation of the vector into protoplasts followed by protein blot and ELISA analysis. This vector can be introduced into the genomic DNA of plant embryos such as cotton by particle gun bombardment followed by paromomycin selection to obtain cotton plants expressing the cry gene essentially as described in U.S. Pat. No. 5,424,412. For example, the plant transformation and expression vector can be introduced via co-bombardment with a hygromycin resistance conferring plasmid into transformation susceptible cotton tissue, followed by hygromycin selection, and regeneration. Transgenic cotton lines expressing the tIC851 protein can then identified by ELISA analysis. Progeny seed from these events can then subsequently be tested for protection from susceptible insect feeding.

The *B. thuringiensis* polypeptides described herein are primarily localized to the cytoplasm of the plant cell, and this cytoplasmic localization results in plants that are insecticidally effective. However, in certain embodiments, it may be advantageous to direct the *B. thuringiensis* polypeptide to other compartments of the plant cell. Localizing *B. thuringiensis* proteins in compartments other than the cytoplasm may result in less exposure of the *B. thuringiensis* proteins to cytoplasmic proteases leading to greater accumulation of the protein yielding enhanced insecticidal activity.

Utilizing SSU CTP sequences to localize crystal proteins to the chloroplast might also be advantageous. Localization of the *B. thuringiensis* crystal proteins to the chloroplast could protect these from proteases found in the cytoplasm. This could stabilize the proteins and lead to higher levels of accumulation of active toxin. cry genes containing the CTP may be used in combination with the SSU promoter or with other promoters such as CaMV35S.

In addition to tIC851 expression in plants as described herein, it is specifically intended that Cry22Aa and CryET70 be used alone or in combination with each other or in combinations along with tIC851 in plants to protect plants from boll weevil infestation and in particular combinations to prevent the onset of resistance of boll weevils to any of the proteins when used alone.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

6.0 REFERENCES

The following references, to the extent that they provide exemplary procedural or other details supplementary to those set forth herein, are specifically incorporated herein by reference:

U.S. Pat. No. 4,196,265, issued Apr. 1, 1980.
U.S. Pat. No. 4,237,224, issued Dec. 2, 1980.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,757,011, issued Jul. 12, 1988.
U.S. Pat. No. 4,766,203, issued Aug. 23, 1988.
U.S. Pat. No. 4,769,061, issued Sep. 6, 1988.
U.S. Pat. No. 4,771,131, issued Sep. 13, 1988.
U.S. Pat. No. 4,797,279, issued Jan. 10, 1989.
U.S. Pat. No. 4,800,159, issued Jan. 24, 1989.
U.S. Pat. No. 4,883,750, issued Nov. 28, 1989.
U.S. Pat. No. 4,910,016, issued Mar. 20, 1990.
U.S. Pat. No. 4,940,835, issued Feb. 23, 1990.
U.S. Pat. No. 4,943,674, issued Jul. 24, 1990.
U.S. Pat. No. 4,965,188, issued Oct. 23, 1990.
U.S. Pat. No. 4,966,765, issued Oct. 30, 1990.
U.S. Pat. No. 4,971,908, issued Nov. 20, 1990.
U.S. Pat. No. 4,987,071, issued Jan. 22, 1991.
U.S. Pat. No. 4,996,155, issued Feb. 26, 1991.
U.S. Pat. No. 4,999,192, issued Mar. 12, 1991.
U.S. Pat. No. 5,006,336, issued Apr. 9, 1991.
U.S. Pat. No. 5,024,837 issued Jun. 18, 1991.
U.S. Pat. No. 5,055,293, issued Oct. 8, 1991.
U.S. Pat. No. 5,055,294, issued Oct. 8, 1991.
U.S. Pat. No. 5,097,025, issued Mar. 17, 1992.
U.S. Pat. No. 5,106,739, issued Apr. 21, 1992.
U.S. Pat. No. 5,110,732, issued May 5, 1992.
U.S. Pat. No. 5,128,130, issued Oct. 15, 1991.
U.S. Pat. No. 5,139,954, issued Aug. 19, 1992.
U.S. Pat. No. 5,176,995, issued Oct. 15, 1991.
U.S. Pat. No. 5,177,011, issued Jan. 5, 1993.
U.S. Pat. No. 5,187,091, issued Oct. 15, 1991.
U.S. Pat. No. 5,264,364, issued Nov. 23, 1993.
U.S. Pat. No. 5,286,486, issued Feb. 15, 1994.
U.S. Pat. No. 5,334,711, issued Aug. 2, 1994.
U.S. Pat. No. 5,378,619, issued Jan. 3, 1995.
U.S. Pat. No. 5,384,253, issued Jan. 24, 1995.
U.S. Pat. No. 5,401,836, issued Ma 28, 1995.
U.S. Pat. No. 5,436,393, issued Jul. 25, 1995.
U.S. Pat. No. 5,441,884, issued Aug. 15, 1995.
U.S. Pat. No. 5,442,052, issued Aug. 15, 1995.
U.S. Pat. No. 5,447,858, issued Sep. 5, 1995.
U.S. Pat. No. 5,459,252, issued Oct. 17, 1995.
U.S. Pat. No. 5,491,288, issued Feb. 13, 1996.
U.S. Pat. No. 5,504,200, issued Apr. 2, 1996.
U.S. Pat. No. 5,530,196, issued Jun. 25, 1996.
U.S. Pat. No. 5,538,879, issued Jul. 23, 1996.
U.S. Pat. No. 5,576,198, issued Nov. 19, 1996.
U.S. Pat. No. 5,589,583, issued Dec. 31, 1996.
U.S. Pat. No. 5,589,610, issued Dec. 31, 1996.
U.S. Pat. No. 5,589,614, issued Dec. 31, 1996.
U.S. Pat. No. 5,595,896, issued Jan. 21, 1997.
U.S. Pat. No. 5,608,144, issued Mar. 4, 1997.
U.S. Pat. No. 5,614,399, issued Mar. 25, 1997.
U.S. Pat. No. 5,631,359, issued May 20, 1997.
U.S. Pat. No. 5,633,363, issued May 27, 1997.
U.S. Pat. No. 5,633,439, issued May 27, 1997.
U.S. Pat. No. 5,633,440, issued May 27, 1997.
U.S. Pat. No. 5,633,441, issued May 27, 1997.
U.S. Pat. No. 5,646,333, issued Jul. 8, 1997.
U.S. Pat. No. 5,659,124, issued Aug. 19, 1997.
U.S. Pat. No. 5,689,040, issued Nov. 18, 1997.
U.S. Pat. No. 5,689,049, issued Nov. 18, 1997.
U.S. Pat. No. 5,689,051, issued Nov. 18, 1997.
U.S. Pat. No. 5,689,056, issued Nov. 18, 1997.
U.S. Pat. No. 5,700,922, issued Dec. 23, 1997.

U.S. Pat. No. 5,712,112, issued Jan. 27, 1998.
Int. Pat. Appl. Publ. No. PCT/US87/00880.
Int. Pat. Appl. Publ. No. PCT/US89/01025.
Int. Pat. Appl. Publ. No. WO 84/02913.
Int. Pat. Appl. Publ. No. WO 88/10315.
Int. Pat. Appl. Publ. No. WO 89/06700.
Int. Pat. Appl. Publ. No. WO 91/03162.
Int. Pat. Appl. Publ. No. WO 92/07065.
Int. Pat. Appl. Publ. No. WO 93/15187.
Int. Pat. Appl. Publ. No. WO 93/23569.
Int. Pat. Appl. Publ. No. WO 94/02595.
Int. Pat. Appl. Publ. No. WO 94/13688.
Eur. Pat. Appl. Publ. No. EP0360257.
Eur. Pat. Appl. Publ. No. EP 320,308.
Eur. Pat. Appl. Publ. No. EP 329,822.
Eur. Pat. Appl. Publ. No. 92110298.4
Great Britain Pat. Appl. Publ. No. GB 2,202,328.
Abdullah et al., *Biotechnology*, 4:1087, 1986.
Abbott, "A method for computing the effectiveness of an insecticide," *J. Econ. Entomol.*, 18:265–267, 1925.
Adelman et al., *DNA*, 2(3):183–193, 1983.
Allen and Choun, "Large unilamellar liposomes with low uptake into the reticuloendothelial system," *FEBS Lett.*, 223:42–46, 1987.
Altschul, Stephen F. et al., "Basic local alignment search tool," *J. Mol. Biol.*, 215:403–410, 1990.
Armitage et al., *Proc. Natl. Acad. Sci. USA*, 94(23):12320–12325, 1997.
Arvidson et al., *Mol. Biol.*, 3:1533–1534, 1989.
Baum et al., *Appl. Environ. Microbiol.*, 56:3420–3428, 1990.
Baumnlein, Boerjan, Nagy, Panitz, Inze, Wobus, "Upstream sequences regulating legumin gene expression in heterologous transgenic plants," *Mol. Gen. Genet.*, 225(1):121–128, 1991.
Benbrook et al., *In: Proceedings Bio Expo 1986*, Butterworth, Stoneham, Mass., pp. 27–54, 1986.
Berhnard, *FEMS Microbiol. Lett.*, 33:261–265, 1986.
Berna and Bernier, "Regulated expression of a wheat germin gene in tobacco: oxalate oxidase activity and apoplastic localization of the heterologous protein," *Plant Mol. Biol.*, 33(3):417–429, 1997.
Boffa, Carpaneto, Allfrey, *Proc. Natl. Acad. Sci. USA*, 92:1901–1905, 1995.
Boffa, Morris, Carpaneto, Louissaint, Allfrey, *J. Biol. Chem.*, 271:13228–13233, 1996.
Bolivar et al., *Gene*, 2:95, 1977.
Boronat, Martinez, Reina, Puigdomenech, Palau, "Isolation and sequencing of a 28 kd gluteline-2 gene from maize: Common elements in the 5' flanking regions among zein and glutelin genes," *Plant Sci.*, 47:95–102, 1986.
Brown and Whiteley, *J. Bacteriol.*, 174:549–557, 1992.
Brussock and Currier, "Use of sodium dodecyl sulfate-polacryamide gel electrophoresis to quantify *Bacillus thuringiensis* δ-endotoxins," *In: Analytical Chemistry of Bacillus thuringiensis*, L. A. Hickle and W. L. Fitch, (Eds), American Chemical Society, Washington D.C., pp. 78–87, 1990.
Bytebier et al., *Proc. Natl. Acad. Sci. USA*, 84:5345, 1987.
Callis et al., *Genes and Development*, 1:1183, 1987.
Callis, Fromm, Walbot, "Introns increase gene expression in cultured maize cells," *Genes Devel.*, 1:1183–1200, 1987.
Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Capecchi, "High efficiency transformation by direct microinjection of DNA into cultured mammalian cells," *Cell*, 22(2):479–488, 1980.
Carlsson et al., *Nature*, 380:207, 1996.
Cashmore et al., *Gen. Eng. of Plants*, Plenum Press, New York, 29–38, 1983.
Cech et al., "In vitro splicing of the ribosomal RNA precursor of Tetrahymena: involvement of a guanosine nucleotide in the excision of the intervening sequence," *Cell*, 27:487–496, 1981.
Chambers et al., *J. Bacteriol.*, 173:3966–3976, 1991.
Chang et al., *Nature*, 375:615, 1978.
Chau et al., *Science*, 244:174–181, 1989.
Chen et al., *Nucl. Acids Res.*, 20:4581–9, 1992.
Cheng, Sardana, Kaplan, Altosaar, "*Agrobacterium*-transformed rice plants expressing synthetic cryIA(b) and cryIA(c) genes are highly toxic to striped stem borer and yellow stem borer," *Proc. Natl. Acad. Sci. USA*, 95(6): 2767–2772, 1998.
Chowrira and Burke, *Nucl. Acids Res.*, 20:2835–2840, 1992.
Christensen et al., *J. Pept. Sci.*, 1(3):175–183, 1995.
Christensen, Sharrock, Quail, "Maize polyubiquitin genes: Structure, thermal perturbation of expression and transcript splicing, and promoter activity following transfer to protoplasts by electroporation," *Plant Mol. Biol.*, 18:675–689, 1992.
Clapp, "Somatic gene therapy into hematopoietic cells. Current status and future implications," *Clin. Perinatol.*, 20(1):155–168, 1993.
Collins and Olive, *Biochem.*, 32:2795–2799, 1993.
Conway and Wickens, *In: RNA Processing*, p. 40, Cold Spring Harbor Laboratory, Cold Spring Harbor, N.Y., 1988.
Corey, *Trends Biotechnol.*, 15(6):224–229, 1997.
Couvreur et al., "Nanocapsules, a new lysosomotropic carrier," *FEBS Lett.*, 84:323–326, 1977.
Couvreur, "Polyalkyleyanoacrylates as colloidal drug carriers," *Crit. Rev. Ther. Drug Carrier Syst.*, 5:1–20, 1988.
Crickmore et al., *Abstr. 28th Annu. Meet. Soc. Invert. Pathol.*, Cornell University, Ithaca, N.Y., 1995.
Cristou et al., *Plant Physiol.*, 87:671–674, 1988.
Curiel, Agarwal, Wagner, Cotten, "Adenovirus enhancement of transferrin-polylysine-mediated gene delivery," *Proc. Natl. Acad. Sci. USA*, 88(19):8850–8854, 1991.
Curiel, Wagner, Cotten, Bimstiel, Agarwal, Li, Loechel, and Hu, "High-efficiency gene transfer mediated by adenovirus coupled to DNA-polylysine complexes," *Hum. Gen. Ther.*, 3(2):147–154, 1992.
Daum, "Revision of two computer programs for probit analysis," *Bull. Entomol. Soc. Amer.*, 16:10–15, 1970.
de Barjac, *In: Microbial Control of Pests and Plant Diseases*, H. D. Burges, ed., Academic Press, London, 36–43, 1981.
Dean et al., *Nucl. Acids Res.*, 14(5):2229, 1986.
Dennis, Gerlach, Pryor, Bennetzen, Inglis, Llewellyn, Sachs, Ferl, Peackocock, "Molecular analysis of the alcohol dehydrogenase (Adhl) gene of maize," *Nucl. Acids Res.*, 12:3983–4000, 1984.
Dhir, Dhir, Hepburn, Widholm, "Factors affecting transient gene expression in electroporated Glycine-max protoplasts," *Plant Cell Rep.*, 10(2):106–110, 1991a.
Dhir, Dhir, Sturtevant, Widholm, "Regeneration of transformed shoots for electroporated soybean Glycine-max L. Merr. Protoplasts, *Plant Cell Rep.*, 10(2):97–101, 1991b.
Donovan et al., *Appl. Environ. Microbiol.*, 58:3921–3927, 1992.

Donovan et al., *Mol. Gen. Genet.*, 214:365–372, 1988.
Dropulic et al., *J. Virol.*, 66:1432–41, 1992.
Dueholm et al., *J. Org. Chem.*, 59:5767–5773, 1994.
Egholm et al., *Nature*, 365:566–568, 1993.
Eglitis and Anderson, "Retroviral vectors for introduction of genes into mammalian cells," *Biotechniques*, 6(7):608–614, 1988.
Eglitis, Kantoff, Kohn, Karson, Moen, Lothrop, Blaese, Anderson, "Retroviral-mediated gene transfer into hemopoietic cells," *Avd. Exp. Med. Biol.*, 241:19–27, 1988.
Eichenlaub, *J. Bacteriol.*, 138(2):559–566, 1979.
Elroy-Stein and Moss, *Proc. Natl. Acad. Sci. USA*, 87:6743–7, 1990.
English and Slatin, *Insect Biochem. Mol. Biol.*, 22:1–7, 1992.
Faktor, Kooter, Dixon, Lamb, "Functional dissection of a bean chalcone synthase gene promoter in transgenic tobacco plants reveals sequence motifs essential for floral expression," *Plant Mol. Biol.*, 32(5):849–859, 1996.
Ficker, Kirch, Eijlander, Jacobsen, Thompson, "Multiple elements of the S2-RNase promoter from potato (*Solanum tuberosum* L.) are required for cell type-specific expression in transgenic potato and tobacco," *Mol. Gen. Genet.*, 257(2):132–142, 1998.
Fiers et al., *Nature*, 273:113, 1978.
Footer, Engholm, Kron, Coull, Matsudaira, *Biochemistry*, 35:10673–10679, 1996.
Fraley et al., *Biotechnology*, 3:629, 1985.
Fraley et al., *Proc. Natl. Acad. Sci. USA*, 80:4803, 1983.
French, Janda, Ahiquist, "Bacterial gene inserted in an engineered RNA virus: efficient expression in monocotyledonous plant cells," *Science*, 231:1294–1297, 1986.
Frohman, In: *PCR™ Protocols: A Guide to Methods and Applications*, Academic Press, New York, 1990.
Fromm, Taylor, Walbot, "Expression of genes transferred into monocot and dicot plant cells by electroporation," *Proc. Natl. Acad. Sci. USA*, 82(17):5824–5828, 1985.
Fromm et al., *Nature*, 319:791–793, 1986.
Fujimura et al., *Plant Tiss. Cult. Lett.*, 2:74, 1985.
Fynan, Webster, Fuller, Haynes, Santoro, Robinson, "DNA vaccines: protective immunizations by parenteral, mucosal, and gene gun inoculations," *Proc. Natl. Acad. Sci. USA*, 90(24):11478–11482, 1993.
Gallie and Young, "The regulation of expression in transformed maize aleurone and endosperm protoplasts," *Plant Physiol.*, 106:929–939, 1994.
Gallie, Feder, Schimke, Walbot, "Post-transcriptional regulation in higher eukaryotes: the role of the reporter gene in controlling expression," *Mol. Gen. Genet.*, 228:258–264, 1991.
Gallie, Lucas, Walbot, "Visualizing mRNA expression in plant protoplasts: factors influencing efficient mRNA uptake and translation," *Plant Cell*, 1:301–311, 1989.
Gallie, Sleat, Turner, Wilson, "Mutational analysis of the tobacco mosaic virus 5'-leader for altered ability to enhance translation," *Nucl. Acids Res.*, 16:883–893, 1988.
Gallie, Sleat, Watts, Turner, Wilson, "A comparison of eukaryotic viral 5'-leader sequences as enhancers of mRNA expression in vivo," *Nucl. Acids Res.*, 15:8693–8711, 1987b.
Gallie, Sleat, Watts, Turner, Wilson, "The 5'-leader sequence of tobacco mosaic virus RNA enhances the expression of foreign gene transcripts in vitro and in vivo," *Nucl. Acids Res.*, 15:3257–3273, 1987a.
Gambacorti-Passerini et al., *Blood*, 88:1411–1417, 1996.
Gao and Huang, *Nucl. Acids Res.*, 21:2867–72, 1993.
Gawron-Burke and Baum, *Genet. Eng.*, 13:237–263, 1991.
Gefter et al., *Somat. Cell Genet.*, 3:231–236, 1977.
Gehrke, Auron, Quigley, Rich, Sonenberg, "5'-Conformation of capped alfalfa mosaic virus ribonucleic acid 4 may reflect its independence of the cap structure or of cap-binding protein for efficient translation," *Biochemistry*, 22:5157–5164, 1983.
Genovese and Milcarek, In: *RNA Processing*, p. 62, Cold Spring Harbor Laboratory, Cold Spring Harbor, N.Y., 1988.
Gil and Proudfoot, *Nature*, 312:473, 1984.
Gill et al., *J. Biol. Chem.*, 270:27277–27282, 1995.
Goding, "Monoclonal Antibodies: Principles and Practice," pp. 60–74. 2nd Edition, Academic Press, Orlando, Fla., 1986.
Goeddel et al., *Nature*, 281:544, 1979.
Goeddel et al., *Nucl. Acids Res.*, 8:4057, 1980.
Goelet, Lomonossoff, Butler, Akam, Gait, Karn, "Nucleotide sequence of tobacco mosaic virus RNA," *Proc. Natl. Acad. Sci. USA*, 79:5818–5822, 1982.
Gonzalez Jr. et al., *Proc. Natl. Acad. Sci USA*, 79:6951–6955, 1982.
Good and Nielsen, *Antisense Nucleic Acid Drug Dev.*, 7(4):431–437, 1997.
Graham, Craig, Waterhouse, "Expression patterns of vascular-specific promoters ROIC and Sh in transgenic potatoes and their use in engineering PLRV-resistant plants," *Plant Mol. Biol.*, 33(4):729–735, 1997.
Graham, F. L., and van der Eb, A. J., "Transformation of rat cells by DNA of human adenovirus 5," *Virology*, 54(2):536–539, 1973.
Green, *Nucl. Acids Res.*, 16(1):369. 1988.
Griffith et al., *J. Am. Chem. Soc.*, 117:831–832, 1995.
Grochulski et al., *J. Mol. Biol.*, 254:447–464, 1995.
Grosset, Alary, Gautier, Menossi, Martinez-Izquierdo, Joudrier, "Characterization of a barley gene coding for an alpha-amylase inhibitor subunit (Cmd protein) and analysis of its promoter in transgenic tobacco plants and in maize kernels by microprojectile bombardment," *Plant Mol. Biol.*, 34(2):331–338, 1997.
Guerrier-Takada et al., *Cell*, 35:849, 1983.
Haaima, Lohse, Buchardt, Nielsen, *Angew. Chem., Int. Ed. Engl.*, 35:1939–1942, 1996.
Hampel and Tritz, *Biochem.*, 28:4929, 1989.
Hampel et al., *Nucl. Acids Res.*, 18:299, 1990.
Hanvey et al., *Science*, 258:1481–1485, 1992.
Harlow and Lane, "Antibodies: A Laboratory Manual," Cold Spring Harbor Laboratory, Cold Spring Harbor, N.Y., 1988.
Henry-Michelland et al., "Attachment of antibiotics to nanoparticles; Preparation, drug-release and antimicrobial activity in vitro, *Int. J. Pharm.*, 35:121–127, 1987.
Herrnstadt et al., *Bio/Technology*, 4:305–308, 1986.
Herrnstadt et al., *Gene*, 57:37–46, 1987.
Hess et al., *J. Adv. Enzyme Reg.*, 7:149, 1968.
Hess, *Intern Rev. Cytol.*, 107:367, 1987.
Hilber, Bodmer, Smith, Koller, "Biolistic transformation of conidia of *Botryotinia fuckeliana*," *Curr. Genet.*, 25(2):124–127, 1994.
Hitzeman et al., *J. Biol. Chem.*, 255:2073, 1980.
Höfte and Whiteley, *Microbiol. Rev.*, 53:242–255, 1989.
Höfte et al. *Nucl. Acids Res.*, 15:7183, 1987.
Holland et al., *Biochemistry*, 17:4900, 1978.
Honee et al., *Mol. Microbiol.*, 5:2799–2806, 1991.
Hoover et al., (Eds.), "Remington's Pharmaceutical Sciences," 15th Edition, Mack Publishing Co., Easton, Pa., 1975.

Horsch, Fry, Hoffmann, Eichholtz, Rogers, Fraley, "A simple and general method for transferring genes into plants," *Science*, 227(4691):1229–1231, 1985.

Horton et al., *Gene*, 77:61–68, 1989.

Huang, An, McDowell, McKinney, Meagher, "The *Arabidopsis* ACT11 action gene is strongly expressed in tissues of the emerging inflorescence, pollen and developing ovules," *Plant Mol. Biol.*, 33(1):125–139, 1997.

Hudspeth and Grula, "Structure and expression of the maize gene encoding the phosphoenolpyruvate carboxylase isozyme involved in C4 photosynthesis," *Plant Mol. Biol.*, 12:579–589, 1989.

Hyrup and Nielsen, *Bioorg. Med. Chem.*, 1996.

Ingelbrecht, Herman, Dekeyser, Van Montagu, Depicker, "Different 3' end regions strongly influence the level of gene expression in plant cells," *Plant Cell*, 1:671–680, 1989.

Itakura et al., *Science*, 198:1056, 1977.

Jaeger et al., *Proc. Natl. Acad. Sci. USA*, 86:7706–7710, 1989.

Jameson and Wolf, "The Antigenic Index: A Novel Algorithm for Predicting Antigenic Determinants," *Compu. Appl. Biosci.*, 4(1):181–6, 1988.

Jensen et al., *Biochemistry*, 36(16):5072–5077, 1997.

Jobling and Gehrke, "Enhanced translation of chimaeric messenger RNAs containing a plant viral untranslated leader sequence," *Nature*, 325:622–625, 1987.

Johnston and Tang, "Gene gun transfection of animal cells and genetic inmunization," *Methods Cell. Biol.*, 43(A):353–365, 1994.

Jones, Dean, Gidoni, Gilbert, Bond-Nutter, Lee, Bedbrook, Dunsmuir, "Expression of bacterial chitinase protein in tobacco leaves using two photosynthetic gene promoters," *Mol. Gen. Genet.*, 212:536–542, 1988.

Jones, *Genetics*, 85:12 1977.

Jorgensen et al., *Mol. Gen. Genet.*, 207:471, 1987.

Joshi, "An inspection of the domain between putative TATA box and translation start site in 79 plant genes," *Nucl. Acids Res.*, 15:6643–6653, 1987.

Kaiser and Kezdy, *Science*, 223:249–255, 1984.

Kashani-Saber et al., *Antisense Res. Dev.*, 2:3–15, 1992.

Keller et al., *EMBO J.*, 8:1309–14, 1989.

Kingsman et al., *Gene*, 7:141, 1979.

Klee, Yanofsky, Nester, "Vectors for transformation of higher plants," *Bio-Technology*, 3(7):637–642, 1985.

Klein et al., *Nature*, 327:70, 1987.

Klein et al., *Proc. Natl. Acad. Sci. USA*, 85:8502–8505, 1988.

Knight et al., *J. Biol. Chem.*, 270:17765–17770, 1995.

Koch et al., *Tetrahedron Lett.*, 36:6933–6936, 1995.

Kohler and Milstein, *Eur. J. Immunol.*, 6:511–519, 1976.

Kohler and Milstein, *Nature*, 256:495–497, 1975.

Koppelhus, *Nucleic Acids Res.*, 25(11):2167–2173, 1997.

Korn and Queen, *DNA*, 3:421–436, 1984.

Kozak, *Nature*, 308:241–246, 1984.

Koziel, Beland, Bowman, Carozzi, Crenshaw, Crossland, Dawson, Desai, Hill, Kadwell, Launis, Lewis, Maddox, McPherson, Meghji, Merlin, Rhodes, Warren, Wright, Evola, "Field performance of elite transgenic maize plants expressing an insecticidal protein derived from *Bacillus thuringiensis*, *Bio/technology*, 11:194–200, 1993.

Koziel, Carozzi, Desai, "Optimizing expression of transgenes with an emphasis on post-transcriptional events," *Plant Mol. Biol.*, 32(102):393–405, 1996.

Koziel, Fujimoto, Izawa, Shimamoto, "Anaerobic-induction and tissue

Kremsky et al., *Tetrahedron Lett.*, 37:4313–4316, 1996.

Krieg et al., *AnzSchaed. lingskde, Pflanzenschutz, Umwelrschulz*, 57:145–150, 1984.

Krieg et al., In: *Zangew. Ent.*, 96:500–508, 1983.

Krieg et al., *J. Appl. Ent.*, 104:417–424, 1987.

Kuby, "Immunology" 2nd Edition. W.H. Freeman & Company, New York, 1994.

Kunkel, Roberts, Zakour, "Rapid and efficient site-specific mutagenesis without phenotypic selection," *Methods Enzymol.*, 154:367–382, 1987.

Kwoh, Davis, Whitfield, Chappelle, DiMichele, Gingeras, "Transcription-based amplification system and detection of amplified human immunodeficiency virus type 1 with a bead-based sandwich hybridization format," *Proc. Natl. Acad. Sci. USA*, 86(4):1173–1177, 1989.

Kyozuka, Fujimoto, Izawa, Shimamoto, "Anaerobic induction and tissue-specific expression of maize Adh1 promoter in transgenic rice plants and their progeny," *Mol. Gen. Genet.*, 228(1–2):40–48, 1991.

Kyte and Doolittle, "A simple method for displaying the hydropathic character of a protein," *J. Mol. Biol.*, 157(1):105–132, 1982.

L'Huillier et al., *EMBO J.*, 11:4411–8, 1992.

Ladd Jr., *J. Econ. Entomol.*, 79:00668–671, 1986.

Lambert et al., *Appl. Environ. Microbiol.*, 58:2536–2642, 1992b.

Lambert et al., *Gene*, 110:131–132, 1992a.

Landsdorp et al., *Hum. Mol. Genet.*, 5:685–691, 1996.

Langridge et al., *Proc. Natl. Acad. Sci. USA*, 86:3219–3223, 1989.

Lee et al., *Biochem. Biophys. Res. Comm.*, 216:306–312, 1995.

Lieber et al., *Methods Enymol.*, 217:47–66, 1993.

Lindstrom et al., *Developmental Genetics*, 11:160, 1990.

Lisziewicz et al., *Proc. Natl. Acad. Sci. U.S.A.*, 90:8000–4, 1993.

Lorz et al, *Mol. Gen. Genet.*, 199:178, 1985.

Lu, Xiao, Clapp, Li, Broxmeyer, "High efficiency retroviral mediated gene transduction into single isolated immature and replatable CD34(3+) hematopoietic stem/progenitor cells from human umbilical cord blood," *J. Exp. Med.*, 178(6):2089–2096, 1993.

Luehrsen and Walbot, "Intron enhancement of gene expression and the splicing efficiency of introns in maize cells," *Mol. Gen. Genet.*, 225:81–93, 1991.

Luo et al., *Plant Mol. Biol. Reporter*, 6:165, 1988.

Lutcke, Chow, Mickel, Moss, Kern, Scheele, "Selection of AUG initiation codons differs in plants and animals," *EMBO J.*, 6:43–48, 1987.

Maas, Laufs, Grant, Korfhage, Werr, "The combination of a novel stimulatory element in the first exon of the maize shrunken-1 gene with the following intron enhances reporter gene expression 1000-fold," *Plant Mol. Biol.*, 16:199–207, 1991.

Macaluso and Mettus, *J. Bacteriol.*, 173:1353–1356, 1991.

Maddock et al., *Third International Congress of Plant Molecular Biology*, Abstract 372, 1991.

Maloy, "Experimental Techniques in Bacterial Genetics" Jones and Bartlett Publishers, Boston, Mass., 1990.

Maloy et al., "Microbial Genetics" 2nd Edition. Jones and Barlett Publishers, Boston, Mass., 1994.

Maniatis et al., "Molecular Cloning: a Laboratory Manual," Cold Spring Harbor Laboratory, Cold Spring Harbor, N.Y., 1982.

Marcotte et al., *Nature*, 335:454, 1988.

Mascerenhas, Mettler, Pierce, Lowe, "Intron mediated enhancement of heterologous gene expression in maize," *Plant Mol. Biol.*, 15:913–920, 1990.

Masson et al., *J. Biol. Chem.*, 270:20309–20315, 1995.

McBride, Svab, Schaaf, Hogan, Stalker, Maliga, "Amplification of a chimeric *Bacillus* gene in chloroplasts leads to an extraordinary level of an insecticidal protein in tobacco," *Bio/technology*, 13:362–365, 1995.

McCabe et al., *Biotechnology*, 6:923, 1988.

McDevitt et al., *Cell*, 37:993–999, 1984.

McElroy, Zhang, Wu, "Isolation of an efficient promoter for use in rice transformation," *Plant Cell*, 2:163–171, 1990.

McPherson et al., *Bio/Technology*, 6:61–66, 1988.

Mettus and Macaluso, *Appl. Environ. Microbiol.*, 56:1128–1134, 1990.

Michael, *Biotechniques*, 16:410–412, 1994.

Mollegaard, Buchardt, Egholm, Nielsen, *Proc. Natl. Acad. Sci. USA*, 91:3892–3895, 1994.

Nawrath, Poirier, Somerville, "Targeting of the polyhydroxybutyrate biosynthetic pathway to the plastids of *Arabidopsis thaliana* results in high levels of polymer accumulation," *Proc. Natl. Acad. Sci. USA*, 91:12760–12764, 1994.

Neilsen, In: *Perspectives in Drug Discovery and Design 4*, Escom Science Publishers, pp. 76–84, 1996.

Neuhaus et al., *Theor. Appl. Genet.*, 75:30, 1987.

Nielsen et al., *Anticancer Drug Des.*, 8(1):53–63, 1993b.

Nielsen, Egholm, Berg, Buchardt, *Science*, 254:1497–1500, 1991.

Norton et al., *Plasmid*, 13:211–214, 1985.

Norton, Piatyszek, Wright, Shay, Corey, *Nat. Biotechnol.*, 14:615–620, 1996.

Norton, Waggenspack, Varnum, Corey, *Bioorg. Med. Chem.*, 3:437–445, 1995.

Oard, Paige, Dvorak, "Chimeric gene expression using maize intron in cultured cells of breadwheat," *Plant Cell. Rep.*, 8:156–160, 1989.

Odell et al., *Nature*, 313:810, 1985.

Ohkawa, Yuyama, Taira, "Activities of HIV-RNA targeted ribozymes transcribed from a 'shot-gun' type ribozyme-trimming plasmid," *Nucl. Acids Symp. Ser.*, 27:15–6, 1992.

Ojwang et al., *Proc. Natl. Acad. Sci. USA*, 89:10802–6, 1992.

Omirulleh et al., *Plant Mol. Biol.*, 21:415–428, 1993.

Orum, Nielsen, Egholm, Berg, Buchardt, Stanley, *Nucl. Acids Res.*, 21:5332–5336, 1993.

Orum, Nielsen, Jorgensen, Larsson, Stanley, Koch, *BioTechniques*, 19:472–480, 1995.

Pandey and Marzluff, In "RNA Processing," p. 133, Cold Spring Harbor Laboratory, Cold Spring Harbor, N.Y., 1987.

Pardridge, Boado, Kang, *Proc. Natl. Acad. Sci. USA*, 92:5592–5596, 1995.

Pena et al., *Nature*, 325:274, 1987.

Perlak, Deaton, Armstrong, Fuchs, Sims, Greenplate, Fischhoff, "Insect resistant cotton plants," *Bio/Technology*, 8:939–943, 1990.

Perlak, Fuchs, Dean, McPherson, Fischhoff, "Modification of the coding sequence enhances plant expression of insect control protein genes," *Proc. Nail. Acad. Sci. USA*, 88:3324–3328, 1991.

Perlak, Stone, Muskopf, Peterson, Parker, McPherson, Wyman, Love, Reed, Biever, Fischhoff, "Genetically improved potatoes: protection from damage by Colorado potato beetles," *Plant Mol. Biol.*, 22:313–321, 1993.

Perrault et al, *Nature*, 344:565, 1990.

Perrotta and Been, *Biochem.*, 31:16, 1992.

Perry-O'Keefe, Yao, Coull, Fuchs, Egholm, *Proc. Natl. Acad. Sci. USA*, 93:14670–14675, 1996.

Petersen, Jensen, Egholm, Nielsen, Buchardt, *Bioorg. Med. Chem. Lett.*, 5:1119–1124, 1995.

Pieken et al., *Science*, 253:314, 1991.

Poogin and Skryabin, "The 5' untranslated leader sequence of potato virus X RNA enhances the expression of the heterologous gene in vivo," *Mol. Gen. Genet.*, 234:329–331, 1992.

Poszkowski et al., *EMBO J.*, 3:2719, 1989.

Potrykus et al., *Mol. Gen. Genet.*, 199:183, 1985.

Poulsen et al., *Mol. Gen. Genet.*, 205:193–200, 1986.

Prokop and Bajpai, *Ann. N.Y. Acad. Sci.*, 646, 1991.

Rogers et al., In: *Methods For Plant Molecular Biology*, Weissbach and Weissbach, eds., Academic Press Inc., San Diego, Calif. 1988.

Rogers et al., *Methods Enymol.*, 153:253–277, 1987.

Rose, *Anal. Chem.*, 65(24):3545–3549, 1993.

Rossi et al., *Aids Res. Hum. Retrovir.*, 8:183, 1992.

Rupar et al., *Appl. Environ. Microbiol.*, 57:3337–3344, 1991.

Ruskowski et al., *Cancer*, 80(12 Suppl):2699–2705, 1997.

Russell and Fromm, "Tissue-specific expression in transgenic maize for four endosperm promoters from maize and rice," *Transgenic Res.*, 6(2):157–168, 1997.

Sadofsky and Alwine, *Mol. Cell. Biol.*, 4(8):1460–1468, 1984.

Sambrook et al., "Antibodies: A Laboratory Manual," Cold Spring Harbor Laboratory, Cold spring Harbor, N.Y., 1989a.

Sambrook et al., "Molecular Cloning: A Laboratory Manual," Cold Spring Harbor Laboratory, Cold Spring Harbor, N.Y., 1989b.

Sanger et al., "DNA sequencing with chain-terminating inhibitors," *Proc. Natl. Acad. Sci. USA*, 74(12):5463–5467, 1977.

Saville and Collins, *Cell*, 61:685–696, 1990.

Saville and Collins, *Proc. Natl. Acad. Sci. USA*, 88:8826–8830, 1991.

Scanlon et al., *Proc. Natl. Acad. Sci. USA*, 88:10591–5, 1991.

Scaringe et al., *Nucl. Acids Res.*, 18:5433–5441, 1990.

Seeger et al., *Biotechniques*, 23(3):512–517, 1997.

Segal, "Biochemical Calculations" 2nd Edition. John Wiley & Sons, New York, 1976.

Sekar et al., *Proc. Natl. Acad. Sci. USA*, 84:7036–7040, 1987.

Shaw and Kamen, *Cell*, 46:659–667, 1986.

Shaw and Kamen, In: "RNA Processing", p. 220, Cold Spring Harbor Laboratory, Cold Spring Harbor, N.Y., 1987.

Sick et al., *Nucl. Acids Res.*, 18:1305, 1990.

Simpson, *Science*, 233:34, 1986.

Sleat, Gallie, Jefferson Bevan, Turner, Wilson, "Characterization of the 5'-leader sequence of tobacco mosaic virus RNA as a general enhancer of translation in vitro," *Gene*, 217:217–225, 1987.

Sleat, Hull, Turner, Wilson, "Studies on the mechanism of translational enhancement by the 5'-leader sequence of tobacco mosaic virus RNA," *Eur. J. Biochem.*, 175: 75–86, 1988.

Southern, *J. Mol. Biol.*, 98:503–517, 1975.

Spielmann et al., *Mol. Gen. Genet.*, 205:34, 1986.

Stetsenko, Lubyako, Potapov, Azhikina, Sverdlov, *Tetrahedron Lett.*, 37:3571–3574, 1996.

Stone et al., Insect rearing and the development of bioengineered crops. In T. E. Anderson & N. C. Leppla [eds]. Advances in insect rearing for research and pest management. West-view, Boulder, Colo. 1991.
Taira et al., *Nucl. Acids Res.*, 19:5125–30, 1991.
Tanaka, Mita, Ohta, Kyozuka, Shimamoto, Nakamura, "Enhancement of foreign gene expression by a dicot intron in rice but not in tobacco is correlated with an increased level of mRNA and an efficient splicing of the intron," *Nucl. Acids Res.*, 18:6767–6770, 1990.
Thiede, Bayerdorffer, Blasczyk, Wittig, Neubauer, *Nucleic Acids Res.*, 24:983–984, 1996.
Thisted, Just, Petersen, Hyldig-Nielsen, Godtfredsen, *Cell Vision*, 3:358–363, 1996.
Thomson et al., *Tetrahedron*, 51:6179–6194, 1995.
Tomic, Sunjevaric, Savtchenko, Blumenberg, "A rapid and simple method for introducing specific mutations into any position of DNA leaving all other positions unaltered," *Nucl. Acids Res.*, 18(6):1656, 1990.
Toriyama et al., *Theor Appl. Genet.*, 73:16, 1986.
Treacy, Hattori, Prud'homme, Barbour, Boutilier, Baszczynski, Huang, Johnson, Miki, "Bnm1, a *Brassica* pollen-specific gene," *Plant Mol. Biol.*, 34(4):603–611, 1997.
Uchimiya et al., *Mol. Gen. Genet.*, 204:204, 1986.
Ulmann, Will, Breipohl, Langner, Ryte, *Angew. Chem., Int. Ed. Engl.*, 35:2632–2635, 1996.
Upender, Raj, Weir, "Megaprimer method for in vitro mutagenesis using parallel templates," *Biotechniques*, 18:29–31, 1995.
Usman et al., *J. Am. Chem. Soc.*, 109:7845–7854, 1987.
Usman and Cedergren, *TIBS*, 17:34, 1992.
Van Camp, Herouart, Willekens, Takahashi, Saito, Van Montagu, Inze, "Tissue-specific activity of two manganese superoxide dismutase promoters in transgenic tobacco," *Plant Physiol.*, 112(2):525–535, 1996.
Van Tunen et al., *EMBO J.*, 7:1257, 1988.
Vander, Van Montagu, Inze, Boerjan, "Tissue-specific expression conferred by the S-adenosyl-L-methionine synthetase promoter of *Arabidopsis thaliana* in transgenic poplar," *Plant Cell Physiol.*, 37(8):1108–1115, 1996.
Vasil et al., "Herbicide-resistant fertile transgenic wheat plants obtained by microprojectile bombardment of regenerable embryogenic callus," *Biotechnology*, 10:667–674, 1992.
Vasil, *Biotechnology*, 6:397, 1988.
Vasil, Clancy, Ferl, Vasil, Hannah, "Increased gene expression by the first intron of maize shrunken-1 locus in grass species," *Plant Physiol.*, 91:1575–1579, 1989.
Velten et al., *EMBO J.*, 3:2723–2730, 1984.
Velten and Schell, *Nucl. Acids Res.*, 13:6981–6998, 1985.
Ventura et al., *Nucl. Acids Res.*, 21:3249–55, 1993.
Veselkov, Demidov, Nielsen, Frank-Kamenetskii, *Nucl. Acids Res.*, 24:2483–2487, 1996.
Vickers, Griffith, Ramasamy, Risen, Freier, *Nucl. Acids Res.*, 23:3003–3008, 1995.
Vodkin et al., *Cell*, 34:1023, 1983.
Vogel, Dawe, Freeling, "Regulation of the cell type-specific expression of maize Adh1 and Sh1 electroporation-directed gene transfer into protoplasts of several maize tissues," *J. Cell. Biochem.*, (Suppl. 0) 13:Part D, 1989.
Wagner et al., "Coupling of adenovirus to transferrin-polylysine/DNA complexes greatly enhances receptor-mediated gene delivery and expression of transfected genes," *Proc. Natl. Acad. Sci. USA*, 89(13):6099–6103, 1992.
Walker, Little, Nadeau, Shank, "Isothermal in vitro amplification of DNA by a restriction enzyme/DNA polymerase system," *Proc. Natl. Acad. Sci. USA*, 89(1):392–396, 1992.
Wang, *J. Am. Chem. Soc.*, 118:7667–7670, 1996.
Watson, "Fluid and electrolyte disorders in cardiovascular patients," *Nurs. Clin. North Am.*, 22(4):797–803, 1987.
Webb and Hurskainen, *J. Biomol. Screen.*, 1:119–121, 1996.
Weerasinghe et al., *J. Virol.*, 65:5531–4, 1991.
Weissbach and Weissbach, *Methods for Plant Molecular Biology*, (eds.), Academic Press, Inc., San Diego, Calif., 1988.
Wenzler et al., *Plant Mol. Biol.*, 12:41–50, 1989.
Wickens and Stephenson, *Science*, 226:1045, 1984.
Wickens et al., In: "RNA Processing," p. 9, Cold Spring Harbor Laboratory, Cold Spring Harbor, N.Y., 1987.
Wilson, Flint, Deaton, Fischhoff, Perlak, Armstrong, Fuchs, Berberich, Parks, Stapp, "Resistance of cotton lines containing a *Bacillus thuringiensis* toxin to pink bollworm (Lepidopteran: Gelechiidae) and other insects," *J. Econ. Entomol.*, 4:1516–1521, 1992.
Wolf et al., *Compu. Appl. Biosci.*, 4(1):187–91 1988.
Wong and Neumann, "Electric field mediated gene transfer," *Biochim. Biophys. Res. Commun.*, 107(2):584–587, 1982.
Woolf et al., *Proc. Natl. Acad. Sci. USA*, 89:7305–7309, 1992.
Wu and Dean, "Functional significance of loops in the receptor binding domain of *Bacillus thuringiensis* CryIIIA delta-endotoxin," *J. Mol. Biol.*, 255(4):628–640, 1996.
Yamada et al., *Plant Cell Rep.*, 4:85, 1986.
Yang et al., *Proc. Natl. Acad. Sci. USA*, 87:4144–48, 1990.
Yin, Chen, Beachy, "Promoter elements required for phloem-specific gene expression from the RTBV promoter in rice," *Plant J.*, 12(5):1179–1188, 1997b.
Yin, Zhu, Dai, Lamb, Beachy, "RF2a, a bZIP transcriptional activator of the phloem-specific rice tungro bacilliform virus promoter, functions in vascular development," *EMBO J.*, 16(17):5247–5259, 1997a.
Yu et al., *Proc. Natl. Acad. Sci. USA*, 90:6340–4, 1993.
Zatloukal, Wagner, Cotten, Phillips, Plank, Steinlein, Curiel, Bimstiel, "Transferrinfection: a highly efficient way to express gene constructs in eukaryotic cells," *Ann. N.Y. Acad. Sci*, 660:136–153, 1992.
Zhou et al., *Methods Enzymol.*, 101:433, 1983.
Zhou et al., *Mol. Cell Biol.*, 10:4529–37, 1990.

What is claimed is:

1. An isolated and purified polynucleotide sequence encoding tIC851 comprising the polypeptide of SEQ ID NO: 8.

2. The polynucleotide sequence of claim 1 wherein said polypeptide exhibits insecticidal activity when provided orally to a susceptible insect larva.

3. The polynucleotide sequence of claim 2 wherein said polypeptide exhibits insecticidal activity when provided in an orally administrable diet or compositian to a Coleopteran insect larva.

4. The polynucleotide sequence of claim 3 wherein said insect larva is a cotton boll weevil larva.

5. The polynucleotide sequence of claim 1 comrprising nucleotides 28 to 1923 of SEQ ID NO: 7.

6. A vector for use in transforming a host cell, wherein said vector comprises a polynucleotide sequence encoding the polypeptide as set forth in SEQ ID NO: 8.

7. The vector of claim 6, wherein said vector is plasmid pIC17501.

8. The vector of claim 6 wherein said host cell is selected from the group consisting of a plant cell and a bacterial cell.

9. A plant tissue transformed with a polynucleotide sequence which expresses the polypeptide of SEQ ID NO: 8, wherein said tissue is selected from the group consisting of a plant cell, an embryonic plant tissue, plant calli, a leaf, a plant stem, a plant root, a plant flower, a fruit, a fruiting body, a boll, and a plant seed.

10. The plant tissue of claim 9 wherein said tissue comprises said polypeptide present in a Coleopteran insect inhibitory effective amount.

11. The plant tissue of claim 10 wherein said Coleopteran insect is a cotton boll weevil.

12. The plant tissue of claim 9 selected from the group of plants consisting of corn, wheat, cotton, soybean, oat, rice, rye, sorghum, sugarcane, tomato, tobacco, kapok, flax, potato, barley, turf grass, pasture grass, berry bush, fruit tree, legume, vegetable, ornamental plant, shrub, cactus, succulent, deciduous tree, and evergreen tree.

13. A method of making a transgenic plant resistant to Coleopteran insect infestation comprising incorporating into a genome of a plant cell a polynucleotide comprising at least a plant functional promoter operably linked to a nucleotide sequence encoding the polypeptide of SEQ ID NO: 8, isolating and propagating a plant cell transformed with said polynucleotide, regenerating a plant from said plant cell transformed with said polynucleotide, and propagating said plant from progeny, wherein said plant expresses an insecticidally effective amount of said polypeptide from said polynucleotide.

14. The method of claim 13 wherein said plant cell is either a monocot or a dicot plant cell.

15. The method of claim 14 wherein said monocot plant cell is selected from the group of plant cells consisting of corn, wheat, rye, barley, rice, banana, sugarcane, oat, flax, turf grass, pasture grass, and sorghum cells.

16. The method of claim 14 wherein said dicot plant cell is selected from the group of plant cells consisting of cotton, soybean, canola, potato, tomato, fruit tree, shrub, vegetable, and berry cells.

17. A plant cell transformed with a polynucleotide sequence encoding tIC851 comorising SEQ ID NO: 8 and a polynucleotide sequence encoding one or more of the polypeptides as set forth in SEQ ID NO: 2 (CryET70) and SEQ ID NO: 10 (Cry22Aa) or insecticidal fragments thereof, wherein said cell produces an amount of said polypeptides effective for controlling a Coleopteran insect pest infestation.

18. The plant cell of claim 17 wherein said Coleopteran insect pest is a cotton boll weevil and said plant cell is a cotton plant cell.

* * * * *

SEQUENCE LISTING

<160> NUMBER OF SEQ ID NOS: 22

<210> SEQ ID NO 1
<211> LENGTH: 2148
<212> TYPE: DNA
<213> ORGANISM: Bacillus thuringiensis

```
<220> FEATURE:
<221> NAME/KEY: CDS
<222> LOCATION: (1)..(2148)

<400> SEQUENCE: 1 atg aaa gat tca att tca aag gga tat gat gaa ata aca gtg cag gca      48
Met Lys Asp Ser Ile Ser Lys Gly Tyr Asp Glu Ile Thr Val Gln Ala
1               5                   10                  15 agt gat tat att gat att tca att ttt caa acg aat gga tct gca aca      96
Ser Asp Tyr Ile Asp Ile Ser Ile Phe Gln Thr Asn Gly Ser Ala Thr
            20                  25                  30 ttt aat tca acc act att aca act tta acg caa gct aca aat agt caa     144
Phe Asn Ser Thr Thr Ile Thr Thr Leu Thr Gln Ala Thr Asn Ser Gln
        35                  40                  45 gcg gga gca att ggg aag aca gct tta gat atg aga cat gat ttt act     192
Ala Gly Ala Ile Gly Lys Thr Ala Leu Asp Met Arg His Asp Phe Thr
    50                  55                  60 ttt aga gct att ttt ctt gga act aaa agt aat gga gca gat ggt att     240
Phe Arg Ala Ile Phe Leu Gly Thr Lys Ser Asn Gly Ala Asp Gly Ile
65                  70                  75                  80 gcg ata gca ttt cat aga gga tca att ggt ttt gtt ggg gag aag ggt     288
Ala Ile Ala Phe His Arg Gly Ser Ile Gly Phe Val Gly Glu Lys Gly
                85                  90                  95 gga gga ggg att tta ggc gcc cta aaa ggt ata gga ttt gaa tta gac     336
Gly Gly Gly Ile Leu Gly Ala Leu Lys Gly Ile Gly Phe Glu Leu Asp
            100                 105                 110 aca tat gcg aat gct cct caa gat gaa caa gga gat tct ttt gga cat     384
Thr Tyr Ala Asn Ala Pro Gln Asp Glu Gln Gly Asp Ser Phe Gly His
        115                 120                 125 gga gca atg aga ggc cta ttc cct ggt ttc cca aat gga tat cca cat     432
Gly Ala Met Arg Gly Leu Phe Pro Gly Phe Pro Asn Gly Tyr Pro His
    130                 135                 140 gct ggt ttt gta agt acg gat aaa aat aga ggt tgg tta tct gcc tta     480
Ala Gly Phe Val Ser Thr Asp Lys Asn Arg Gly Trp Leu Ser Ala Leu
145                 150                 155                 160 gct cag atg cag cga ata gct gct cca aat ggg cgt tgg aga cgt ctg     528
Ala Gln Met Gln Arg Ile Ala Ala Pro Asn Gly Arg Trp Arg Arg Leu
                165                 170                 175 gcg att cat tgg gat gct cgc aat aaa aaa tta act gca aac ctt gag     576
Ala Ile His Trp Asp Ala Arg Asn Lys Lys Leu Thr Ala Asn Leu Glu
            180                 185                 190 gat tta act ttt aat gat tca acg gta tta gtg aaa cca cgt act cca     624
Asp Leu Thr Phe Asn Asp Ser Thr Val Leu Val Lys Pro Arg Thr Pro
        195                 200                 205 aga tat gca aga tgg gag tta tca aat cct gca ttt gaa ctt gat caa     672
Arg Tyr Ala Arg Trp Glu Leu Ser Asn Pro Ala Phe Glu Leu Asp Gln
    210                 215                 220 aag tat act ttt gtt att ggt tca gcg acg ggt gca tct aat aac cta     720
Lys Tyr Thr Phe Val Ile Gly Ser Ala Thr Gly Ala Ser Asn Asn Leu
225                 230                 235                 240 cat cag att ggt att ata gaa ttt gat gca tac ttt act aaa ccg aca     768
His Gln Ile Gly Ile Ile Glu Phe Asp Ala Tyr Phe Thr Lys Pro Thr
                245                 250                 255 ata gag gcg aat aat gta agt gtt ccg gtg gga gca aca ttt aat ccg     816
Ile Glu Ala Asn Asn Val Ser Val Pro Val Gly Ala Thr Phe Asn Pro
            260                 265                 270 aaa aca tat cca gga ata aat tta aga gca act gat gaa ata gat ggt     864
Lys Thr Tyr Pro Gly Ile Asn Leu Arg Ala Thr Asp Glu Ile Asp Gly
        275                 280                 285 gat ttg aca tct gaa att att gtg aca gat aat aat gtt aat acg tcg     912
```

```
Asp Leu Thr Ser Glu Ile Ile Val Thr Asp Asn Asn Val Asn Thr Ser
    290                 295                 300 aaa tct ggt gtg tat aat gtg acg tat tat gta aag aat agc tat ggg        960
Lys Ser Gly Val Tyr Asn Val Thr Tyr Tyr Val Lys Asn Ser Tyr Gly
305                 310                 315                 320 gaa agt gat gaa aaa aca atc gaa gta act gtg ttt tca aac cct aca       1008
Glu Ser Asp Glu Lys Thr Ile Glu Val Thr Val Phe Ser Asn Pro Thr
                325                 330                 335 att att gca agt gat gtt gaa att gaa aaa ggt gaa tcg ttt aat cca       1056
Ile Ile Ala Ser Asp Val Glu Ile Glu Lys Gly Glu Ser Phe Asn Pro
            340                 345                 350 tta aca gac tca aga gtg agg ctg tct gca caa gat tca ttg ggt aat       1104
Leu Thr Asp Ser Arg Val Arg Leu Ser Ala Gln Asp Ser Leu Gly Asn
        355                 360                 365 gat att act tca aaa gta aag gtg aaa tca agt aat gtg gat act tcg       1152
Asp Ile Thr Ser Lys Val Lys Val Lys Ser Ser Asn Val Asp Thr Ser
    370                 375                 380 aaa cca ggt gaa tat gat gtt gtg ttt gaa gtg acc gat aat ttt ggt       1200
Lys Pro Gly Glu Tyr Asp Val Val Phe Glu Val Thr Asp Asn Phe Gly
385                 390                 395                 400 ggg aaa gca gaa aaa gaa atc aag gtt aca gtt tta ggg cag cca agt       1248
Gly Lys Ala Glu Lys Glu Ile Lys Val Thr Val Leu Gly Gln Pro Ser
                405                 410                 415 att gaa gcg aat gat gtt gaa tta gaa ata ggt gat tta ttt aat ccg       1296
Ile Glu Ala Asn Asp Val Glu Leu Glu Ile Gly Asp Leu Phe Asn Pro
            420                 425                 430 tta aca gat tca caa gta ggc ctt cgt gca aaa gac tca tta ggc aaa       1344
Leu Thr Asp Ser Gln Val Gly Leu Arg Ala Lys Asp Ser Leu Gly Lys
        435                 440                 445 gat att acg aat gat gtg aaa gta aag tca agt aat gtg gat act tca       1392
Asp Ile Thr Asn Asp Val Lys Val Lys Ser Ser Asn Val Asp Thr Ser
    450                 455                 460 aaa cca gga gaa tat gaa gtt gta ttt gaa gtg acc gat cgt ttt gga       1440
Lys Pro Gly Glu Tyr Glu Val Val Phe Glu Val Thr Asp Arg Phe Gly
465                 470                 475                 480 aaa aaa gca gaa aaa agt atc aaa gtc ctt gtt cta gga gaa cca agc       1488
Lys Lys Ala Glu Lys Ser Ile Lys Val Leu Val Leu Gly Glu Pro Ser
                485                 490                 495 att gaa gca aat aat gtt gag att gaa aaa gac gaa agg ttc gat cca       1536
Ile Glu Ala Asn Asn Val Glu Ile Glu Lys Asp Glu Arg Phe Asp Pro
            500                 505                 510 tta aca gat tca aga gta ggt ctc cgt gca aaa gac tca tta ggc aaa       1584
Leu Thr Asp Ser Arg Val Gly Leu Arg Ala Lys Asp Ser Leu Gly Lys
        515                 520                 525 gat att acg aat gat gtg aaa gta aaa tca agt aat gtg gat act tca       1632
Asp Ile Thr Asn Asp Val Lys Val Lys Ser Ser Asn Val Asp Thr Ser
    530                 535                 540 aaa cca gga gaa tat gaa gtt gta ttt gaa gtg act gat cgt ttt ggt       1680
Lys Pro Gly Glu Tyr Glu Val Val Phe Glu Val Thr Asp Arg Phe Gly
545                 550                 555                 560 aaa tat gta aag aaa ttg att gta gtt ata gta cca gta att gat gat       1728
Lys Tyr Val Lys Lys Leu Ile Val Val Ile Val Pro Val Ile Asp Asp
                565                 570                 575 gaa tgg gaa gat gga aat gtg aat gga tgg aaa ttc tat gcg ggg caa       1776
Glu Trp Glu Asp Gly Asn Val Asn Gly Trp Lys Phe Tyr Ala Gly Gln
            580                 585                 590 gac atc aca ctg ttg aaa gat cct gaa aaa gca tat aaa gga gaa tat       1824
Asp Ile Thr Leu Leu Lys Asp Pro Glu Lys Ala Tyr Lys Gly Glu Tyr
        595                 600                 605
```

```
gta ttc tat gat tct agg cat gct gct att tct aaa aca atc cca gta    1872
Val Phe Tyr Asp Ser Arg His Ala Ala Ile Ser Lys Thr Ile Pro Val
    610                 615                 620 aca gat tta caa gtg gga ggg aat tat gaa att aca gta tat gtt aaa    1920
Thr Asp Leu Gln Val Gly Gly Asn Tyr Glu Ile Thr Val Tyr Val Lys
625                 630                 635                 640 gca gaa agc ggt gat cat cac cta aaa gtg acg tac aag aaa gac ccg    1968
Ala Glu Ser Gly Asp His His Leu Lys Val Thr Tyr Lys Lys Asp Pro
                645                 650                 655 aaa ggt ccg gag gaa cca cca gtt ttc aat aga ctt att agt aca ggg    2016
Lys Gly Pro Glu Glu Pro Pro Val Phe Asn Arg Leu Ile Ser Thr Gly
            660                 665                 670 aaa ttg gtg gaa aaa gac tat aga gaa tta aaa gga aca ttc cgt gta    2064
Lys Leu Val Glu Lys Asp Tyr Arg Glu Leu Lys Gly Thr Phe Arg Val
    675                 680                 685 acg gaa tta aac caa gca cca ttg ata atc gta gag aat ttt ggt gct    2112
Thr Glu Leu Asn Gln Ala Pro Leu Ile Ile Val Glu Asn Phe Gly Ala
690                 695                 700 gga tat ata ggt gga att aga att gtg aaa ata tcg                    2148
Gly Tyr Ile Gly Gly Ile Arg Ile Val Lys Ile Ser
705                 710                 715

<210> SEQ ID NO 2
<211> LENGTH: 716
<212> TYPE: PRT
<213> ORGANISM: Bacillus thuringiensis

<400> SEQUENCE: 2

Met Lys Asp Ser Ile Ser Lys Gly Tyr Asp Glu Ile Thr Val Gln Ala

-continued

```
            225                 230                 235                 240

His Gln Ile Gly Ile Ile Glu Phe Asp Ala Tyr Phe Thr Lys Pro Thr
                245                 250                 255

Ile Glu Ala Asn Asn Val Ser Val Pro Val Gly Ala Thr Phe Asn Pro
            260                 265                 270

Lys Thr Tyr Pro Gly Ile Asn Leu Arg Ala Thr Asp Glu Ile Asp Gly
        275                 280                 285

Asp Leu Thr Ser Glu Ile Ile Val Thr Asp Asn Asn Val Asn Thr Ser
    290                 295                 300

Lys Ser Gly Val Tyr Asn Val Thr Tyr Val Lys Asn Ser Tyr Gly
305                 310                 315                 320

Glu Ser Asp Glu Lys Thr Ile Glu Val Thr Val Phe Ser Asn Pro Thr
                325                 330                 335

Ile Ile Ala Ser Asp Val Glu Ile Glu Lys Gly Glu Ser Phe Asn Pro
            340                 345                 350

Leu Thr Asp Ser Arg Val Arg Leu Ser Ala Gln Asp Ser Leu Gly Asn
        355                 360                 365

Asp Ile Thr Ser Lys Val Lys Val Lys Ser Ser Asn Val Asp Thr Ser
    370                 375                 380

Lys Pro Gly Glu Tyr Asp Val Val Phe Glu Val Thr Asp Asn Phe Gly
385                 390                 395                 400

Gly Lys Ala Glu Lys Glu Ile Lys Val Thr Val Leu Gly Gln Pro Ser
                405                 410                 415

Ile Glu Ala Asn Asp Val Glu Leu Glu Ile Gly Asp Leu Phe Asn Pro
            420                 425                 430

Leu Thr Asp Ser Gln Val Gly Leu Arg Ala Lys Asp Ser Leu Gly Lys
        435                 440                 445

Asp Ile Thr Asn Asp Val Lys Val Lys Ser Ser Asn Val Asp Thr Ser
    450                 455                 460

Lys Pro Gly Glu Tyr Glu Val Val Phe Glu Val Thr Asp Arg Phe Gly
465                 470                 475                 480

Lys Lys Ala Glu Lys Ser Ile Lys Val Leu Val Leu Gly Glu Pro Ser
                485                 490                 495

Ile Glu Ala Asn Asn Val Glu Ile Glu Lys Asp Glu Arg Phe Asp Pro
            500                 505                 510

Leu Thr Asp Ser Arg Val Gly Leu Arg Ala Lys Asp Ser Leu Gly Lys
        515                 520                 525

Asp Ile Thr Asn Asp Val Lys Val Lys Ser Ser Asn Val Asp Thr Ser
    530                 535                 540

Lys Pro Gly Glu Tyr Glu Val Val Phe Glu Val Thr Asp Arg Phe Gly
545                 550                 555                 560

Lys Tyr Val Lys Lys Leu Ile Val Val Ile Pro Val Ile Asp Asp
                565                 570                 575

Glu Trp Glu Asp Gly Asn Val Asn Gly Trp Lys Phe Tyr Ala Gly Gln
            580                 585                 590

Asp Ile Thr Leu Leu Lys Asp Pro Glu Lys Ala Tyr Lys Gly Glu Tyr
        595                 600                 605

Val Phe Tyr Asp Ser Arg His Ala Ala Ile Ser Lys Thr Ile Pro Val
    610                 615                 620

Thr Asp Leu Gln Val Gly Gly Asn Tyr Glu Ile Thr Val Tyr Val Lys
625                 630                 635                 640

Ala Glu Ser Gly Asp His His Leu Lys Val Thr Tyr Lys Lys Asp Pro
                645                 650                 655
```

```
Lys Gly Pro Glu Glu Pro Pro Val Phe Asn Arg Leu Ile Ser Thr Gly
            660                 665                 670

Lys Leu Val Glu Lys Asp Tyr Arg Glu Leu Lys Gly Thr Phe Arg Val
        675                 680                 685

Thr Glu Leu Asn Gln Ala Pro Leu Ile Ile Val Glu Asn Phe Gly Ala
    690                 695                 700

Gly Tyr Ile Gly Gly Ile Arg Ile Val Lys Ile Ser
705                 710                 715

<210> SEQ ID NO 3
<211> LENGTH: 18
<212> TYPE: DNA
<213> ORGANISM: artificial
<220> FEATURE:
<221> NAME/KEY: synthetic oligonucleotide
<222> LOCATION: (1)..(18)
<223> OTHER INFORMATION: completely synthesized

<400> SEQUENCE: 3
catcactttc cccatagc                                               18

<210> SEQ ID NO 4
<211> LENGTH: 22
<212> TYPE: DNA
<213> ORGANISM: artificial
<220> FEATURE:
<221> NAME/KEY: synthetic oligonucleotide
<222> LOCATION: (1)..(22)
<223> OTHER INFORMATION: completely synthesized

<400> SEQUENCE: 4
gacatgattt tacttttaga gc                                          22

<210> SEQ ID NO 5
<211> LENGTH: 23
<212> TYPE: DNA
<213> ORGANISM: artificial
<220> FEATURE:
<221> NAME/KEY: synthetic oligonucleotide
<222> LOCATION: (1)..(23)
<223> OTHER INFORMATION: completely synthesized

<400> SEQUENCE: 5
gcatttcata gaggatcaat tgg                                         23

<210> SEQ ID NO 6
<211> LENGTH: 20
<212> TYPE: DNA
<213> ORGANISM: artificial
<220> FEATURE:
<221> NAME/KEY: synthetic oligonucleotide
<222> LOCATION: (1)..(20)
<223> OTHER INFORMATION: completely synthesized

<400> SEQUENCE: 6
ttttcatcac tttcccccata                                            20

<210> SEQ ID NO 7
<211> LENGTH: 1965
<212> TYPE: DNA
<213> ORGANISM: Bacillus thuringiensis
<220> FEATURE:
<221> NAME/KEY: CDS
<222> LOCATION: (28)..(1923)
<220> FEATURE:
<221> NAME/KEY: misc_feature
```

<222> LOCATION: (28)..(30)
<223> OTHER INFORMATION: alternative methionine initiation codon sequence

<400> SEQUENCE: 7

| | | | | | | |
|---|---|---|---|---|---|---|
| aaatatttttt aaaggggat acgtaat ttg aat tct aaa tct atc atc gaa aaa | | | | | | 54 |
| Leu Asn Ser Lys Ser Ile Ile Glu Lys | | | | | | |
| 1 5 | | | | | | |

```
ggg gta caa gag aat caa tat att gat att cgt aac ata tgt agc att      102
Gly Val Gln Glu Asn Gln Tyr Ile Asp Ile Arg Asn Ile Cys Ser Ile
     10                  15                  20                  25 aat ggt tct gct aaa ttt gat cct aat act aac att aca acc tta aca      150
Asn Gly Ser Ala Lys Phe Asp Pro Asn Thr Asn Ile Thr Thr Leu Thr
                 30                  35                  40 gaa gct atc aat tct caa gca gga gcg att gct gga aaa act gcc cta      198
Glu Ala Ile Asn Ser Gln Ala Gly Ala Ile Ala Gly Lys Thr Ala Leu
             45                  50                  55 gat atg aga cgt gat ttt act ctc gta gca gat ata tac cta ggg tct      246
Asp Met Arg Arg Asp Phe Thr Leu Val Ala Asp Ile Tyr Leu Gly Ser
         60                  65                  70 aaa agt agt gga gct gat ggt att gct ata gcg ttt cat aga gga tca      294
Lys Ser Ser Gly Ala Asp Gly Ile Ala Ile Ala Phe His Arg Gly Ser
     75                  80                  85 att ggt ttt atc ggt acc atg ggt gga ggc tta ggg att cta gga gca      342
Ile Gly Phe Ile Gly Thr Met Gly Gly Gly Leu Gly Ile Leu Gly Ala
 90                  95                 100                 105 cca aac ggg ata gga ttt gaa ata gat acg tat tgg aaa gca act tca      390
Pro Asn Gly Ile Gly Phe Glu Ile Asp Thr Tyr Trp Lys Ala Thr Ser
                110                 115                 120 gat gaa aca ggc gat tca ttt gga cat ggt caa atg aat gga gca cat      438
Asp Glu Thr Gly Asp Ser Phe Gly His Gly Gln Met Asn Gly Ala His
            125                 130                 135 gcg gga ttt gta agt aca aat cga aat gca agc tat tta aca gcc tta      486
Ala Gly Phe Val Ser Thr Asn Arg Asn Ala Ser Tyr Leu Thr Ala Leu
        140                 145                 150 gct cct atg caa aaa ata cct gca cct aat aat aaa tgg cgg gtt cta      534
Ala Pro Met Gln Lys Ile Pro Ala Pro Asn Asn Lys Trp Arg Val Leu
    155                 160                 165 act atc aat tgg gat gcg cgt aac aac aaa cta aca gca cgg ctt caa      582
Thr Ile Asn Trp Asp Ala Arg Asn Asn Lys Leu Thr Ala Arg Leu Gln
170                 175                 180                 185 gag aaa agt aat gat gct tct act agc act cct agt cca aga tat caa      630
Glu Lys Ser Asn Asp Ala Ser Thr Ser Thr Pro Ser Pro Arg Tyr Gln
                190                 195                 200 aca tgg gaa cta tta aat cct gcg ttt gat tta aat cag aaa tat act      678
Thr Trp Glu Leu Leu Asn Pro Ala Phe Asp Leu Asn Gln Lys Tyr Thr
            205                 210                 215 ttt att atc ggc tca gct aca ggg gct gct aat aac aag cat cag att      726
Phe Ile Ile Gly Ser Ala Thr Gly Ala Ala Asn Asn Lys His Gln Ile
        220                 225                 230 gga gtt act ttg ttt gaa gca tac ttt aca aaa cca act ata gag gca      774
Gly Val Thr Leu Phe Glu Ala Tyr Phe Thr Lys Pro Thr Ile Glu Ala
    235                 240                 245 aat cct gtt gat att gaa cta ggc aca gcg ttt gat cca tta aac cat      822
Asn Pro Val Asp Ile Glu Leu Gly Thr Ala Phe Asp Pro Leu Asn His
250                 255                 260                 265 gag cca att gga ctc aaa gca aca gat gaa gta gat gga gat ata aca      870
Glu Pro Ile Gly Leu Lys Ala Thr Asp Glu Val Asp Gly Asp Ile Thr
                270                 275                 280 aag gac att acg gta gaa ttt aat gac ata gat acc tcc aaa cca ggt      918
```

```
                                                                -continued

Lys Asp Ile Thr Val Glu Phe Asn Asp Ile Asp Thr Ser Lys Pro Gly
            285                 290                 295 gca tac cgt gta aca tat aaa gta gta aat agt tat gga gaa agt gat       966
Ala Tyr Arg Val Thr Tyr Lys Val Val Asn Ser Tyr Gly Glu Ser Asp
        300                 305                 310 gag aaa aca ata gaa gtc gta gta tac acg aaa cca act ata act gca      1014
Glu Lys Thr Ile Glu Val Val Val Tyr Thr Lys Pro Thr Ile Thr Ala
    315                 320                 325 cat gat att acg att aag aaa gac tta gca ttt gat cca tta aac tat      1062
His Asp Ile Thr Ile Lys Lys Asp Leu Ala Phe Asp Pro Leu Asn Tyr
330                 335                 340                 345 gaa cca att gga ctc aaa gca acc gat cca att gat gga gat ata aca      1110
Glu Pro Ile Gly Leu Lys Ala Thr Asp Pro Ile Asp Gly Asp Ile Thr
                350                 355                 360 gat aaa atc gct gta aaa ttt aat aat gtc gat acc tct aaa ccg ggt      1158
Asp Lys Ile Ala Val Lys Phe Asn Asn Val Asp Thr Ser Lys Pro Gly
            365                 370                 375 aaa tac cat gta aca tat aaa gtg ata aat agt tat gaa aaa att gat      1206
Lys Tyr His Val Thr Tyr Lys Val Ile Asn Ser Tyr Glu Lys Ile Asp
        380                 385                 390 gaa aaa aca ata gag gtc aca gta tat acg aaa cca tct ata gtg gca      1254
Glu Lys Thr Ile Glu Val Thr Val Tyr Thr Lys Pro Ser Ile Val Ala
    395                 400                 405 cat gat gtt gag att aaa aaa gat acg gca ttt gat ccg tta aac tat      1302
His Asp Val Glu Ile Lys Lys Asp Thr Ala Phe Asp Pro Leu Asn Tyr
410                 415                 420                 425 gaa cca att ggg ctc aaa gca acc gat cca att gat gga gat ata aca      1350
Glu Pro Ile Gly Leu Lys Ala Thr Asp Pro Ile Asp Gly Asp Ile Thr
                430                 435                 440 gat aaa att acg gta gaa tct aat gat gtt gat acc tct aaa cca ggt      1398
Asp Lys Ile Thr Val Glu Ser Asn Asp Val Asp Thr Ser Lys Pro Gly
            445                 450                 455 gca tat agt gtg aaa tat aaa gta gta aat aat tat gaa gaa agt gac      1446
Ala Tyr Ser Val Lys Tyr Lys Val Val Asn Asn Tyr Glu Glu Ser Asp
        460                 465                 470 gaa aaa aca att gcc gtt aca gta cct gtt ata gat gat ggg tgg gag      1494
Glu Lys Thr Ile Ala Val Thr Val Pro Val Ile Asp Asp Gly Trp Glu
    475                 480                 485 aat ggc gat ccg aca gga tgg aaa ttc ttc tct ggt gaa acc att act      1542
Asn Gly Asp Pro Thr Gly Trp Lys Phe Phe Ser Gly Glu Thr Ile Thr
490                 495                 500                 505 cta gaa gat gat gaa gag cat gct ctt aat ggt aaa tgg gta ttt tat      1590
Leu Glu Asp Asp Glu Glu His Ala Leu Asn Gly Lys Trp Val Phe Tyr
                510                 515                 520 gct gat aaa cat gta gca ata tac aaa caa gta gag ttg aag aat aat      1638
Ala Asp Lys His Val Ala Ile Tyr Lys Gln Val Glu Leu Lys Asn Asn
            525                 530                 535 atc cct tat caa att aca gta tat gtt aaa cca gaa gat gaa gga act      1686
Ile Pro Tyr Gln Ile Thr Val Tyr Val Lys Pro Glu Asp Glu Gly Thr
        540                 545                 550 gtg gca cac cat att gtt aaa gta tct ttc aaa tct gat tct gct ggt      1734
Val Ala His His Ile Val Lys Val Ser Phe Lys Ser Asp Ser Ala Gly
    555                 560                 565 cca gaa agt gaa gaa gtt ata aat gaa aga tta att gat gca gaa cag      1782
Pro Glu Ser Glu Glu Val Ile Asn Glu Arg Leu Ile Asp Ala Glu Gln
570                 575                 580                 585 ata caa aaa gga tac aga aag tta aca agt att cca ttt aca cca aca      1830
Ile Gln Lys Gly Tyr Arg Lys Leu Thr Ser Ile Pro Phe Thr Pro Thr
                590                 595                 600
```

```
acc att gtt ccc aac aaa aaa cca gtg ata att gtt gaa aac ttt tta     1878
Thr Ile Val Pro Asn Lys Lys Pro Val Ile Ile Val Glu Asn Phe Leu
            605                 610                 615 cca gga tgg ata ggt gga gtt aga ata att gta gag cct aca aag         1923
Pro Gly Trp Ile Gly Gly Val Arg Ile Ile Val Glu Pro Thr Lys
        620                 625                 630 taagaattat aaactagctt ttaataaata tatttaaaaa at                       1965
```

<210> SEQ ID NO 8
<211> LENGTH: 632
<212> TYPE: PRT
<213> ORGANISM: Bacillus thuringiensis
<220> FEATURE:
<221> NAME/KEY: misc_feature
<222> LOCATION: (28)..(30)
<223> OTHER INFORMATION: alternative methionine initiation codon sequence

<400> SEQUENCE: 8

```
Leu Asn Ser Lys Ser Ile Ile Glu Lys Gly Val Gln Glu Asn Gln Tyr
1               5                   10                  15

Ile Asp Ile Arg Asn Ile Cys Ser Ile Asn Gly Ser Ala Lys Phe Asp
            20                  25                  30

Pro Asn Thr Asn Ile Thr Thr Leu Thr Glu Ala Ile Asn Ser Gln Ala
        35                  40                  45

Gly Ala Ile Ala Gly Lys Thr Ala Leu Asp Met Arg Arg Asp Phe Thr
    50                  55                  60

Leu Val Ala Asp Ile Tyr Leu Gly Ser Lys Ser Ser Gly Ala Asp Gly
65                  70                  75                  80

Ile Ala Ile Ala Phe His Arg Gly Ser Ile Gly Phe Ile Gly Thr Met
                85                  90                  95

Gly Gly Gly Leu Gly Ile Leu Gly Ala Pro Asn Gly Ile Gly Phe Glu
            100                 105                 110

Ile Asp Thr Tyr Trp Lys Ala Thr Ser Asp Glu Thr Gly Asp Ser Phe
        115                 120                 125

Gly His Gly Gln Met Asn Gly Ala His Ala Gly Phe Val Ser Thr Asn
    130                 135                 140

Arg Asn Ala Ser Tyr Leu Thr Ala Leu Ala Pro Met Gln Lys Ile Pro
145                 150                 155                 160

Ala Pro Asn Asn Lys Trp Arg Val Leu Thr Ile Asn Trp Asp Ala Arg
                165                 170                 175

Asn Asn Lys Leu Thr Ala Arg Leu Gln Glu Lys Ser Asn Asp Ala Ser
            180                 185                 190

Thr Ser Thr Pro Ser Pro Arg Tyr Gln Thr Trp Glu Leu Leu Asn Pro
        195                 200                 205

Ala Phe Asp Leu Asn Gln Lys Tyr Thr Phe Ile Ile Gly Ser Ala Thr
    210                 215                 220

Gly Ala Ala Asn Asn Lys His Gln Ile Gly Val Thr Leu Phe Glu Ala
225                 230                 235                 240

Tyr Phe Thr Lys Pro Thr Ile Glu Ala Asn Pro Val Asp Ile Glu Leu
                245                 250                 255

Gly Thr Ala Phe Asp Pro Leu Asn His Glu Pro Ile Gly Leu Lys Ala
            260                 265                 270

Thr Asp Glu Val Asp Gly Asp Ile Thr Lys Asp Ile Thr Val Glu Phe
        275                 280                 285

Asn Asp Ile Asp Thr Ser Lys Pro Gly Ala Tyr Arg Val Thr Tyr Lys
    290                 295                 300
```

```
Val Val Asn Ser Tyr Gly Glu Ser Asp Glu Lys Thr Ile Glu Val Val
305                 310                 315                 320

Val Tyr Thr Lys Pro Thr Ile Thr Ala His Asp Ile Thr Ile Lys Lys
            325                 330                 335

Asp Leu Ala Phe Asp Pro Leu Asn Tyr Glu Pro Ile Gly Leu Lys Ala
            340                 345                 350

Thr Asp Pro Ile Asp Gly Asp Ile Thr Asp Lys Ile Ala Val Lys Phe
            355                 360                 365

Asn Asn Val Asp Thr Ser Lys Pro Gly Lys Tyr His Val Thr Tyr Lys
370                 375                 380

Val Ile Asn Ser Tyr Glu Lys Ile Asp Glu Lys Thr Ile Glu Val Thr
385                 390                 395                 400

Val Tyr Thr Lys Pro Ser Ile Val Ala His Asp Val Glu Ile Lys Lys
            405                 410                 415

Asp Thr Ala Phe Asp Pro Leu Asn Tyr Glu Pro Ile Gly Leu Lys Ala
            420                 425                 430

Thr Asp Pro Ile Asp Gly Asp Ile Thr Asp Lys Ile Thr Val Glu Ser
            435                 440                 445

Asn Asp Val Asp Thr Ser Lys Pro Gly Ala Tyr Ser Val Lys Tyr Lys
450                 455                 460

Val Val Asn Asn Tyr Glu Glu Ser Asp Glu Lys Thr Ile Ala Val Thr
465                 470                 475                 480

Val Pro Val Ile Asp Asp Gly Trp Glu Asn Gly Asp Pro Thr Gly Trp
            485                 490                 495

Lys Phe Phe Ser Gly Glu Thr Ile Thr Leu Glu Asp Asp Glu His
            500                 505                 510

Ala Leu Asn Gly Lys Trp Val Phe Tyr Ala Asp Lys His Val Ala Ile
            515                 520                 525

Tyr Lys Gln Val Glu Leu Lys Asn Asn Ile Pro Tyr Gln Ile Thr Val
530                 535                 540

Tyr Val Lys Pro Glu Asp Glu Gly Thr Val Ala His His Ile Val Lys
545                 550                 555                 560

Val Ser Phe Lys Ser Asp Ser Ala Gly Pro Glu Ser Glu Glu Val Ile
            565                 570                 575

Asn Glu Arg Leu Ile Asp Ala Glu Gln Ile Gln Lys Gly Tyr Arg Lys
            580                 585                 590

Leu Thr Ser Ile Pro Phe Thr Pro Thr Ile Val Pro Asn Lys Lys
            595                 600                 605

Pro Val Ile Ile Val Glu Asn Phe Leu Pro Gly Trp Ile Gly Gly Val
    610                 615                 620

Arg Ile Ile Val Glu Pro Thr Lys
625                 630

<210> SEQ ID NO 9
<211> LENGTH: 2172
<212> TYPE: DNA
<213> ORGANISM: Bacillus thuringiensis
<220> FEATURE:
<221> NAME/KEY: CDS
<222> LOCATION: (1)..(2166)
<223> OTHER INFORMATION: Cry22 Amino Acid Sequence

<400> SEQUENCE: 9 atg aaa gaa caa aat cta aat aaa tat gat gaa ata act gta caa gca    48
Met Lys Glu Gln Asn Leu Asn Lys Tyr Asp Glu Ile Thr Val Gln Ala
1               5                   10                  15
```

```
gca agc gat tat atc gac att cgt ccg att ttt caa aca aat gga tct      96
Ala Ser Asp Tyr Ile Asp Ile Arg Pro Ile Phe Gln Thr Asn Gly Ser
         20                  25                  30 gct aca ttt aat tct aat acc aat att aca act tta aca caa gct ata     144
Ala Thr Phe Asn Ser Asn Thr Asn Ile Thr Thr Leu Thr Gln Ala Ile
     35                  40                  45 aat agt caa gca gga gca att gca gga aag act gct cta gat atg aga     192
Asn Ser Gln Ala Gly Ala Ile Ala Gly Lys Thr Ala Leu Asp Met Arg
 50                  55                  60 cat gac ttt act ttt aga gca gat att ttt ctt gga act aaa agt aac     240
His Asp Phe Thr Phe Arg Ala Asp Ile Phe Leu Gly Thr Lys Ser Asn
 65                  70                  75                  80 gga gca gac ggt att gca atc gca ttt cat aga gga tca att ggg ttt     288
Gly Ala Asp Gly Ile Ala Ile Ala Phe His Arg Gly Ser Ile Gly Phe
             85                  90                  95 gtt gga aca aaa ggc gga gga ctt gga ata tta ggt gca cct aaa ggg     336
Val Gly Thr Lys Gly Gly Gly Leu Gly Ile Leu Gly Ala Pro Lys Gly
        100                 105                 110 ata ggg ttt gaa tta gac aca tat gcg aat gca cct gag gac gaa gta     384
Ile Gly Phe Glu Leu Asp Thr Tyr Ala Asn Ala Pro Glu Asp Glu Val
        115                 120                 125 ggc gat tcg ttt ggg cat ggg gca atg aaa gga tca ttc cct agt ttc     432
Gly Asp Ser Phe Gly His Gly Ala Met Lys Gly Ser Phe Pro Ser Phe
130                 135                 140 cca aat gga tat ccc cat gct ggc ttt gta agt act gat aaa aat agt     480
Pro Asn Gly Tyr Pro His Ala Gly Phe Val Ser Thr Asp Lys Asn Ser
145                 150                 155                 160 aga tgg tta tca gct cta gct cag atg cag cga atc gct gct cca aac     528
Arg Trp Leu Ser Ala Leu Ala Gln Met Gln Arg Ile Ala Ala Pro Asn
                165                 170                 175 ggg cgt tgg aga cgt ctg gag att cgt tgg gat gct cgt aat aaa gag     576
Gly Arg Trp Arg Arg Leu Glu Ile Arg Trp Asp Ala Arg Asn Lys Glu
        180                 185                 190 tta act gca aat ctt cag gat tta act ttt aat gac ata act gtt gga     624
Leu Thr Ala Asn Leu Gln Asp Leu Thr Phe Asn Asp Ile Thr Val Gly
        195                 200                 205 gag aag cca cgt act cca aga act gca act tgg agg tta gta aat cct     672
Glu Lys Pro Arg Thr Pro Arg Thr Ala Thr Trp Arg Leu Val Asn Pro
        210                 215                 220 gca ttt gaa ctt gat cag aag tat act ttt gtt att ggt tcg gcg acg     720
Ala Phe Glu Leu Asp Gln Lys Tyr Thr Phe Val Ile Gly Ser Ala Thr
225                 230                 235                 240 ggt gca tct aat aac cta cat cag att ggg att ata gaa ttt gat gca     768
Gly Ala Ser Asn Asn Leu His Gln Ile Gly Ile Ile Glu Phe Asp Ala
                245                 250                 255 tac ttt act aaa ccg aca ata gaa gcg aat aat gta aat gtc cca gtg     816
Tyr Phe Thr Lys Pro Thr Ile Glu Ala Asn Asn Val Asn Val Pro Val
        260                 265                 270 gga gca aca ttt aat cca aaa aca tat cca gga ata aat tta aga gca     864
Gly Ala Thr Phe Asn Pro Lys Thr Tyr Pro Gly Ile Asn Leu Arg Ala
        275                 280                 285 aca gat gag ata gat ggg gat ttg aca tcg aag att att gtg aaa gca     912
Thr Asp Glu Ile Asp Gly Asp Leu Thr Ser Lys Ile Ile Val Lys Ala
        290                 295                 300 aac aat gtt aat acg tcg aaa acg ggt gtg tat tat gtg acg tat tat     960
Asn Asn Val Asn Thr Ser Lys Thr Gly Val Tyr Tyr Val Thr Tyr Tyr
305                 310                 315                 320 gta gag aat agt tat ggg gaa agt gat gaa aaa aca atc gaa gta act    1008
Val Glu Asn Ser Tyr Gly Glu Ser Asp Glu Lys Thr Ile Glu Val Thr
```

-continued

|  |  |  |  |
|---|---|---|---|
| | 325 | 330 | 335 |
| gtg ttt tca aac cct aca att att gca agt gat gtt gaa att gaa aaa<br>Val Phe Ser Asn Pro Thr Ile Ile Ala Ser Asp Val Glu Ile Glu Lys<br>340 345 350 | | | 1056 |
| ggg gaa tct ttt aac cca cta act gat tca aga gta ggt ctt tct gca<br>Gly Glu Ser Phe Asn Pro Leu Thr Asp Ser Arg Val Gly Leu Ser Ala<br>355 360 365 | | | 1104 |
| cag gat tca tta ggc aat gat att acc caa aat gta aag gta aaa tcg<br>Gln Asp Ser Leu Gly Asn Asp Ile Thr Gln Asn Val Lys Val Lys Ser<br>370 375 380 | | | 1152 |
| agt aat gtg gat act tca aag cca ggg gaa tat gaa gtt gta ttt gaa<br>Ser Asn Val Asp Thr Ser Lys Pro Gly Glu Tyr Glu Val Val Phe Glu<br>385 390 395 400 | | | 1200 |
| gtg aca gat agc ttt ggt gga aaa gca gaa aaa gat ttc aag gtt aca<br>Val Thr Asp Ser Phe Gly Gly Lys Ala Glu Lys Asp Phe Lys Val Thr<br>405 410 415 | | | 1248 |
| gtt tta gga cag cca agt ata gaa gcg aat aat gtt gaa tta gaa ata<br>Val Leu Gly Gln Pro Ser Ile Glu Ala Asn Asn Val Glu Leu Glu Ile<br>420 425 430 | | | 1296 |
| gat gat tca ttg gat cca tta aca gat gca aaa gta ggt ctc cgt gca<br>Asp Asp Ser Leu Asp Pro Leu Thr Asp Ala Lys Val Gly Leu Arg Ala<br>435 440 445 | | | 1344 |
| aag gat tca tta ggt aat gat att acg aaa gac ata aaa gta aag ttc<br>Lys Asp Ser Leu Gly Asn Asp Ile Thr Lys Asp Ile Lys Val Lys Phe<br>450 455 460 | | | 1392 |
| aat aac gta gat act tca aat tca gga aag tat gaa gtt ata ttt gaa<br>Asn Asn Val Asp Thr Ser Asn Ser Gly Lys Tyr Glu Val Ile Phe Glu<br>465 470 475 480 | | | 1440 |
| gtg acg gac cgt ttt gga aaa aaa gca gaa aaa agt att gaa gtc ctt<br>Val Thr Asp Arg Phe Gly Lys Lys Ala Glu Lys Ser Ile Glu Val Leu<br>485 490 495 | | | 1488 |
| gtt cta gga gaa cca agc att gaa gca aat gat gtt gag gtt aat aaa<br>Val Leu Gly Glu Pro Ser Ile Glu Ala Asn Asp Val Glu Val Asn Lys<br>500 505 510 | | | 1536 |
| ggt gaa acg ttt gaa cca tta aca gat tca aga gtt ggc ctc cgt gca<br>Gly Glu Thr Phe Glu Pro Leu Thr Asp Ser Arg Val Gly Leu Arg Ala<br>515 520 525 | | | 1584 |
| aaa gac tca tta ggt aat gat att acg aaa gat gtg aaa ata aaa tca<br>Lys Asp Ser Leu Gly Asn Asp Ile Thr Lys Asp Val Lys Ile Lys Ser<br>530 535 540 | | | 1632 |
| agt aat gtg gat act tca aaa cca ggt gaa tat gaa gtt gta ttt gaa<br>Ser Asn Val Asp Thr Ser Lys Pro Gly Glu Tyr Glu Val Val Phe Glu<br>545 550 555 560 | | | 1680 |
| gtg aca gat cgt ttt ggt aaa tat gta gaa aaa aca att gga gtt ata<br>Val Thr Asp Arg Phe Gly Lys Tyr Val Glu Lys Thr Ile Gly Val Ile<br>565 570 575 | | | 1728 |
| gtg cca gta att gat gat gaa tgg gaa gat gga aat gtg aat ggt tgg<br>Val Pro Val Ile Asp Asp Glu Trp Glu Asp Gly Asn Val Asn Gly Trp<br>580 585 590 | | | 1776 |
| aaa ttc tat gct ggg caa gat att aaa ctg ttg aag gat cct gat aaa<br>Lys Phe Tyr Ala Gly Gln Asp Ile Lys Leu Leu Lys Asp Pro Asp Lys<br>595 600 605 | | | 1824 |
| gcc tat aaa ggc gat tat gta ttc tat gat tct aga cac gtt gct att<br>Ala Tyr Lys Gly Asp Tyr Val Phe Tyr Asp Ser Arg His Val Ala Ile<br>610 615 620 | | | 1872 |
| tct aaa aca att cca cta acg gat ttg caa ata aat aca aac tat gaa<br>Ser Lys Thr Ile Pro Leu Thr Asp Leu Gln Ile Asn Thr Asn Tyr Glu<br>625 630 635 640 | | | 1920 |
| att aca gtg tat gct aaa gca gaa agc ggc gat cat cac tta aaa gtg | | | 1968 |

```
Ile Thr Val Tyr Ala Lys Ala Glu Ser Gly Asp His His Leu Lys Val
                645                 650                 655 acg tat aag aaa gac ccg gca ggt cca gaa gag ccg cca gtt ttc aat    2016
Thr Tyr Lys Lys Asp Pro Ala Gly Pro Glu Glu Pro Pro Val Phe Asn
            660                 665                 670 aga ctg att agc aca ggc aca ttg gta gaa aaa gat tat aga gaa tta    2064
Arg Leu Ile Ser Thr Gly Thr Leu Val Glu Lys Asp Tyr Arg Glu Leu
        675                 680                 685 aaa ggg acg ttc cgc gta aca gaa tta aac aaa gca cca ttg ata atc    2112
Lys Gly Thr Phe Arg Val Thr Glu Leu Asn Lys Ala Pro Leu Ile Ile
    690                 695                 700 gta gag aat ttt gga gct gga tat ata ggt gga att aga att gtg aaa    2160
Val Glu Asn Phe Gly Ala Gly Tyr Ile Gly Gly Ile Arg Ile Val Lys
705                 710                 715                 720 ata tcg taataa                                                      2172
Ile Ser <210> SEQ ID NO 10
<211> LENGTH: 722
<212> TYPE: PRT
<213> ORGANISM: Bacillus thuringiensis

<400> SEQUENCE: 10

Met Lys Glu Gln Asn Leu Asn Lys Tyr Asp Glu Ile Thr Val Gln Ala
1               5                   10                  15

Ala Ser Asp Tyr Ile Asp Ile Arg Pro Ile Phe Gln Thr Asn Gly Ser
            20                  25                  30

Ala Thr Phe Asn Ser Asn Thr Asn Ile Thr Thr Leu Thr Gln Ala Ile
        35                  40                  45

Asn Ser Gln Ala Gly Ala Ile Ala Gly Lys Thr Ala Leu Asp Met Arg
    50                  55                  60

His Asp Phe Thr Phe Arg Ala Asp Ile Phe Leu Gly Thr Lys Ser Asn
65                  70                  75                  80

Gly Ala Asp Gly Ile Ala Ile Ala Phe His Arg Gly Ser Ile Gly Phe
                85                  90                  95

Val Gly Thr Lys Gly Gly Gly Leu Gly Ile Leu Gly Ala Pro Lys Gly
            100                 105                 110

Ile Gly Phe Glu Leu Asp Thr Tyr Ala Asn Ala Pro Glu Asp Glu Val
        115                 120                 125

Gly Asp Ser Phe Gly His Gly Ala Met Lys Gly Ser Phe Pro Ser Phe
    130                 135                 140

Pro Asn Gly Tyr Pro His Ala Gly Phe Val Ser Thr Asp Lys Asn Ser
145                 150                 155                 160

Arg Trp Leu Ser Ala Leu Ala Gln Met Gln Arg Ile Ala Ala Pro Asn
                165                 170                 175

Gly Arg Trp Arg Arg Leu Glu Ile Arg Trp Asp Ala Arg Asn Lys Glu
            180                 185                 190

Leu Thr Ala Asn Leu Gln Asp Leu Thr Phe Asn Asp Ile Thr Val Gly
        195                 200                 205

Glu Lys Pro Arg Thr Pro Arg Thr Ala Thr Trp Arg Leu Val Asn Pro
    210                 215                 220

Ala Phe Glu Leu Asp Gln Lys Tyr Thr Phe Val Ile Gly Ser Ala Thr
225                 230                 235                 240

Gly Ala Ser Asn Asn Leu His Gln Ile Gly Ile Ile Glu Phe Asp Ala
                245                 250                 255

Tyr Phe Thr Lys Pro Thr Ile Glu Ala Asn Asn Val Asn Val Pro Val
```

-continued

```
                260                 265                 270
Gly Ala Thr Phe Asn Pro Lys Thr Tyr Pro Gly Ile Asn Leu Arg Ala
            275                 280                 285
Thr Asp Glu Ile Asp Gly Asp Leu Thr Ser Lys Ile Ile Val Lys Ala
            290                 295                 300
Asn Asn Val Asn Thr Ser Lys Thr Gly Val Tyr Tyr Val Thr Tyr Tyr
305                 310                 315                 320
Val Glu Asn Ser Tyr Gly Ser Asp Glu Lys Thr Ile Glu Val Thr
                325                 330                 335
Val Phe Ser Asn Pro Thr Ile Ile Ala Ser Asp Val Glu Ile Glu Lys
            340                 345                 350
Gly Glu Ser Phe Asn Pro Leu Thr Asp Ser Arg Val Gly Leu Ser Ala
            355                 360                 365
Gln Asp Ser Leu Gly Asn Asp Ile Thr Gln Asn Val Lys Val Lys Ser
            370                 375                 380
Ser Asn Val Asp Thr Ser Lys Pro Gly Glu Tyr Glu Val Val Phe Glu
385                 390                 395                 400
Val Thr Asp Ser Phe Gly Gly Lys Ala Glu Lys Asp Phe Lys Val Thr
            405                 410                 415
Val Leu Gly Gln Pro Ser Ile Glu Ala Asn Asn Val Glu Leu Glu Ile
            420                 425                 430
Asp Asp Ser Leu Asp Pro Leu Thr Asp Ala Lys Val Gly Leu Arg Ala
            435                 440                 445
Lys Asp Ser Leu Gly Asn Asp Ile Thr Lys Asp Ile Lys Val Lys Phe
            450                 455                 460
Asn Asn Val Asp Thr Ser Asn Ser Gly Lys Tyr Glu Val Ile Phe Glu
465                 470                 475                 480
Val Thr Asp Arg Phe Gly Lys Lys Ala Glu Lys Ser Ile Glu Val Leu
            485                 490                 495
Val Leu Gly Glu Pro Ser Ile Glu Ala Asn Asp Val Glu Val Asn Lys
            500                 505                 510
Gly Glu Thr Phe Glu Pro Leu Thr Asp Ser Arg Val Gly Leu Arg Ala
            515                 520                 525
Lys Asp Ser Leu Gly Asn Asp Ile Thr Lys Asp Val Lys Ile Lys Ser
            530                 535                 540
Ser Asn Val Asp Thr Ser Lys Pro Gly Glu Tyr Glu Val Val Phe Glu
545                 550                 555                 560
Val Thr Asp Arg Phe Gly Lys Tyr Val Glu Lys Thr Ile Gly Val Ile
                565                 570                 575
Val Pro Val Ile Asp Asp Glu Trp Glu Asp Gly Asn Val Asn Gly Trp
            580                 585                 590
Lys Phe Tyr Ala Gly Gln Asp Ile Lys Leu Leu Lys Asp Pro Asp Lys
            595                 600                 605
Ala Tyr Lys Gly Asp Tyr Val Phe Tyr Asp Ser Arg His Val Ala Ile
            610                 615                 620
Ser Lys Thr Ile Pro Leu Thr Asp Leu Gln Ile Asn Thr Asn Tyr Glu
625                 630                 635                 640
Ile Thr Val Tyr Ala Lys Ala Glu Ser Gly Asp His His Leu Lys Val
                645                 650                 655
Thr Tyr Lys Lys Asp Pro Ala Gly Pro Glu Glu Pro Val Phe Asn
            660                 665                 670
Arg Leu Ile Ser Thr Gly Thr Leu Val Glu Lys Asp Tyr Arg Glu Leu
            675                 680                 685
```

```
Lys Gly Thr Phe Arg Val Thr Glu Leu Asn Lys Ala Pro Leu Ile Ile
    690                 695                 700

Val Glu Asn Phe Gly Ala Gly Tyr Ile Gly Gly Ile Arg Ile Val Lys
705                 710                 715                 720

Ile Ser
```

<210> SEQ ID NO 11
<211> LENGTH: 20
<212> TYPE: DNA
<213> ORGANISM: artificial
<220> FEATURE:
<221> NAME/KEY: synthetic oligonucleotide
<222> LOCATION: (1)..(20)
<223> OTHER INFORMATION: completely synthesized

<400> SEQUENCE: 11
attgatcctc tatgaaatgc                                         20

<210> SEQ ID NO 12
<211> LENGTH: 19
<212> TYPE: DNA
<213> ORGANISM: artificial
<220> FEATURE:
<221> NAME/KEY: synthetic oligonucleotide
<222> LOCATION: (1)..(19)
<223> OTHER INFORMATION: completely synthesized

<400> SEQUENCE: 12
gtttcccaaa tggatatcc                                          19

<210> SEQ ID NO 13
<211> LENGTH: 19
<212> TYPE: DNA
<213> ORGANISM: artificial
<220> FEATURE:
<221> NAME/KEY: synthetic oligonucleotide
<222> LOCATION: (1)..(19)
<223> OTHER INFORMATION: completely synthesized

<400> SEQUENCE: 13
ggatatccat ttgggaaac                                          19

<210> SEQ ID NO 14
<211> LENGTH: 20
<212> TYPE: DNA
<213> ORGANISM: artificial
<220> FEATURE:
<221> NAME/KEY: synthetic oligonucleotide
<222> LOCATION: (1)..(20)
<223> OTHER INFORMATION: completely synthesized

<400> SEQUENCE: 14
atctaataac ctacatcaga                                         20

<210> SEQ ID NO 15
<211> LENGTH: 20
<212> TYPE: DNA
<213> ORGANISM: artificial
<220> FEATURE:
<221> NAME/KEY: synthetic oligonucleotide
<222> LOCATION: (1)..(20)
<223> OTHER INFORMATION: completely synthesized

<400> SEQUENCE: 15
tctgatgtag gttattagat                                         20

-continued

```
<210> SEQ ID NO 16
<211> LENGTH: 20
<212> TYPE: DNA
<213> ORGANISM: artificial
<220> FEATURE:
<221> NAME/KEY: synthetic oligonucleotide
<222> LOCATION: (1)..(20)
<223> OTHER INFORMATION: completely synthesized

<400> SEQUENCE: 16 tatgggaaa gtgatgaaaa                                              20

<210> SEQ ID NO 17
<211> LENGTH: 18
<212> TYPE: DNA
<213> ORGANISM: artificial
<220> FEATURE:
<221> NAME/KEY: synthetic oligonucleotide
<222> LOCATION: (1)..(18)
<223> OTHER INFORMATION: completely synthesized

<400> SEQUENCE: 17
atgttgaatt agaaatag                                               18

<210> SEQ ID NO 18
<211> LENGTH: 18
<212> TYPE: DNA
<213> ORGANISM: artificial
<220> FEATURE:
<221> NAME/KEY: synthetic oligonucleotide
<222> LOCATION: (1)..(18)
<223> OTHER INFORMATION: completely synthesized

<400> SEQUENCE: 18
ctatttctaa ttcaacat                                               18

<210> SEQ ID NO 19
<211> LENGTH: 20
<212> TYPE: DNA
<213> ORGANISM: artificial
<220> FEATURE:
<221> NAME/KEY: synthetic oligonucleotide
<222> LOCATION: (1)..(20)
<223> OTHER INFORMATION: completely synthesized

<400> SEQUENCE: 19
aagtccttgt tctaggagaa                                             20

<210> SEQ ID NO 20
<211> LENGTH: 20
<212> TYPE: DNA
<213> ORGANISM: artificial
<220> FEATURE:
<221> NAME/KEY: synthetic oligonucleotide
<222> LOCATION: (1)..(20)
<223> OTHER INFORMATION: completely synthesized

<400> SEQUENCE: 20
ttctcctaga acaaggactt                                             20

<210> SEQ ID NO 21
<211> LENGTH: 20
<212> TYPE: DNA
<213> ORGANISM: artificial
<220> FEATURE:
<221> NAME/KEY: synthetic oligonucleotide
<222> LOCATION: (1)..(20)
<223> OTHER INFORMATION: completely synthesized
```

```
<400> SEQUENCE: 21
tatgtattct atgattctag                                                    20

<210> SEQ ID NO 22
<211> LENGTH: 20
<212> TYPE: DNA
<213> ORGANISM: artificial
<220> FEATURE:
<221> NAME/KEY: synthetic oligonucleotide
<222> LOCATION: (1)..(20)
<223> OTHER INFORMATION: completely synthesized

<400> SEQUENCE: 22
ctagaatcat agaatacata                                                    20
```